US007858356B2

(12) United States Patent
Kaneda et al.

(10) Patent No.: US 7,858,356 B2
(45) Date of Patent: Dec. 28, 2010

(54) MUTANT PARAMYXOVIRUS AND METHOD FOR PRODUCTION THEREOF

(75) Inventors: Yasufumi Kaneda, Suita (JP); Katsuto Tamai, Suita (JP); Kotaro Saga, Suita (JP); Masako Kawachi, Suita (JP)

(73) Assignee: GenomIdea, Inc., Osaka (JP)

( * ) Notice: Subject to any disclaimer, the term of this patent is extended or adjusted under 35 U.S.C. 154(b) by 69 days.

(21) Appl. No.: 12/085,355

(22) PCT Filed: Nov. 24, 2006

(86) PCT No.: PCT/JP2006/324048

§ 371 (c)(1),
(2), (4) Date: May 22, 2008

(87) PCT Pub. No.: WO2007/061141

PCT Pub. Date: May 31, 2007

(65) Prior Publication Data

US 2009/0269850 A1 Oct. 29, 2009

(30) Foreign Application Priority Data

Nov. 24, 2005 (JP) ............................ 2005-338449
Nov. 24, 2005 (JP) ............................ 2005-339474

(51) Int. Cl.

| | |
|---|---|
| ***C12N 7/01*** | (2006.01) |
| ***C12N 7/02*** | (2006.01) |
| ***C12N 5/10*** | (2006.01) |
| ***C12N 15/86*** | (2006.01) |
| ***C12N 15/62*** | (2006.01) |
| ***C12N 15/45*** | (2006.01) |
| ***C07K 14/115*** | (2006.01) |
| ***C07K 19/00*** | (2006.01) |

(52) U.S. Cl. ................. 435/235.1; 435/320.1; 435/325; 435/239; 536/23.4; 536/23.72; 530/350

(58) Field of Classification Search ....................... None
See application file for complete search history.

(56) References Cited

U.S. PATENT DOCUMENTS

| | | | |
|---|---|---|---|
| 2003/0165477 | A1 | 9/2003 | Balloul et al. |
| 2004/0029280 | A1 | 2/2004 | Sosnowski et al. |
| 2006/0110361 | A1 | 5/2006 | Casimir |

FOREIGN PATENT DOCUMENTS

| | | |
|---|---|---|
| JP | 08-504091 | 5/1996 |
| JP | 2001-515493 | 9/2001 |
| JP | 2002-320475 | 11/2002 |
| JP | 2002-330774 | 11/2002 |
| JP | 2005-532075 | 10/2005 |
| WO | 94/06920 | 3/1994 |
| WO | 99/46278 | 9/1999 |
| WO | 03/029416 | 4/2003 |

OTHER PUBLICATIONS

Techaarpornkul et al. "Functional Analysis of Recombinant Respiratory Syncytial Virus Deletion Mutants Lacking the Small Hydrophobic and/or Attachment Glycoprotein Gene." Journal of Virology 75: 6825-6843, 2001.*

Barik. "Control of nonsegmented negative-strand RNA virus replication by siRNA." Virus Research 102:27-35, 2004.*

Schroth-Diez et al (Journal of Virology 72:133-141, 1998).*

Tao et al (Journal of Virology 74:6448-6458, 2000).*

Zimmer et al (Journal of Virology 79:10467-10477, Aug. 2005).*

Sato et al (FASEB Journal 14:2108-2118, 2000).*

Saga et al., "Generation of HN-depleted HVJ virus particles by sIRNA" abstract of The 28th Annual Meeting of the Molecular Biology Society of Japan, p. 561, 2005 (with English translation).

Kawachi et al., "Development of improved HVJ-E vector with high affinity to epidermal keratinocyte" abstract of The 28th Annual Meeting of the Molecular Biology Society of Japan, p. 558, 2005 (with English translation).

Tomita et al., "Targeted gene therapy for rat glomerulonephritis using HVJ-immunoliposomes" The Journal of Gene Medicine, vol. 4, pp. 527-535, Apr. 30, 2002.

Hallak et al., "Targeted Measles Virus Vector Displaying Echistatin Infects Endothelial Cells via αvβ3 and Leads to Tumor Regression" Cancer Res., vol. 65(12), pp. 5292-5300, Jun. 15, 2005.

(Continued)

*Primary Examiner*—Mary E Mosher
(74) *Attorney, Agent, or Firm*—Wenderoth, Lind & Ponack, L.L.P.

(57) ABSTRACT

The present invention provides a modified paramyxovirus containing a reduced amount of receptor-binding protein compared with the wild type; a method of preparing a modified paramyxovirus, comprising the following steps: (1) a step for introducing a nucleic acid that suppresses the expression of a receptor-binding protein of a paramyxovirus into an animal cell, (2) a step for infecting the paramyxovirus to the cell, and (3) a step for isolating paramyxovirus particles replicated in the cell; and a modified paramyxovirus prepared by the method of preparation mentioned above.

The present invention also provides a chimera protein wherein a fusion protein of a virus has been joined or bound to a peptide that binds specifically to a cell surface marker; a nucleic acid that encodes the chimera protein; an animal cell capable of expressing the chimera protein on the cell surface thereof; a modified paramyxovirus expressing the chimera protein on the virus particle surface thereof; and a method of preparing a tissue targeting paramyxovirus, comprising: (1) a step for supplying a nucleic acid that encodes a chimera protein wherein a fusion protein of a virus has been joined or bound to a peptide that binds specifically to a cell surface marker of the target cells, (2) a step for introducing the nucleic acid supplied in (1) into an animal cell in an expressible state, and expressing the same, (3) a step for infecting a paramyxovirus to the cell, and (4) a step for isolating paramyxovirus particles replicated in the cell.

22 Claims, 15 Drawing Sheets

OTHER PUBLICATIONS

Supplementary European Search Report dated Aug. 19, 2010 in International (PCT) Application No. PCT/JP2006/324048.

Schlender, Jörg et al., "Respiratory Syncytial Virus (RSV) Fusion Protein Subunit F2, Not Attachment Protein G, Determines the Specificity of RSV Infection", Journal Virology, vol. 77, No. 8, Apr. 2003, pp. 4609-4616, XP002593949.

Ren, Guijie et al., "Effects of Heptad Repeat Regions of F Protein on the Specific Membrane Fusion in Paramyxoviruses", Intervirology, vol. 49, No. 5, Jul. 3, 2006, pp. 299-306, XP002593950.

Kawachi, Masako et al., "Development of Tissue-Targeting Hemagglutinating Virus of Japan Envelope Vector for Successful Delivery of Therapeutic Gene to Mouse Skin" Human Gene Therapy, vol. 18, No. 10, Oct. 2007, pp. 881-894, XP002593951.

* cited by examiner

MUTANT PARAMYXOVIRUS AND METHOD FOR PRODUCTION THEREOF

This application is a U.S. national stage of International Application No. PCT/JP2006/324048 filed Nov. 24, 2006.

TECHNICAL FIELD

The present invention relates to a modified paramyxovirus containing a reduced amount of a receptor-binding protein, and a method of preparing a modified paramyxovirus using a nucleic acid that suppresses the expression of the receptor-binding protein. Specifically, the present invention relates to a modified HVJ containing a reduced amount of HN protein, and a method of preparing a modified HVJ using an siRNA.

The present invention also relates to a vector capable of site-specific delivery of a drug and a method of preparing the same.

BACKGROUND ART

In order to introduce a gene to a cultured cell or living tissue for gene function analysis or gene therapy, many viral methods and non-viral methods have been developed (Mulligan, Science, vol. 260, p. 926-932, (1993); Ledley, Human Gene Therapy, vol. 6, p. 1129-1144 (1995)). Generally, in introducing genes into cells, viral methods are effective. However, methods using viral vectors involve possible introduction of a gene derived from the parent virus and expression thereof, immunogenicity, and possible modification of the host genome structure, posing a problem with safety. Meanwhile, many of non-viral methods, which use liposomes and the like, tend to be inferior to viral vectors in terms of the efficiency of gene introduction to a cultured cell or living tissue, though the cytotoxicity and immunogenicity thereof are lower than those of viral methods.

It is thought that viruses gradually change the functions thereof to achieve coexistence with the host by repeating mutations, even though they are initially fatally pathogenic to the host, whereby they can survive. Therefore, many mutants, even in a single virus, occur in the natural world; it can be said that investigations thereof have led to the elucidation of the functions possessed by viruses at the molecular level. This fact is not only valuable from the viewpoint of basic biology, but also has been emphasized from the viewpoint of medical aspects such as development of antiviral vaccines. Isolation of a spontaneously emerging virus mutant strain takes a long time, and a desired mutant strain can be obtained only by chance.

HVJ (hemagglutinating virus of Japan; Sendai virus) is a virus belonging to the paramyxovirus family, having an envelope on the surface of which hemagglutinin and neuraminidase are present. HVJ has (−)-stranded RNA in the genome thereof; after infection of HVJ to host cells, (+)-stranded RNA is replicated from the (−) strand, from which a large amount of virus protein is produced, resulting in the formation of virus particles, which in turn bud to produce new virus particles. HVJ attracted attention as a fusogen for Ehrlich's tumor cells (Okada, Biken Journal, 1, p. 103-110, (1958)); the cell membrane fusion activity thereof (hereinafter, fusion activity) has been analyzed, and the utilization thereof as a gene introduction vector has been investigated. In the fusion, first, HN (hemagglutinating) protein recognizes acetyl-type sialic acid on the cell surface and decomposes the sugar chain thereof by the activity of sialidase, and then F (fusion) protein enters the lipid bilayer to induce the fusion. As such, HN protein possesses hemagglutination activity and hemolytic activity, and, when administered into the blood, causes a transient reduction in blood coagulation capacity. This virus has also been developed as a vector for gene transfection and drug delivery, but it is also anticipated that even if HVJ incorporating a target molecule is prepared, the specificity thereof will be lessened in the presence of HN protein.

Therefore, there is a demand for the development of a highly safe viral vector wherein the toxicity of receptor proteins such as HN protein has been ameliorated.

HVJ (hemagglutinating virus of Japan; Sendai virus) is also well known as a mouse parainfluenza virus that causes cell fusion; utilizing the function, gene transfection vectors such as recombinant Sendai viral vectors, HVJ envelope vectors, and HVJ-liposomes, and drug delivery systems, have been developed. In the fusion, HN (hemagglutinating) protein recognizes acetyl-type sialic acid on the cell surface, decomposes the sugar chain thereof by the activity of sialidase, and then F (fusion) protein enters the lipid bilayer to induce the fusion. Therefore, almost all cells having sialic acid can be subjects of the fusion. HVJ is highly versatile for a vector, but on the other hand it has no specificity and is not suitable for the introduction of cytotoxic molecules. One of the major problems to be solved in improving a vector is to enhance the specificity, specifically to enable target introduction. The present inventors' group has already succeeded in preparing liposomes using some lipids having an amino group, binding a chemically modified antibody molecule to the amino group using a crosslinking agent to prepare an immunoliposome, and fusing this liposome with inactivated HVJ to develop an HVJ-immunoliposome (Tomita, N et al, J. Gene Medicine, vol. 4, p. 527-535 (2002)). When an HVJ-immunoliposome prepared using a monoclonal antibody that recognizes the Thy-1 antigen of rat kidney mesangium cells was injected from a peripheral blood vessel, the HVJ-liposome, which otherwise gathers in the reticuloendothelial systems of the liver and spleen, accumulated in the mesangium of both kidneys, making it possible to introduce a fluorescent oligonucleic acid into 90% of the glomeruli. This fact suggests that even in the presence of HN protein, provided that a target molecule is inserted, and is first recognized and binds to a specific cell, fusion occurs there and enables specific introduction. However, the method of binding a protein like this antibody to a liposome is so complex that skills are required to obtain constant results.

Therefore, there is a demand for the development of a viral vector of high tissue and cell specificity, and a method of obtaining the viral vector conveniently and stably. For example, in Hallak et al., Cancer Res, vol. 65(12), p. 5292-5300 (2005), it is reported that in an attempt to fuse the M28L echistatin molecule, which binds to integrin $\alpha v\beta 3$, to the C-terminus of the H protein of measles virus, they modified the virus genome and prepared a virus that targets cancer cells having integrin $\alpha v\beta 3$. Furthermore, attempts have been made to modify various viral vectors to prepare targeting viral vectors (JP-T-2001-515493, JP-A-2002-320475, JP-T-2005-532075, JP-A-2002-330774).

DISCLOSURE OF THE INVENTION

It is a first object of the present invention to provide a modified paramyxovirus that can be utilized as a highly safe vector and a method of obtaining the modified paramyxovirus conveniently.

It is a second object of the present invention to provide a paramyxovirus vector capable of site-specific delivery of a drug and a new method of preparing the same.

The present inventors conducted diligent investigations to solve the above-described problems, and found that if the RNA of the HN protein of HVJ is knocked out with an siRNA, the virus produced while the suppressive effect thereof remains effective would lack HN protein, and that the virus lacking HN protein has reduced hemagglutination activity.

Furthermore, taking note of the fact that a fusion virus like Sendai virus incorporates the surface protein derived from the virus gene, expressed on the host cell membrane, upon release of virus particles outside the cell, the present inventors conceptualized that the host cell, rather than the virus genome, is modified to express the surface protein derived from the virus gene, having a targeting molecule in the extracellular domain thereof, on the cell membrane, the cell is infected with the virus, and virus particles are recovered. Hence, the present inventors prepared a cell incorporating a chimera gene comprising a gene that encodes the transmembrane domain of a fusion (F) protein of Sendai virus and a gene for a single-chain antibody fragment against a protein expressed in the epidermal basal layer, and found that when the cell was infected with the wild-type Sendai virus, a Sendai virus presenting a chimera F protein having the antigen binding capability of the antibody fragment on the virus surface was obtained.

Based on the findings above, the present inventors developed the present invention.

Accordingly, the present invention provides the followings.

[1] A modified paramyxovirus containing a reduced amount of a receptor-binding protein compared with the wild type.

[2] The virus according to [1], wherein the receptor-binding protein is HN protein and the paramyxovirus is HVJ.

[3] The virus according to [1] or [2], comprising a nucleic acid that suppresses the expression of a receptor-binding protein of a paramyxovirus.

[4] A virus envelope vector prepared from the virus according to [1] or [2].

[5] A method of preparing a modified paramyxovirus, comprising the steps:

(1) a step for introducing a nucleic acid that suppresses the expression of a receptor-binding protein of a paramyxovirus into an animal cell, (2) a step for infecting the paramyxovirus to the cell, and (3) a step for isolating paramyxovirus particles replicated in the cell.

[6] The method according to [5], wherein the nucleic acid that suppresses the expression of a receptor-binding protein of a paramyxovirus is an siRNA against the mRNA that encodes the protein.

[7] The method according to [5], wherein the paramyxovirus is HVJ.

[8] The method according to [7], wherein the receptor-binding protein is HN protein.

[9] The method according to [8], wherein the nucleic acid that suppresses the expression of the HN protein of HVJ is an siRNA against the HN mRNA of HVJ, consisting of a sequence selected from the group consisting of the nucleotide sequences shown by SEQ ID NOs:3, 4 and 5.

[10] A modified HVJ obtained by the method according to [5].

[11] An animal cell comprising a nucleic acid that suppresses the expression of a receptor-binding protein of a paramyxovirus.

[12] The animal cell according to [11], wherein the nucleic acid that suppresses the expression of a receptor-binding protein of a paramyxovirus is an siRNA against the HN mRNA of HVJ, consisting of a sequence selected from the group consisting of the nucleotide sequences shown by SEQ ID NOs:3, 4 and 5.

[13] An siRNA against the HN mRNA of HVJ, consisting of a sequence selected from the group consisting of the nucleotide sequences shown by SEQ ID NOs:3, 4 and 5.

[14] A chimera protein, wherein a peptide capable of binding specifically to a desired cell surface molecule is joined to the N-terminus side of the transmembrane domain of F protein derived from a paramyxovirus directly or via a peptide linker.

[15] The chimera protein according to [14], wherein a signal peptide selected from the group consisting of a signal peptide derived from F protein and signal peptides capable of functioning in mammalian cells is further added to the N-terminal side directly or via a linker peptide.

[16] The chimera protein according to [15], comprising the signal peptide derived from F protein, wherein the signal peptide consists of any one of the amino acid sequences (1) to (4) shown below:

(1) the amino acid sequence shown by amino acid numbers 1 to 25 in the amino acid sequence shown by SEQ ID NO:11, (2) the amino acid sequence shown by amino acid numbers 1 to 25 in the amino acid sequence shown by SEQ ID NO:11, having one or a plurality of amino acids substituted and/or deleted and/or inserted and/or added, and also having a function for a signal peptide, (3) the amino acid sequence shown by amino acid numbers 1 to 29 in the amino acid sequence shown by SEQ ID NO:11, (4) the amino acid sequence shown by amino acid numbers 1 to 29 in the amino acid sequence shown by SEQ ID NO:11, having one or a plurality of amino acids substituted and/or deleted and/or inserted and/or added, and also having a function for a signal peptide.

[17] The chimera protein according to [14], wherein the paramyxovirus is HVJ.

[18] The chimera protein according to [17], wherein the transmembrane domain of the HVJ-derived F protein consists of any one of the amino acid sequences (1) to (4) shown below:

(1) the amino acid sequence shown by amino acid numbers 490 to 565 in the amino acid sequence shown by SEQ ID NO:11, (2) the amino acid sequence shown by amino acid numbers 490 to 565 in the amino acid sequence shown by SEQ ID NO:11, having one or a plurality of amino acids substituted and/or deleted and/or inserted and/or added, and also having a function for a transmembrane domain, (3) the amino acid sequence shown by amino acid numbers 487 to 565 in the amino acid sequence shown by SEQ ID NO:11, (4) the amino acid sequence shown by amino acid numbers 487 to 565 in the amino acid sequence shown by SEQ ID NO:11, having one or a plurality of amino acids substituted and/or deleted and/or inserted and/or added, and also having a function for a transmembrane domain.

[19] The chimera protein according to [14], wherein the peptide that binds specifically to a cell surface molecule is a single-chain antibody against the molecule.

[20] The chimera protein according to [19], wherein the single-chain antibody is an antibody against desmoglein 3.

[21] The chimera protein according to [20], which is (1) or (2) shown below:

(1) the protein consisting of the amino acid sequence shown by SEQ ID NO:21, (2) a protein of the amino acid sequence shown by SEQ ID NO:21, having one or a plurality of amino acids substituted and/or deleted and/or inserted and/or added, and, if the signal peptide portion thereof is cleaved by processing and incorporated in virus particles, capable of being present on the particle surface thereof and binding to desmoglein 3.

[22] The chimera protein according to [14], wherein the peptide that binds specifically to the cell surface molecule is transferrin.

[23] The chimera protein according to [22], comprising the amino acid sequence (1) or (2) shown below:

(1) the amino acid sequence shown by amino acid numbers 40 to 797 in the amino acid sequence shown by SEQ ID NO:25, (2) the amino acid sequence shown by amino acid numbers 40 to 797 in the amino acid sequence shown by SEQ ID NO:25, having one or a plurality of amino acids substituted and/or deleted and/or inserted and/or added, and, if incorporated in virus particles, also having a function to be present on the particle surface thereof, to be expressed on the cell membrane, and to bind to the transferrin receptor.

[24] A nucleic acid that encodes the chimera protein according to any one of [14] to [23].

[25] The nucleic acid according to [24], consisting of the base sequence (1) or (2) below:

(1) the base sequence shown by SEQ ID NO:20, (2) a base sequence hybridizable with a complementary strand sequence of the base sequence shown by SEQ ID NO:20 under high-stringent conditions, and encoding a protein having a function for a transmembrane domain, and capable of binding to desmoglein 3.

[26] An animal cell comprising the nucleic acid according to [24] in an expressible form, and capable of expressing a peptide capable of binding specifically to a desired cell surface molecule in the chimera protein encoded by the nucleic acid on the cell surface.

[27] A modified paramyxovirus that presents a peptide capable of binding specifically to a desired cell surface molecule in the chimera protein according to [14] on the virus particle surface.

[28] The modified paramyxovirus according to [27], which is HVJ.

[29] The modified paramyxovirus according to [28], wherein HN protein is reduced or lacked compared with the wild type.

[30] A virus envelope vector prepared from the virus according to any one of [27] to [29].

[31] A method of preparing a tissue targeting paramyxovirus, comprising the steps (1) to (3) below:

(1) introducing a nucleic acid that encodes a chimera protein wherein a linker peptide consisting of 0 to 30 residues has been joined to the N-terminus side of the transmembrane domain of the F protein derived from paramyxovirus, and a peptide capable of binding specifically to a desired cell surface molecule has been joined to the N-terminus thereof, into a specified animal cell in a form allowing the expression of the chimera protein on the cell membrane of the cell, (2) infecting a paramyxovirus to the cell, (3) isolating paramyxovirus particles replicated in the cell.

[32] The method according to [31], wherein the nucleic acid is placed under the control of a promoter capable of functioning in an animal cell, and a nucleic acid that encodes a signal peptide capable of functioning in the cell is added thereto.

[33] The method according to [31], wherein the virus is HVJ.

Because a modified paramyxovirus of the present invention contains a reduced amount of receptor-binding protein and is capable of mitigating the adverse effects of the receptor-binding protein on target cells and the like, the paramyxovirus can be utilized as a highly safe vector. According to the method of the present invention of preparing a modified paramyxovirus, such a modified paramyxovirus can be obtained conveniently.

A paramyxovirus having a chimera protein of the present invention is highly specific for a particular tissue/cell, and is useful as a vector capable of site-specific delivery of a drug. It is also possible to obtain a still more specific viral vector by deleting a fusion-related protein of the virus, particularly a receptor-binding protein. According to the method of the present invention of preparing a targeting paramyxovirus, it is possible to obtain a paramyxovirus capable of targeting a desired tissue or cell conveniently and stably.

BEST MODE FOR CARRYING OUT THE INVENTION

Figure 1:
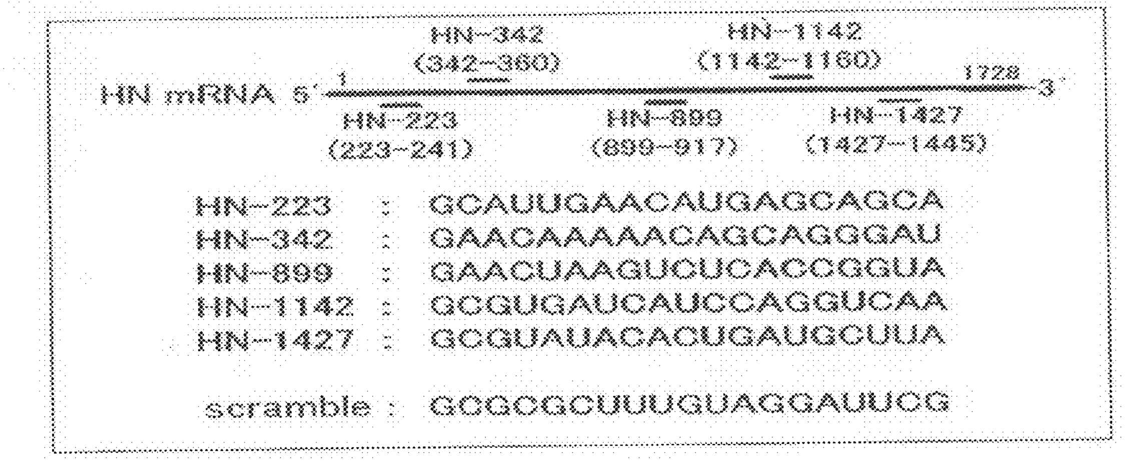
FIG. 1 shows the design of an siRNA against FIN mRNA. The five siRNAs for FIN mRNA knock down shown in FIG. 1 were designed and synthesized using SMART siRNA technology™ (Dharmacon Research). The five siRNAs (HN-223, HN-342, HN-899, HN-1142, HN-1427) target GCAUUGAACAUGAGCAGCA (223-241: SEQ ID NO:1), GAACAAAAACAGCAGGGAU (342-360: SEQ ID NO:2), GAACUAAGUCUCACCGGUA (899-917: SEQ ID NO:3), GCGUGAUCAUCCAGGUCAA (1142-1160: SEQ ID NO:4), and GCGUAUACACUGAUGCUUA (1427-1445: SEQ ID NO:5), respectively, on the HN mRNA. The scramble siRNA used as the control consists of a random sequence (GCGCGCUUUGUAGGAUUCG: SEQ ID NO:6).

1. Modified Paramyxovirus and Method of Preparing the Same

The present invention provides a modified paramyxovirus containing a reduced amount of receptor-binding protein compared with the wild type (hereinafter also referred to as the modified paramyxovirus I of the present invention).

Paramyxoviruses that can be used in the present invention include paramyxoviruses belonging to the paramyxovirus family, and having a receptor-binding protein. Paramyxoviruses having a receptor-binding protein include Sendai virus (HVJ), simian virus (SV), measles virus (MeV), respiratory syncytial virus (RSV), mumps virus (MuV), Newcastle disease virus and the like. Although paramyxoviruses that can be used in the present invention are not particularly limited, Sendai virus (HVJ) is preferable.

A receptor-binding protein refers to a protein involved in the binding to target cells; depending on the kind of paramyxovirus used, HN (hemagglutininating) protein, H protein, G protein and the like can be mentioned. In the present invention, the receptor-binding protein contained in a reduced amount is preferably HN protein. HN protein is known to possess hemagglutination activity, hemolytic activity and the like, and is thought to weaken the specificity of viruses.

In the modified paramyxovirus I of the present invention, the amount of receptor-binding protein has been reduced. A reduction in the amount of receptor-binding protein means that the expression level of the receptor-binding protein of the modified paramyxovirus I of the present invention has been reduced to at most about 0.6 times (for example, 0.5 times, preferably 0.3 times, more preferably 0.2 times, most preferably 0.1 times) or less, compared with that of the wild-type paramyxovirus. Preferably, in the modified paramyxovirus I of the present invention, no receptor-binding protein is expressed. The gene for the receptor-binding protein of the modified paramyxovirus I of the present invention may or may not have been mutated, as long as the expression level of the protein has been reduced. If the gene has been mutated, the mutation is not involved in the reduction in the amount of the receptor-binding protein.

In the modified paramyxovirus I of the present invention, it is preferable that by the containment of a nucleic acid that suppresses the expression of receptor-binding protein, the amount of receptor-binding protein has been reduced compared with the wild type. Examples of preferable nucleic acids that suppress the expression of receptor-binding protein include a variety of nucleic acids that can be introduced in the method of preparing the modified paramyxovirus I of the present invention described below.

In the modified paramyxovirus I of the present invention, the amount of receptor-binding protein has been reduced, so that the adverse effects of the receptor-binding protein on target cells and the like have been mitigated. Examples of the adverse effects of the receptor-binding protein on target cells include the hemagglutination activity and hemolytic activity of HN protein and the like. Therefore, the modified paramyxovirus I of the present invention can be utilized as a highly safe vector (virus envelope vector and the like).

When the modified paramyxovirus I of the present invention is used as a vector, to enhance the infectivity to target cells, a target molecule, such as a polypeptide, that binds specifically to a marker protein expressed on the target cell surface may be added to the virus.

Although the modified paramyxovirus I of the present invention may be prepared by combining any commonly known techniques, the following method is preferable.

Therefore, the present invention also provides a method of preparing a modified paramyxovirus I comprising the following steps (hereinafter also referred to as the method of the present invention):

(1) a step for introducing a nucleic acid that suppresses the expression of a receptor-binding protein of a paramyxovirus into an animal cell, (2) a step for infecting a paramyxovirus to the cell, and (3) a step for isolating paramyxovirus particles replicated in the cell.

In the above-described step (1), a nucleic acid that suppresses the expression of a receptor-binding protein of a paramyxovirus is supplied.

The paramyxovirus is as described above, and Sendai virus (HVJ) is preferable. The receptor-binding protein is as described above, and HN protein is preferable.

A preferred embodiment of a nucleic acid that suppresses the expression of a receptor-binding protein of a paramyxovirus is an antisense nucleic acid of the mRNA or initial transcription product of the receptor-binding protein of the paramyxovirus. "An antisense nucleic acid" refers to a nucleic acid consisting of a base sequence hybridizable with a target mRNA (initial transcription product) under physiological conditions for the cell that expresses the target mRNA (initial transcription product), and capable of inhibiting the translation of the polypeptide encoded by the target mRNA (initial transcription product) in the hybridized state. The kind of antisense nucleic acid may be DNA or RNA, or a DNA/RNA chimera. Also, because natural-type antisense nucleic acids have the phosphoric acid diester linkage thereof decomposed readily by nucleases being present in cells, the antisense nucleic acid of the present invention can also be synthesized using a modified nucleotide such as the thiophosphate type (phosphoric acid bond P═O replaced with P═S) or the 2'-O-methyl type, which are stable to nucleases. Other factors important for the design of an antisense nucleic acid include increases in the water solubility and cell membrane permeability and the like; these can also be achieved by improving dosage forms, such as the use of liposomes or microspheres.

The length of the antisense nucleic acid used in the present invention is not particularly limited, as long as the antisense nucleic acid is hybridizable specifically with the mRNA or initial transcription product of a receptor-binding protein of a paramyxovirus, and the antisense nucleic acid may be a sequence comprising a sequence complementary to about 15 bases at the shortest, or to the total sequence of the mRNA (initial transcription product) at the longest. Because of the ease of synthesis, the issue of antigenicity and the like, an oligonucleotide consisting of about 15 to about 30 bases is preferable. When the antisense nucleic acid is an about 25-mer oligo-DNA, the base sequence hybridizable with the mRNA of a receptor-binding protein of a paramyxovirus under physiological conditions may normally have a homology of about 80% or more, though the choice thereof varies depending on the base composition of the target sequence.

The target sequence for the antisense nucleic acid of the present invention is not particularly limited, as long as it is a sequence that inhibits the translation of a receptor-binding protein of a paramyxovirus or a functional fragment thereof when hybridized by the antisense nucleic acid; the target sequence may be the total sequence, or a partial sequence, of the mRNA of a receptor-binding protein of a paramyxovirus, or may be the intron portion of the initial transcription product; when an oligonucleotide is used as the antisense nucleic acid, the target sequence is desirably located between the 5'-terminus of the mRNA of a receptor-binding protein of a paramyxovirus and the C-terminus coding site of the coding region. Preferably, the target sequence is the region between the 5'-terminus and the N-terminus coding site of the coding region, most preferably a base sequence in the vicinity of the initiation codon. It is preferable to choose a target sequence wherein an antisense nucleic acid complementary thereto will not form a secondary structure such as a hairpin structure.

Another preferred embodiment of a nucleic acid that suppresses the expression of a receptor-binding protein of a paramyxovirus is a ribozyme capable of specifically cleaving the mRNA or initial transcription product of a receptor-binding protein of a paramyxovirus in the coding region (including the intron portion in case of the initial transcription product). "A ribozyme" refers to an RNA possessing an enzyme activity to cleave nucleic acids, and this term is herein used as a concept encompassing DNA, as long as it possesses sequence-specific nucleic acid cleavage activity, since it has recently been found that an oligo DNA having the base sequence of the enzyme activity site also possesses nucleic acid cleavage activity. One of the most versatile ribozymes is self-splicing RNA found in infectious RNAs such as viroid and virusoid, and the hammerhead type, the hairpin type and the like are known. The hammerhead type exhibits enzyme activity with about 40 bases; it is possible to cleave the target mRNA specifically by making several bases at both ends adjoining to the portion assuming a hammerhead structure (about 10 bases in total) to be a sequence complementary to the desired cleavage site of the mRNA. Because this type of ribozyme has RNA as the only substrate, it offers the additional advantage of not attacking genomic DNA. If the mRNA of a receptor-binding protein of a paramyxovirus assumes a double-stranded structure per se, the target sequence can be made single-stranded by using a hybrid ribozyme joined with an RNA motif derived from a viral nucleic acid, capable of binding specifically to RNA helicase [Proc. Natl. Acad. Sci. USA, 98(10): 5572-5577 (2001)]. Furthermore, when a ribozyme is used in the form of an expression vector comprising the DNA that encodes the same, the ribozyme can also be made to be a hybrid ribozyme further joined with a sequence of modified tRNA, in order to promote the transfer to cytoplasm [Nucleic Acids Res., 29(13): 2780-2788 (2001)].

Still another embodiment of a substance that suppresses the expression of a receptor-binding protein of a paramyxovirus is an oligo-RNA complementary to a partial sequence (including the intron portion in case of the initial transcription product) in the coding region of the mRNA or initial transcription product of a receptor-binding protein of a paramyxovirus, what is called an siRNA. What is called RNA interference (RNAi), the phenomenon in which introducing a short double-stranded RNA into cells leads to the degradation of the mRNA complementary to the RNA, has been known to occur in nematodes, insects, plants and the like; since this phenomenon was recently found to occur in animal cells as well [*Nature,* 411(6836): 494-498 (2001)], it has been commonly used as an alternative to ribozymes. An siRNA can be designed as appropriate on the basis of the base sequence information on the mRNA for the target using a commercially available software program (e.g., RNAi Designer; Invitrogen).

Although an siRNA synthesized in-house as described below can be used, a commercially available one may be used.

Antisense oligonucleotides and ribozymes used in the present invention can be prepared by determining the target sequence of the mRNA or initial transcription product on the basis of the DNA sequence or genomic DNA sequence of a receptor-binding protein of a paramyxovirus, and synthesizing a sequence complementary thereto using a commercially available DNA/RNA synthesizer (Applied Biosystems, Beckman, etc.). An siRNA can be prepared by synthesizing a sense strand and an antisense strand using a DNA/RNA synthesizer, respectively, denaturing the strands in an appropriate annealing buffer solution at about 90 to about 95° C. for about 1 minute, and then annealing the same at about 30 to about 70° C. for about 1 to about 8 hours. A longer double-stranded polynucleotide can be prepared by synthesizing complementary oligonucleotide chains to overlap alternately, annealing them, and then ligating them with ligase. Alternatively, an siRNA can be designed to be processed by a dicer and the like in the animal cell to be transfected, by synthesizing an RNA wherein a sense strand and an antisense strand have been joined via a linker of an appropriate length (for example, about 3 to about 10 bases). Furthermore, an expression vector wherein the DNAs that encode a sense strand and an antisense strand are placed under the control of separate Pol III system promoters such as U6 and H1, respectively, or an expression vector wherein the DNA that encodes the above-described RNA strand wherein a sense strand and an antisense strand have been joined via a linker are placed under the control of Pol III system promoter, may be prepared and allowed to be expressed in an animal cell to form an siRNA.

Preferably, the nucleic acid that suppresses the expression of a receptor-binding protein of a paramyxovirus is an siRNA against the mRNA of a receptor-binding protein of a paramyxovirus. More preferably, the nucleic acid is an siRNA against the mRNA of the HN protein of HVJ. Specifically, the siRNA preferably consists of the sequence shown by HN-899 (SEQ ID NO:3), HN-1142 (SEQ ID NO:4) or HN-1427 (SEQ ID NO:5).

Although the animal cell to which the nucleic acid is introduced can be a cell derived from an optionally chosen animal, as long as a paramyxovirus infects the same and reconstitute paramyxovirus particles in the cell, a cell derived from a mammal is preferable. As used herein, the term "mammal" includes, for example, but is not limited to, primates, laboratory animals, domestic animals, companion animals and the like; specifically, human, monkey, rat, mouse, guinea pig, rabbit, horse, bovine, goat, sheep, dog, cat and the like can be mentioned. Specifically, cultured cells such as monkey kidney-derived CV-1 cells and LLC-MK2 cells and hamster kidney-derived BHK cells, and the like can be mentioned.

A method of introducing the nucleic acid into an animal cell can be chosen as appropriate according to the kind of the cell. Examples include lipofection, microinjection, calcium phosphate co-precipitation, PEG method, electroporation and the like.

In the above-described step (2), a paramyxovirus is infected to an animal cell incorporating a nucleic acid that suppresses the expression of the receptor-binding protein of the paramyxovirus.

The paramyxovirus to be infected is not particularly limited, as long as it has the capability of reconstitution, whether a wild-type paramyxovirus or a modified paramyxovirus. In the case of a modified paramyxovirus, the modification is not involved in the reduction in the amount of receptor-binding protein.

The infected paramyxovirus reconstitutes itself as a paramyxovirus with reduced expression of receptor-binding protein in animal cells.

Isolation of replicated paramyxovirus particles is achieved by a method known per se, for example, recovery and centrifugation of the cell culture supernatant, and the like.

The modified paramyxovirus thus prepared has reduced expression of receptor-binding protein. A reduction in the amount of receptor-binding protein means that the expression level of the receptor-binding protein of the modified paramyxovirus obtained by the method of the present invention has been reduced to at most about 0.6 times (e.g., 0.5 times, preferably 0.3 times, more preferably 0.2 times, particularly preferably 0.1 times) or lower, compared with that of the wild-type paramyxovirus. Most preferably, no receptor-binding protein is expressed in the modified paramyxovirus obtained by the method of the present invention.

Because the modified paramyxovirus obtained by the method of the present invention has a reduced amount of receptor-binding protein, the adverse effects of the receptor-binding protein on target cells and the like have been mitigated. Particularly, the modified paramyxovirus of the present invention has reduced hemagglutination activity; therefore, hemagglutination is less likely to occur when the modified paramyxovirus of the present invention is administered to a living organism than when the wild-type paramyxovirus is administered.

Therefore, the modified paramyxovirus I of the present invention can be utilized as a highly safe vector (virus envelope vector and the like).

2. Chimera Protein and Nucleic Acid Encoding the Same

A chimera protein used in the present invention is a chimera protein comprising the transmembrane domain of a surface protein derived from a paramyxovirus and a peptide capable of binding specifically to a desired cell surface molecule. The surface protein derived from a paramyxovirus is exemplified by receptor-binding proteins and fusion (F) proteins derived from a paramyxovirus (hereinafter, these are sometimes generically referred to as a fusion-related protein) and the like; F protein is more preferable, and the F protein derived from Sendai virus (HVJ) is particularly preferable. For example, the transmembrane domain of an HVJ-derived F protein is a partial sequence of the amino acid sequence shown by SEQ ID NO:11, comprising the amino acid sequence shown by amino acid numbers 490 to 565, the amino acid sequence shown by amino acid numbers 487 to 565, or the transmembrane site shown by amino acid numbers 501 to 521 (see UniProtKB/Swiss-Prot entry, Primary accession number: P04855). As used herein, the term "transmembrane domain" means a functional portion of a virus surface protein, comprising a transmembrane site, and further comprising a sequence in the vicinity of the site required for interaction with the lining protein of a paramyxovirus and incorporation in the virus particle surface. By containing a transmembrane site, the chimera protein expressed in an animal cell and transported to the cell membrane stays on the cell membrane in a state wherein the extramembrane region of the membrane protein (herein, the region of the virus surface protein exposed outside the virus particles is referred to as the extramembrane region) is presented outside the cell. Examples of preferable transmembrane domains used in the present invention are peptides consisting of the amino acid sequence shown by amino acid numbers 490 to 565 in the amino acid sequence shown by SEQ ID NO:11 or substantially the same sequence thereas, which are transmembrane domains of an HVJ-derived F protein. Other examples of preferable transmembrane domains used in the present invention are peptides consisting of the amino acid sequence shown by amino acid numbers 487 to 565 in the amino acid sequence shown by SEQ ID NO:11 or substantially the same sequence thereas, which are transmembrane domains of an HVJ-derived F protein. Here, "substantially the same sequence" has the same meaning as that described below with respect to the full-length of HVJ-derived F protein. Specifically, peptides of the amino acid sequence shown by amino acid numbers 490 to 565 or amino acid numbers 487 to 565 in the amino acid sequence shown by SEQ ID NO:11, having one or a plurality (for example, 1 to 10, preferably 1 to 5, 4, 3 or 2) of amino acids substituted and/or deleted and/or inserted and/or added, and retaining the capability of interacting with the lining protein of a paramyxovirus, and incorporation in the virus particle surface, are also included in the transmembrane domains of an HVJ-derived F protein.

A chimera protein used in the present invention comprises as a portion thereof a peptide capable of binding specifically to a desired cell surface molecule. Here, "a desired cell surface molecule" means a molecule that is present on the cell surface to be targeted by a modified paramyxovirus of the present invention described below. The cell surface molecule is not particularly limited, as long as it is expressed on the surface of the cell targeted by a modified paramyxovirus of the present invention; any commonly known cell surface proteins, sugar chains, lipids and the like are all included. Preferably, the cell surface molecule is a cell surface protein being expressed specifically in a particular type of cell. Examples of preferable cell surface molecules include, but are not limited to, desmoglein 3 (expressed in epidermal basal cells), β2 integrin (expressed in neutrophils and macrophage), α4 integrin (expressed in lymphocytes and fibroblasts), αIIbβ3 integrin (expressed in platelets and megakaryocytes), folic acid receptor (expressed in cancer cells), transferrin receptor (expressed in cancer cells), HER2 (expressed in metastatic breast cancer cells), EGFR (expressed in non-small-cell lung cancer cells), LDLR (expressed in hepatocytes), CD20 (expressed in malignant lymphoma), CEA (expressed in pancreatic cancer), Gp100 (expressed in melanoma), PSMA (expressed in prostatic cancer), AFP (expressed in primary liver cancer and yolk sac tumor) and the like. Desmoglein 3 or transferrin receptor is preferable.

Examples of peptides capable of binding specifically to a cell surface molecule include ligands for various cell surface receptors, for example, peptides having an RGD sequence for integrins (e.g., echistatin, fibronectin and the like), transferrin for transferrin receptors and the like, or antibodies against various cell surface molecules (for example, antibody molecules that can be encoded by single nucleic acids, such as single-chain antibodies, are preferable) and the like. For example, when the cell surface molecule is desmoglein 3, a peptide capable of binding specifically to the cell surface molecule is a single-chain antibody that recognizes desmoglein 3 (scFv).

A peptide capable of binding specifically to a cell surface molecule is added to the N-terminus of the transmembrane domain of the above-described surface protein. The peptide may be added to the N-terminus of the transmembrane domain via a peptide linker. The peptide linker may be a peptide of an optionally chosen length consisting of optionally chosen amino acid residues, and may comprise, or consist of, an amino acid sequence intrinsically present on the N-terminus side of the transmembrane domain of the surface protein used. Preferably, the peptide linker is 1 to 30 residues, more preferably 1 to 25, 1 to 20, 1 to 15 or 1 to 10 residues, and most preferably 1 to 5 residues, in length. This linker is sometimes inserted to join in frame the base sequences of the gene that encodes the transmembrane domain and the gene that encodes a peptide capable of binding specifically to the cell surface molecule, by a person skilled in the art.

A chimera protein used in the present invention is desirably expressed, to prepare a modified paramyxovirus that presents the chimera protein on the virus particle surface thereof, in a form that can be transported to the cell membrane of a specified animal cell that can be used as the host cell for the replication of the virus. Therefore, the chimera protein preferably comprises a signal peptide derived from a virus surface protein that constitutes the chimera protein, preferably a signal peptide derived from F protein, at the N-terminus thereof, or has another signal peptide capable of functioning in the specified mammalian cell added thereto. As required, the signal peptide can comprise a peptide linker as described above, preferably at the C-terminus thereof. The peptide linker may be a peptide of an optionally chosen length consisting of optionally chosen amino acid residues, and may be one comprising, or consisting of, an amino acid sequence intrinsically present on the C-terminus side of the intrinsic signal peptide of F protein, i.e., the sequence of an N-terminus portion of mature F protein. Preferably, the peptide linker is 1 to 30 residues, more preferably 1 to 25, 1 to 20, 1 to 15 or 1 to 10 residues, and most preferably 1 to 5 residues, in length. Signal peptides of commonly known surface proteins are published on a number of protein databases, and can easily be predicted on the basis of the amino acid sequence of the protein by, for example, the method of Kyte & Doolittle and the like (a large number of such analytical software programs are commercially available, and are commonly utilizable on websites). For example, the signal peptide of HVJ-derived F protein is the region shown by amino acid numbers 1 to 25 in the amino acid sequence shown by SEQ ID NO:11 (see UniProtKB/Swiss-Prot entry, Primary accession number: P04855); a chimera protein of the present invention preferably comprises at least the region; ones comprising on the N-terminus side thereof the region shown by amino acid numbers 1 to 25, 1 to 26, 1 to 27, 1 to 28, 1 to 29, 1 to 30 or 1 to 35 in the amino acid sequence shown by SEQ ID NO:11 and the like can be mentioned. Peptides of the amino acid sequence shown by amino acid numbers 1 to 25 or amino acid numbers 1 to 29 in the amino acid sequence shown by SEQ ID NO:11, having one or a plurality (for example, 1 to 10, preferably 1 to 5, 4, 3 or 2) of amino acids substituted and/or deleted and/or inserted and/or added, and consisting of an amino acid sequence capable of functioning as a signal peptide in a specified mammalian cell, are also included in the signal peptide of the HVJ-derived F protein.

Examples of other useful signal peptides capable of functioning in specified mammalian cells include, but are not limited to, the α-amylase signal sequence, subtilisin signal sequence, MFα signal sequence, SUC2 signal sequence, insulin signal sequence, α-interferon signal sequence, antibody molecule signal sequence and the like.

A chimera protein of the present invention may comprise the amino acid sequence of a tag that facilitates the detection, purification and the like of the protein. Tags include Flag tags, Hisx6 tags, c-Myc tags, HA tags, AU1 tags, GST tags, MBP tags, fluorescent protein tags (for example, GFP, YFP, RFP, CFP, BFP and the like), immunoglobulin, Fc tags and the like. The position of the tag is not particularly limited, as long as a chimera protein of the present invention functions as a transmembrane domain, and is capable of binding specifically to a desired cell surface molecule; preferably, the position is the C-terminus of the chimera protein or the C-terminus of the signal peptide.

In a preferred embodiment, a chimera protein used in the present invention comprises the transmembrane domain of a fusion-related protein derived from a fusion virus like a paramyxovirus. Here, “a fusion-related protein” is not particularly limited, as long as it is a protein expressed on the surface of the fusion virus, and related to fusion of the virus and the target cell; examples include F protein and receptor-binding proteins (HN protein, H protein, G protein and the like).

In a particularly preferred embodiment, the present invention provides a chimera protein wherein a peptide capable of binding specifically to a desired cell surface molecule has been joined to the N-terminus side of the transmembrane domain of the F protein derived from a paramyxovirus directly or via a peptide linker. The paramyxovirus is not particularly limited, as long as it is a virus belonging to the paramyxovirus family, and infecting a host cell via fusion with the cell; examples include, but are not limited to, Sendai virus (HVJ), measles virus (MV), mumps virus (MuV), parainfluenza virus 1 (PIV1), PIV2, PIV3, simian virus 5 (SV5), Newcastle virus (NDV), RS virus (RSV) and the like.

Preferably, the fusion-related protein derived from a paramyxovirus is the HVJ-derived F protein. The HVJ-derived F protein is a protein consisting of the same or substantially the same amino acid sequence as the amino acid sequence shown by SEQ ID NO:11. “A protein consisting of the same or substantially the same amino acid sequence as the amino acid sequence shown by SEQ ID NO:11” is a protein consisting of an amino acid sequence having a homology of about 70% or more, preferably about 80% or more, more preferably about 90% or more, still more preferably about 95% or more, to the amino acid sequence shown by SEQ ID NO:11, and having an activity mediating fusion of the virus and the cell.

Amino acid sequence homology can be calculated using the homology calculation algorithm NCBI BLAST (National Center for Biotechnology Information Basic Local Alignment Search Tool) under the following conditions (expectancy=10; gap allowed; matrix=BLOSUM62; filtering=OFF).

HVJ-derived F protein also include, for example, proteins having (i) the amino acid sequence shown by SEQ ID NO:11 wherein 1 to 20 (preferably 1 to 15, more preferably 1 to 5, still more preferably 1 to 3) amino acids have been deleted, (ii) the amino acid sequence shown by SEQ ID NO:11 wherein 1 to 20 (preferably 1 to 15, more preferably 1 to 5, still more preferably 1 to 3) amino acids have been added, (iii) the amino acid sequence shown by SEQ ID NO:11 wherein 1 to 20 (preferably 1 to 15, more preferably 1 to 5, still more preferably 1 to 3) amino acids have been inserted, (iv) the amino acid sequence shown by SEQ ID NO:11 wherein 1 to 20 (preferably 1 to 15, more preferably 1 to 5, still more preferably 1 to 3) amino acids have been substituted by other amino acids, or (v) an amino acid sequence combining these deletions, additions, insertions, and substitutions.

When an amino acid sequence has been deleted, added, inserted or substituted as described above, the position of the deletion, addition, insertion or substitution is not particularly limited. Commonly known variants include, but are not limited to, one shown by UniProtKB/Swiss-Prot entry, Primary accession number: P04855.

The transmembrane domain of an HVJ-derived F protein may be any one, as long as it comprises the transmembrane site thereof (the region shown by amino acid numbers 501 to 521 in the amino acid sequence shown by SEQ ID NO:11) and a sequence in the vicinity thereof required for interaction with the lining protein of HVJ and incorporation in the virus particle surface. Because a modified paramyxovirus of the present invention described below expresses an intact F protein derived from the virus genome on the virus particle surface thereof, the chimera F protein of the present invention does not need to comprise the fusion peptide (the region shown by amino acid numbers 117 to 141 in the amino acid sequence shown by SEQ ID NO:11). Particularly preferably, the transmembrane domain of an HVJ-derived F protein used in the chimera F protein of the present invention consists of the same or substantially the same amino acid sequence as the amino acid sequence shown by amino acid numbers 490 to 565 or amino acid numbers 487 to 565 in the amino acid sequence shown by SEQ ID NO:11. Here, “substantially the same” is as defined above.

The peptide capable of binding specifically to a cell surface molecule, contained in the chimera F protein of the present invention, is not particularly limited, and those described above can be used; for example, in a preferred embodiment, the chimera F protein of the present invention comprises an anti-desmoglein 3 single-chain antibody. The antibody is desirably a chimera antibody, more preferably a humanized antibody, most preferably a complete human antibody, considering the fact that the modified paramyxovirus II of the present invention is preferably utilized as a vector for gene transfer to humans. The antibody polypeptide can be joined to the transmembrane domain of an HVJ-derived F protein. In a particularly preferred embodiment, the anti-desmoglein 3 single-chain antibody polypeptide is inserted between the signal peptide and the transmembrane domain of the F protein, in place of the F2 and F1 regions of the HVJ-derived F protein, more specifically, the amino acid sequence shown by amino acid numbers 30 to 489 in the amino acid sequence shown by SEQ ID NO:11.

In another preferred embodiment, the chimera F protein of the present invention comprises transferrin. The antibody is desirably human transferrin, considering the fact that the modified paramyxovirus II of the present invention is preferably utilized as a vector for gene transfer to humans. Transferrin can be joined to the transmembrane domain of the HVJ-derived F protein. In a particularly preferred embodiment, transferrin is inserted between the signal peptide and the transmembrane domain of the F protein, in place of the F2 and F1 regions of the HVJ-derived F protein, more specifically the amino acid sequence shown by amino acid numbers 30 to 486 in the amino acid sequence shown by SEQ ID NO:11.

An example of the chimera protein of the present invention is a protein consisting of the same or substantially the same amino acid sequence as the amino acid sequence shown by SEQ ID NO:21, which is a chimera protein comprising an HVJ-derived F protein fragment. Here, “substantially the same” is as defined above; the protein consisting of substantially the same sequence needs to retain the capability of specifically recognizing desmoglein 3 and binding thereto, in addition to being incorporatable in the HVJ particle surface.

This protein comprises a single-chain antibody variable fragment (scFv) that recognizes desmoglein 3 in the extramembrane region thereof; a virus having such a protein is capable of specifically targeting a cell presenting desmoglein 3 on the cell surface thereof. Because desmoglein 3 is expressed selectively in the cells of the epidermal basal layer, the above-described virus specifically targets the epidermal basal layer.

Another example of the chimera protein of the present invention is a protein consisting of the amino acid sequence shown by SEQ ID NO:25 or the same or substantially the same sequence as the amino acid sequence shown by amino acid numbers 40 to 797 in the amino acid sequence shown by SEQ ID NO:25, which is a chimera protein comprising an F protein fragment derived from HVJ. Here, "substantially the same" is as defined above; the protein consisting of substantially the same sequence needs to retain the capability of specifically recognizing a transferrin receptor and binding thereto, in addition to being incorporatable in the HVJ particle surface. This protein comprises transferrin in the extramembrane region thereof; a virus having such a protein is capable of specifically targeting a cell presenting a transferrin receptor on the cell surface thereof. Because a transferrin receptor is expressed selectively in cancer cells, the above-described virus specifically targets cancer cells.

For the purpose of producing a modified paramyxovirus of the present invention, the chimera protein used in the present invention needs to be expressed on the cell membrane of an animal cell allowing the infection of a paramyxovirus and replication of the virus. Therefore, preferably, the chimera protein is produced by introducing a nucleic acid that encodes the chimera protein in an expressible form into the animal cell. Accordingly, the present invention also provides a nucleic acid that encodes a chimera protein used in the present invention (hereinafter also simply referred to as "the chimera nucleic acid of the present invention").

The chimera nucleic acid of the present invention may be DNA or RNA or a chimera of both. The chimera nucleic acid may be single-stranded or double-stranded. In the case of a double strand, the chimera nucleic acid may be double-stranded DNA or double-stranded RNA, or a DNA/RNA hybrid.

The chimera nucleic acid of the present invention comprises a natural base sequence that encodes a peptide portion derived from a surface protein and a peptide portion capable of binding specifically to a cell surface molecule, or ones encoded by different codons, and joined as arranged, or a base sequence that hybridizes with a nucleic acid consisting of a base sequence complementary to the joined sequence under high stringent conditions, and encodes a protein retaining the same quality of activity as the chimera protein (that is, an activity to allow the expression in the animal cell transfected with the chimera nucleic acid, transportation onto the cell membrane, incorporation into the virus particle surface upon the extracellular release of paramyxovirus particles replicated and reconstituted in the cell, and targeting of the resulting modified paramyxovirus to a target cell that expresses a desired cell surface molecule).

Useful base sequences that hybridize under high-stringent conditions include, for example, a base sequence having a homology of about 70% or more, preferably about 80% or more, more preferably about 90% or more, particularly preferably about 95% or more, to the joined sequence, and the like. Base sequence homology in the present description can be calculated using the homology calculation algorithm NCBI BLAST (National Center for Biotechnology Information Basic Local Alignment Search Tool) under the following conditions (expectancy=10; gap allowed; filtering=ON; match score=1; mismatch score=−3).

Conditions for the above-described hybridization can be established with reference to published conditions (Current Protocols in Molecular Biology, John Wiley & Sons, 6.3.1-6.3.6, 1999). For example, as conditions for hybridization under high stringent conditions, 6×SSC (sodium chloride/sodium citrate)/45° C. followed by not less than one time of washing with 0.2×SSC/0.1% SDS/50 to 65° C. can be mentioned. As examples of conditions for hybridization under moderate stringent conditions, 2×SSC/30° C. followed by not less than one time of washing with 1×SSC/0.1% SDS/30 to 50° C. can be mentioned.

A particularly preferred example of the chimera nucleic acid of the present invention is nucleic acids that encode the above-described protein consisting of the same or substantially the same amino acid sequence as the amino acid sequence shown by SEQ ID NO:21. More preferably, the chimera nucleic acid is a nucleic acid consisting of the base sequence shown by SEQ ID NO:20, or a nucleic acid comprising a base sequence capable of hybridizing with a complementary strand sequence of the base sequence shown by SEQ ID NO:20 under stringent conditions, and encoding a protein retaining the capability of specifically recognizing desmoglein 3 and binding thereto, in addition to being incorporatable in the HVJ particle surface. Here, high stringent conditions are as defined above.

Another particularly preferred example of the chimera nucleic acid of the present invention is nucleic acids that encode the above-described protein consisting of the amino acid sequence shown by SEQ ID NO:25 or the same or substantially the same amino acid sequence as the amino acid sequence shown by amino acid numbers 40 to 797 in the amino acid sequence shown by SEQ ID NO:25. More preferably, the chimera nucleic acid is a nucleic acid comprising the base sequence shown by SEQ ID NO:24 or the base sequence shown by base numbers 118 to 2391 in the base sequence shown by SEQ ID NO:24, or a nucleic acid comprising a base sequence capable of hybridizing with a complementary strand sequence of the base sequence shown by SEQ ID NO:24 or the base sequence shown by base numbers 118 to 2391 in the base sequence shown by SEQ ID NO:24, and encoding a protein retaining the capability of specifically recognizing a transferrin receptor and binding thereto, in addition to being incorporatable in the HVJ particle surface. Here, high-stringent conditions are as defined above.

Hereinafter, a method of preparing a chimera nucleic acid that encodes a chimera protein of a single-chain antibody and a surface protein or a fragment thereof, which is a preferred embodiment of the present invention, is described; those skilled in the art can easily produce a nucleic acid that encodes another chimera protein by combining as appropriate the techniques described below and techniques that are obvious and commonly used in the art.

First, on the basis of commonly known sequence information on nucleic acids that encode surface proteins, a nucleic acid that encodes the transmembrane domain of the surface protein is cloned by a conventional method. For example, the nucleic acid can be cloned by PCR amplification using a synthetic DNA primer having a portion of the base sequence that encodes the transmembrane domain of the surface protein, or by hybridizing a nucleic acid incorporated in an appropriate expression vector with a labeled DNA fragment or synthetic DNA that encodes a portion or the entire region of the surface protein. Hybridization can be performed by, for example, a method described in Molecular Cloning, 2nd edition (mentioned above) and the like. When a commercially available library is used, hybridization can be performed by the method described in the instruction manual attached to the library.

The nucleic acid obtained that encodes the transmembrane domain of the surface protein can have an appropriate restriction endonuclease site introduced thereinto using a linker, site-directed mutagenesis and the like as required, to facilitate the subsequent preparation of a chimera nucleic acid.

Examples of methods of obtaining a nucleic acid that encodes a single-chain antibody include, but are not limited to, a method wherein a monoclonal antibody producing hybridoma is prepared with a desired cell surface molecule or a fragment thereof as the antigen by a conventional method (here, using a human antibody-producing mouse such as KM Mouse™ as the animal to be immunized, a human antibody-producing hybridoma can easily be obtained), RNA is extracted from the hybridoma, and the variable region gene is cloned by RT-PCR using primers specific for the respective variable regions of the heavy chain and light chain of a human antibody, after which the heavy chain and light chain are joined via an appropriate linker, and the like. In the process of PCR, to a terminus of the nucleic acid that encodes the single-chain antibody, a restriction endonuclease site suitable for ligation with a nucleic acid that encodes a surface protein or signal peptide can be introduced.

The nucleic acid obtained that encodes the surface protein and the nucleic acid obtained that encodes the single-chain antibody can be joined using an appropriate restriction endonuclease, ligase and the like.

The chimera nucleic acid of the present invention preferably has a nucleic acid that encodes one of the above-described signal peptides joined thereto, preferably to the 5'-terminus thereof, so that the chimera protein encoded by the chimera nucleic acid will be transported onto the cell membrane along the secretion route in a specified animal cell. Although such a nucleic acid that encodes a signal peptide can be cloned by, for example, PCR with a genomic nucleic acid or cDNA extracted from a cell (including virus) that expresses a protein comprising the signal peptide as the template, the same can also be chemically synthesized on the basis of commonly known base sequence information.

The nucleic acid obtained that encodes a signal peptide can be joined with a nucleic acid that encodes a single-chain antibody or a nucleic acid that encodes a surface protein using an appropriate restriction endonuclease, ligase and the like.

By introducing the chimera nucleic acid of the present invention into an animal cell, an animal cell that expresses the chimera protein of the present invention on the cell membrane can be obtained.

It is also possible to obtain a modified paramyxovirus expressing the chimera protein of the present invention on the virus particle surface thereof (the modified paramyxovirus II of the present invention) by infecting the above-described animal cell with a paramyxovirus.

The modified paramyxovirus II of the present invention is expressing on the virus surface thereof a chimera protein wherein a virus surface protein has been joined to a peptide that binds specifically to a cell surface molecule of a target cell. Therefore, the modified paramyxovirus is highly specific for target tissues/cells, and can be utilized as a paramyxovirus vector (virus envelope vector and the like) capable of site-specific delivery of a drug and the like.

Furthermore, by modifying the modified paramyxovirus II in the same manner as the modified paramyxovirus I of the present invention described above, it is possible to obtain a modified paramyxovirus wherein:

(1) a chimera protein wherein a peptide capable of binding specifically to a desired cell surface molecule is joined to the N-terminus side of the transmembrane domain of an F protein derived from a paramyxovirus directly or via a peptide linker is presented on the virus particle surface thereof, and (2) the amount of receptor-binding protein (HN protein and the like) contained has been reduced compared with the wild type. Here, "a peptide capable of binding specifically to a cell surface molecule" differs from "a receptor-binding protein". This modified paramyxovirus is highly preferable because high safety has been achieved as the adverse effects of the receptor-binding protein on target cells have been mitigated, and also because high specificity for a particular tissue/cell has been achieved.

3. Method of Preparing Targeting Paramyxovirus

The present invention provides a method of preparing a targeting paramyxovirus, comprising the following steps (hereinafter also referred to as the method of the present invention):

(1) a step for introducing a nucleic acid that encodes a chimera protein having a linker peptide consisting of 0 to 30 residues joined on the N-terminus side of the transmembrane domain of an F protein derived from a paramyxovirus, and also having a peptide capable of binding specifically to a desired cell surface molecule joined to the N-terminus thereof, into the cell in a form allowing the expression of the chimera protein on the cell membrane of a specified animal cell, (2) a step for infecting a paramyxovirus to the cell, and (3) a step for isolating paramyxovirus particles replicated in the cell.

In the step (1), the above-described chimera nucleic acid of the present invention is prepared in a form expressible in an animal cell, and introduced. Specifically, the chimera nucleic acid of the present invention prepared as described above is incorporated into an appropriate expression vector.

The expression vector is not particularly limited, as long as it is capable of producing the chimera protein of the present invention in animal cells. Examples include plasmid vectors, viral vectors (for example, adenovirus, retrovirus) and the like. It is preferable that the expression vector comprise at least a promoter, an initiation codon, the chimera nucleic acid of the present invention, and a stop codon. The expression vector may also comprise an enhancer sequence, the non-translational regions on the 5' side and 3' side of the nucleic acid of the present invention, a splicing junction, a polyadenylation site, a selection marker region or a replicable unit, and the like. A gene amplification gene (marker) in common use may be contained according to the intended use. Promoters include SV40-derived promoter, retrovirus promoter, heat shock promoter and the like.

The terminator region, replicable unit, enhancer sequence, polyadenylation site and splicing junction site used may be those known per se.

The selection marker used may be one known per se. Examples include antibiotic-resistant genes such as tetracycline, ampicillin, kanamycin and the like.

Examples of the gene amplification gene include the dihydrofolate reductase (DHFR) gene, thymidine kinase gene, neomycin resistance gene, glutamate synthase gene, adenosine deaminase gene, ornithine decarboxylase gene, hygromycin-B-phosphotransferase gene, asparlate transcarbamylase gene and the like.

A nucleic acid of the present invention is prepared in a form expressible in an animal cell by being joined downstream of a promoter in an appropriate expression vector using ordinary gene engineering techniques.

The animal cell is not particularly limited, as long as it expresses the above-described nucleic acid, and the paramyxovirus is reconstituted in the cell. Examples include cultured cells such as monkey kidney-derived CV-1 cells and LLC-MK2 cells, and hamster kidney-derived BHK cells, and the like.

The method of introducing a nucleic acid into an animal cell is not particularly limited, as long as the nucleic acid is expressed in the animal cell, and the method can be chosen as appropriate according to the kind of the animal cell and the like. Examples include lipofection, microinjection, calcium phosphate co-precipitation, PEG method, electroporation and the like.

Examples of the medium used to culture animal cells include an MEM medium containing about 5 to 20% fetal bovine serum (Science, vol. 122, 501 (1952)), DMEM medium (Virology, vol. 8, 396 (1959)), RPMI 1640 medium (The Journal of the American Medical Association, vol. 199, 519 (1967)), 199 medium (Proceeding of the Society for the Biological Medicine, vol. 73, 1 (1950)) and the like. It is preferable that the pH be about 6 to 8. Cultivation is carried out normally at about 30 to 40° C. for about 15 to 60 hours, with aeration and stirring added as required.

Thus, the chimera protein of the present invention is expressed in the animal cell, and, by the action of a signal peptide in the chimera protein, the protein is transported onto the cell membrane of the animal cell along the secretion route.

In the above-described step (2), a paramyxovirus is infected to an animal cell that expresses the chimera protein of the present invention.

The paramyxovirus to be infected is not particularly limited, as long as it has the capability of reconstitution, whether a wild-type paramyxovirus or a modified paramyxovirus. However, if the chimera protein of the present invention has no fusion activity for cells per se, the modified paramyxovirus desirably retains at least the fusion activity of an F protein.

The infected paramyxovirus is reconstituted in the animal cell, transported to the cell membrane, and released outside the cell in a state surrounding a portion of the cell membrane like ectocytosis. For this reason, the paramyxovirus released outside the cell is a modified paramyxovirus presenting the chimera protein of the present invention being expressed on the cell membrane on the virus particle surface thereof.

Considering the above-described procedures for forming the modified paramyxovirus of the present invention, it is understood that it is possible to prepare the chimera protein of the present invention, without being expressed in an animal cell, as a proteoliposome wherein the chimera protein is embedded in a liposome consisting of an appropriate lipid (complex), and fuse this with an animal cell, to present the chimera protein on the cell membrane of the animal cell, and to infect the cell with a paramyxovirus, so as to allow the replication and reconstitution of the virus in the same way.

Furthermore, considering the utilization of the above-described proteoliposome, the protein for targeting used in the present invention may comprise a non-peptide component capable of binding specifically to a cell surface molecule (herein, peptide substances comprising amino acids other than the 20 amino acids encoded by nucleic acid sequences (codons) are also understood to be included in the non-peptide component mentioned here) along with the virus surface protein. For example, molecules that bind specifically to a folic acid receptor include folic acid; by forming an amide bond between the folic acid molecule and the amino-terminus of the virus surface protein or a fragment thereof, or between the amino group of the side chain and the carboxyl group of folic acid, or by forming an amide bond between the carboxyl group of the side chain and the amino group of folic acid, a protein conjugate of the virus surface protein and folic acid bound covalently can be prepared. If such a protein conjugate is presented on the cell membrane of an animal cell by means of proteoliposome, and the animal cell is infected with a paramyxovirus, the paramyxovirus replicated, reconstituted, and released outside the cell would be a modified paramyxovirus presenting the protein conjugate on the virus surface thereof, and this can be used to target cells that express a folic acid receptor.

If any other non-peptide component capable of binding specifically to a cell surface molecule has no structure capable of covalently binding to the N-terminus of a virus surface protein or a functional group on an amino acid side chain, it is also possible to bind the component by, for example, using a commonly known linker in common use for the preparation of immunoconjugates.

In the above-described step (3), modified paramyxovirus particles are isolated. Isolation of the virus particles is achieved by a method known per se, for example, recovery and centrifugation of the cell culture supernatant.

The modified paramyxovirus obtained by the method of the present invention is presenting on the viral surface thereof a chimera protein wherein a virus surface protein has been joined to a peptide that binds specifically to the cell surface molecule of a target cell. Therefore, the modified paramyxovirus is highly specific for target tissue/cells. The modified paramyxovirus can also be utilized as a paramyxovirus vector (virus envelope vector and the like) capable of site-specific delivery of a drug and the like.

Herein, a virus envelope vector refers to a vector wherein the virus genome has been deactivated by a variety of methods such as UV irradiation, sonication, and surfactant treatment to eliminate the replicating capability of the virus. A virus envelope vector comprises an envelope, i.e., a membrane structure based on a lipid bilayer surrounding the nucleocapsid in the virus. Because such a virus envelope vector maintains the protein present on the virus particle surface, it is adsorbable to cells, and can be utilized as a vector for delivering a substance enclosed in virus particles (e.g., proteins, nucleic acids, low-molecular compounds) into cells.

Both the method of preparing a virus envelope vector from virus, and the method of enclosing a substance in a virus envelope vector are already commonly known, and are described in, for example, Molecular Therapy, 2002 vol. 6 219-226 and the like.

For example, an envelope vector having a fusion protein wherein transferrin has been fused to the N-terminus side of the transmembrane domain of F protein on the particle surface thereof, by the cancer cell specific binding capacity of transferrin, is capable of delivering a substance only to cancer cells as a cancer cell-specific targeting vector.

An envelope vector having a fusion protein wherein a single-chain antibody variable fragment (scFv) that recognizes desmoglein 3 has been fused to the N-terminus side of the transmembrane domain of F protein on the particle surface thereof, by the epidermal basal layer specific binding of the fragment, as a epidermal basal layer-specific targeting vector, is capable of delivering a substance only to the epidermal basal layer.

When a substance is delivered to a desired cell using the above-described virus envelope vector, the virus envelope vector having the substance enclosed in the virus particles thereof is used alone, or is used as a pharmaceutical composition comprising a combination of the vector and a stabilizer compound, diluent, and carrier.

The pharmaceutical composition comprises an effective amount of the vector to ensure that the above-described virus envelope vector accomplishes the intended purpose. "A therapeutically effective amount" or "a pharmacologically effective amount" is a term fully recognized by those skilled in the art, referring to an amount of a drug that is effective for producing an intended pharmacological effect. Therefore, a therapeutically effective amount is an amount sufficient to mitigate signs of the disease to be treated. A useful assay to confirm an effective amount for a specified application (for example, a therapeutically effective amount) is to measure the degree of recovery of the target disease. The actually administered dose depends on the individual to receive the treatment, and is preferably an amount optimized to achieve a desired effect without a considerable adverse reaction. Determination of a therapeutically effective dosage well resides in the capability of those skilled in the art.

The pharmaceutical composition can be used in a form such that the virus envelope will be incorporated in the cells of the affected portion of the body or the cells of target tissue.

The pharmaceutical composition can be administered in an optionally chosen aseptic biocompatible pharmaceutical carrier (including, but are not limited to, physiological saline, buffered physiological saline, dextrose, and water). All these molecules, in a pharmaceutical composition blended with an appropriate excipient and/or a pharmaceutically acceptable carrier, can be administered alone, or in combination with other drugs, to a patient. The pharmaceutically acceptable carrier can be pharmaceutically inert.

Administration of the pharmaceutical composition is achieved orally or parenterally. Methods of parenteral delivery include topical, intra-arterial (for example, via carotid), intramuscular, subcutaneous, intraspinal, subarachnoidal, intracerebroventricular, intravenous, intraperitoneal, or nasal administration. The present invention can be administered by any route, as long as the route reaches the treatment site.

The dosage of the virus envelope vector is chosen as appropriate according to age and other factors for the recipient, the purpose of administration, the kind of vector used and the like.

When the virus of the present invention is administered as a virus envelope vector to a human, a virus envelope vector can be administered in an amount usually equivalent to 400 to 400,000 HAU, preferably equivalent to 1,200 to 120,000 HAU, more preferably equivalent to 4,000 to 40,000 HAU, per subject. "HAU" refers to the activity of a virus by which 0.5% of chicken erythrocytes can be aggregated. 1 HAU nearly equals 24000000 virus particles (Okada, Y. et al., Biken Journal 4,209-213, 1961). The above-described amount can be administered, for example, once to several times a day.

The exact dose is chosen by each clinician in consideration of the kinds of substances contained in the vector and the patient to be treated. The dosage and administration are adjusted so that a sufficient level of active portion is provided, or a desired effect is maintained. Further factors that can be taken into consideration include the severity of disease condition; the patient's age, body weight, and sex; limitation on the time of food intake during treatment, and frequency, drug combination, reaction susceptibility, and resistance/responses to treatment). According to the half-life and clearance rate of a particular preparation, a sustained-action pharmaceutical composition can be administered every 3 to 4 days, weekly, or biweekly.

The disclosures in all publications mentioned herein, including patents and patent application specifications, are incorporated by reference herein in the present invention to the extent that all of them have been given expressly.

The present invention is hereinafter described in more detail by means of the following examples, to which, however, the present invention is never limited.

EXAMPLES

Example 1

(1) Preparation of siRNA Against HN mRNA

The five siRNAs for HN mRNA knock down shown in FIG. 1 were designed and synthesized using SMART siRNA Technology™ (Dharmacon Research). The five siRNAs (HN-223, HN-342, HN-899, HN-1142, HN-1427) target GCAUUGAACAUGAGCAGCA (223-241: SEQ ID NO:1), GAACAAAAACAGCAGGGAU (342-360: SEQ ID NO:2), GAACUAAGUCUCACCGGUA (899-917: SEQ ID NO:3), GCGUGAUCAUCCAGGUCAA (1142-1160: SEQ ID NO:4), and GCGUAUACACUGAUGCUUA (1427-1445: SEQ ID NO:5), respectively, on the HN mRNA. The scramble siRNA used as the control consists of a random sequence (GCGCGCUUUGUAGGAUUCG: SEQ ID NO:6).

(2) Detection of Effects of siRNAs

The synthesized siRNAs were introduced to LLCMK2 cells at various concentrations by utilizing Lipofectamin Reagent (Invitrogen™, California, USA) and Plus Reagent (Invitrogen™) in accordance with the respective protocols.

24 hours after introduction, cultured cells were washed with Dulbecco's Phosphate Buffered Saline (−) (PBS) (Nacalai Tesque Inc. Tokyo, Japan), Opti-MEM I (GIBCO™, Invitrogen) comprising HVJ, previously adjusted to a concentration of multiplicity of infection (MOI) 0.02, was added, and the cells were incubated at 37° C. in 5% CO2-95% air for 1 hour to infect HVJ. After 24 hours, total RNA was extracted from the cultured cells using RNeasy (QIAGEN K.K. Tokyo, Japan). After 30 μg of total RNA was fractionated by 1% agarose gel (Cambrex Bio Science Rockland Inc, Rockland, USA) electrophoresis, the fraction was transferred onto a Hybond-N+ nylon transfer membrane (Amersham Biosciences UK Ltd. Buckinghamshire, England). HN and G3PDH cDNA were labeled with $^{32}P$ using Random Primers DNA Labeling System (Invitrogen™), hybridization was performed as directed in the manual for PerfectHyb™ (TOYOBO Co Ltd., Osaka, Japan), after which the membrane was exposed to KODAK BioMax MS Film (KODAK, Tokyo, Japan) and analyzed.

Figure 2:
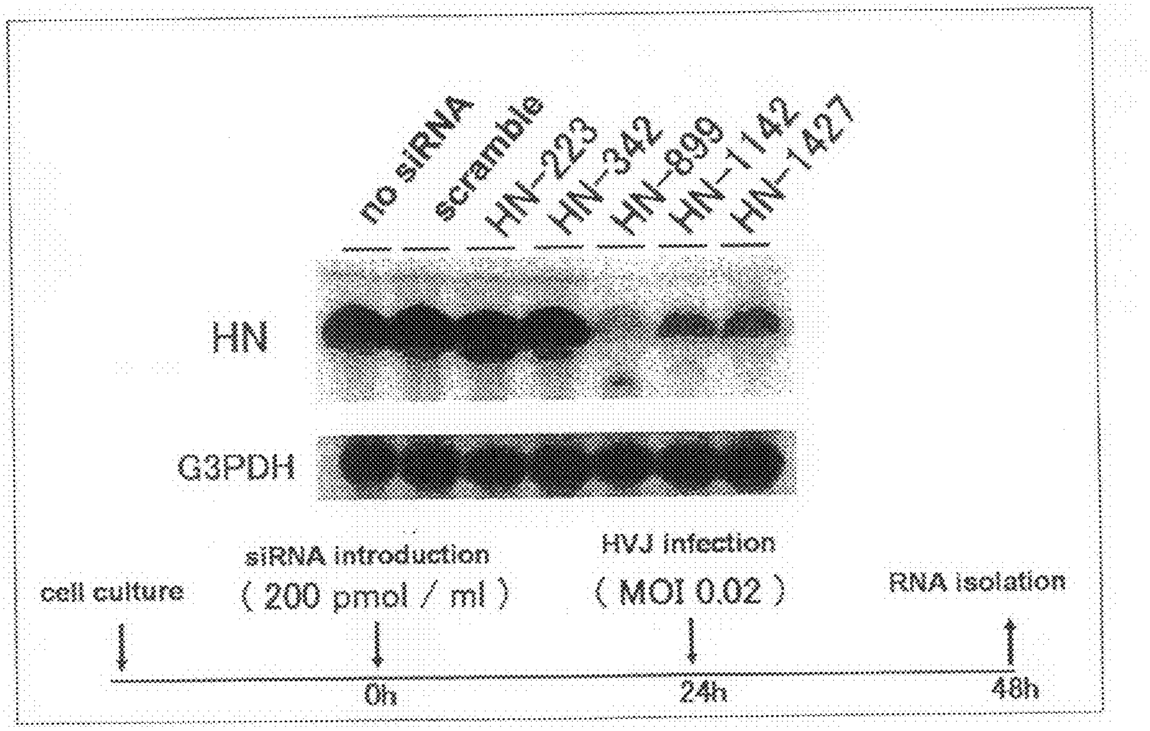
FIG. 2 shows the effect of an siRNA against HN mRNA.

The results are shown in FIG. 2. Of the above-described siRNAs, HN-223 and HN-342 were nearly ineffective, whereas HN-899, HN-1142 and HN-1427 significantly inhibited the transcription of HN protein.

(3) Changes Over Time in HN Knock Down by siRNA

Figure 3:
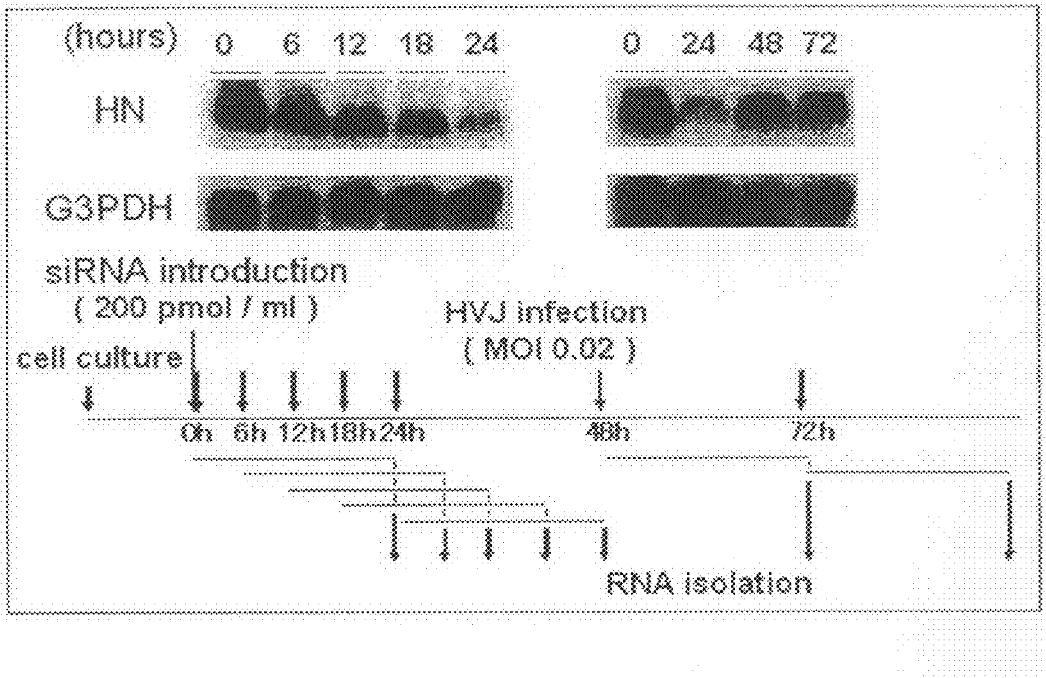
FIG. 3 shows changes over time in HN knockdown with an siRNA.

Using HN-899, per the time schedules shown in the lower panel of FIG. 3, while the duration of HVJ infection was changed, detection of the effect of each siRNA over time was attempted. As a result, as shown in FIG. 3, it was found that the transcription of HN protein was suppressed mostly with the time schedule wherein HVJ was infected 24 hours after introduction of the siRNA, and RNA was recovered 24 hours later.

(4) Investigation of Optimum Concentrations of siRNA

Figure 4:
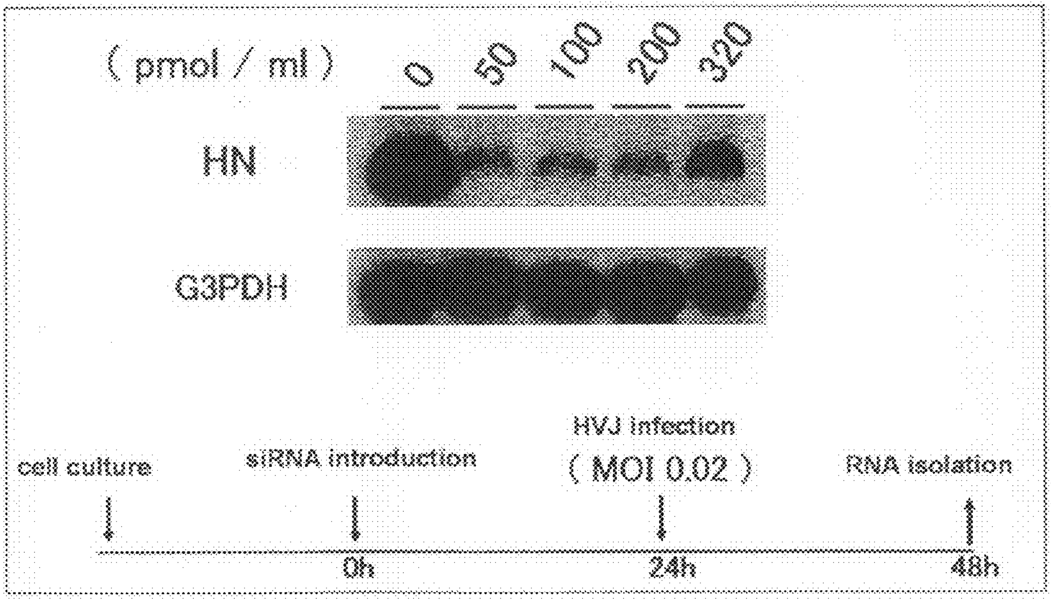
FIG. 4 shows an investigation of the optimum concentration of an siRNA.

While the concentration of the HN-899 siRNA was changed between 50 and 320 pmol/ml, it was introduced as described above, after which HVJ infection and RNA recovery were performed as described above, and the concentration-dependent effect of the siRNA was investigated. As shown in FIG. 4, a sufficient effect was obtained at 50 pmol/ml.

(5) Specificity of siRNAs for HN

Figure 5:
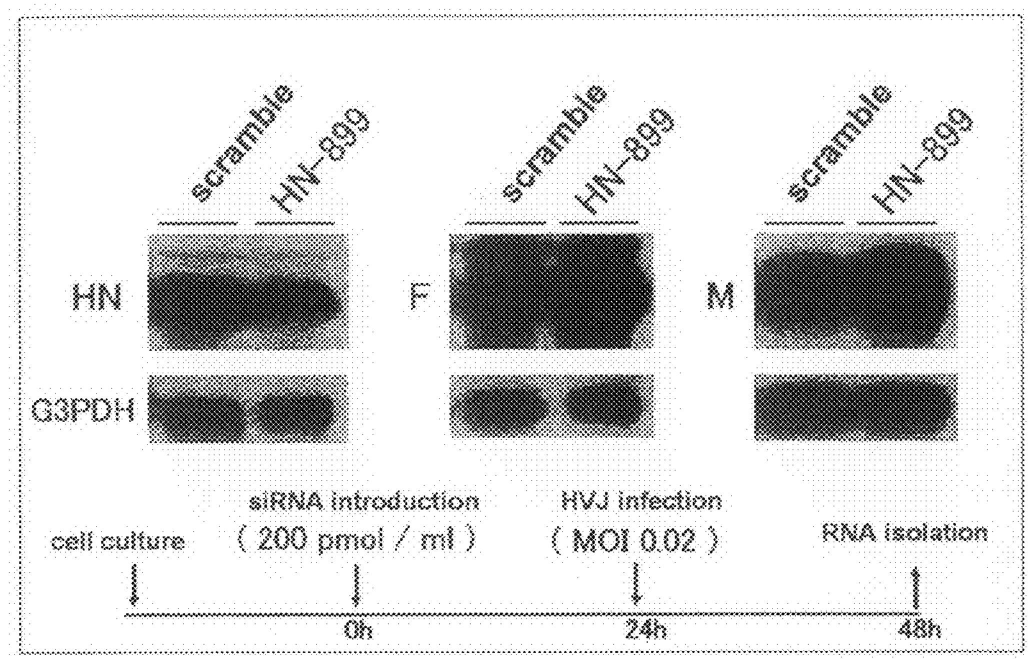
FIG. 5 shows the HN mRNA specificity of HN-siRNA.

As shown in FIG. 5, regarding the RNAs recovered in the same manner as described above, detection of the amounts of HN protein mRNA, F protein mRNA and M protein mRNA was attempted by Northern blotting; the HN-899 siRNA specifically suppressed the transcription of HN protein.

(6) Recovery of Newly Budding Virus from HVJ-Infected Cells and Western Blotting LLCMK2 cells infected with HVJ virus were cultured in an MEM containing Penicillin/Streptomycin at 37° C. in 5% $CO_2$-95% air for 48 hours. Virus particles were recovered from the culture supernatant via centrifugation at 100,000×g, and suspended in PBS.

HVJ was dissolved in 2× sample buffer (125 mM Tris-HCl (pH 6.8)/10% 2-mercaptoethanol/4% sodium dodecilsulfate/10% sucrose/0.004% bromophenol blue), and electrophoresed on sodium dodecylsulfate-polyacrylamide gel (12%), after which the sample was transferred onto Immobilon-P Transfer Membrane (Millipore Co, Billerica, USA) using HorizBlot (horizontally layered electrophoresis transfer apparatus, Atto, Tokyo, Japan). Next, after the membrane was subjected to blocking in a washing buffer (684 mM NaCl/4 mM Tris/0.1% Tween 20) containing 5% skimmed milk (Nacalai Tesque Inc.) at room temperature for 1 hour, the membrane was reacted with a primary antibody (diluted with 5% skimmed milk 1,000 fold for anti-HN antibody, 200 fold for anti-F antibody, 2,000 fold for anti-M antibody) at room temperature for 1 hour. Subsequently, the membrane was washed with the washing buffer, and reacted with a secondary antibody (anti-rabbit IgG antibody in the case of HN and M, anti-mouse IgG antibody in the case of F, both diluted with 5% skimmed milk 2,000 fold) at room temperature for 1 hour. After the secondary antibody reaction, the membrane was washed with the washing buffer, and detection was performed using ECL Western Blotting Detection Reagent (Amersham Biosciences).

Figure 6:
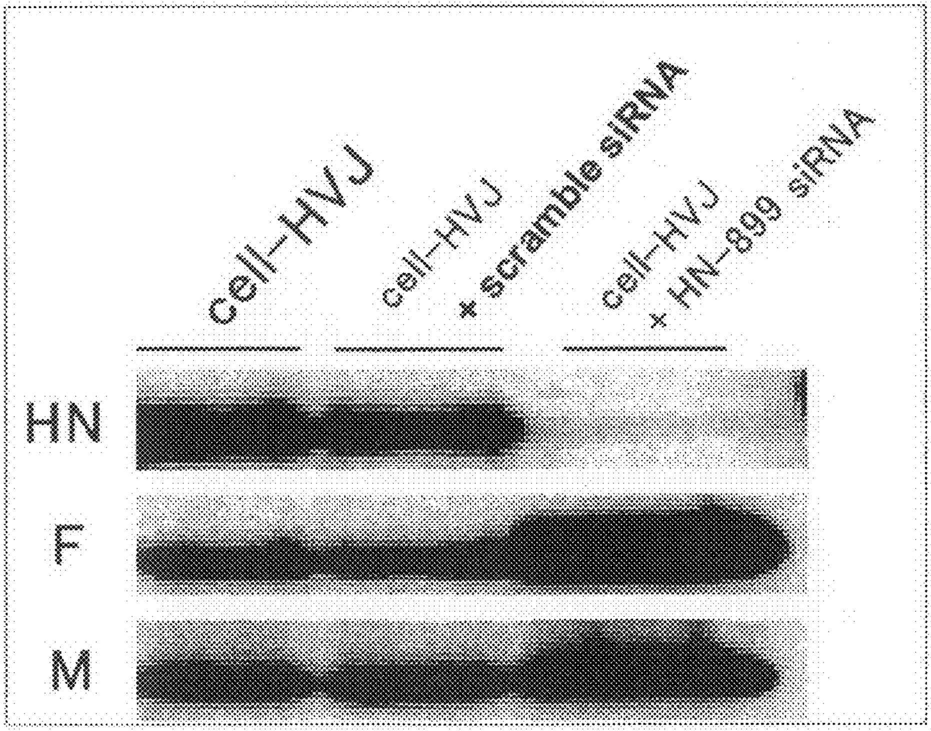
FIG. 6 shows the influence of an siRNA on virus protein expression.

The results are shown in FIG. 6. In the HVJ recovered from the cells incorporating HN-899, almost no HN was expressed. On the other hand, F protein and M protein increased compared with the HVJ recovered from the cells incorporating a scramble siRNA.

(7) Comparison of Virus Particle Counts

Figure 7:
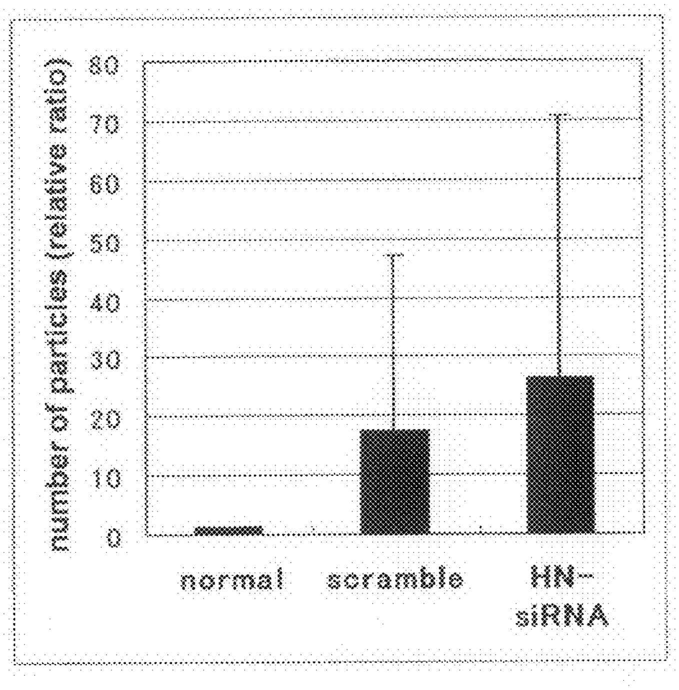
FIG. 7 shows an investigation of the number of budding virus particles.

To investigate the number of HVJ virus particles produced by HVJ infection in the presence of an siRNA introduced, virus genome quantitation for comparison of virus particle counts was performed by real-time PCR. Oligonucleotide primers for detection of the HVJ genome, and fluorescent label probe were designed using Primer Express (registered trademark) Software 1.5 of Applied Biosystems. The primer sequences were GGCATAGAAGGTTACTGCCAGAA (HVJ-10769F: SEQ ID NO:7) and TGTCACGGCTATAGCTTGATTGTC (HVJ-10897R: SEQ ID NO:8), and the probe sequence was ATCCACCTAGCAGCTGT (SEQ ID NO:9). Using PURESCRIPI RNA Isolation Kit (Gentra Systems, Inc. Minnesota, USA), RNA genome was extracted from the recovered cell-derived HVJ, and cDNA was synthesized using SuperScript™III First Strand Synthesis System (Invitrogen™). Realtime PCR assay was performed using Applied Biosystems 7700 Sequence Detector (Applied Biosystems) with the above-described primers and probe, and Taqman Universal PCR Master Mix (Applied Biosystems Co., Ltd. California, USA), to determine the amount of genome, and the number of particles were calculated. The results are shown in FIG. 7. A larger number of virus particles were produced with the introduction of a scramble RNA and with the introduction of the HN-899 siRNA than without RNA (normal).

(8) Determination of Hemagglutination (HA) Activity

Figure 8:
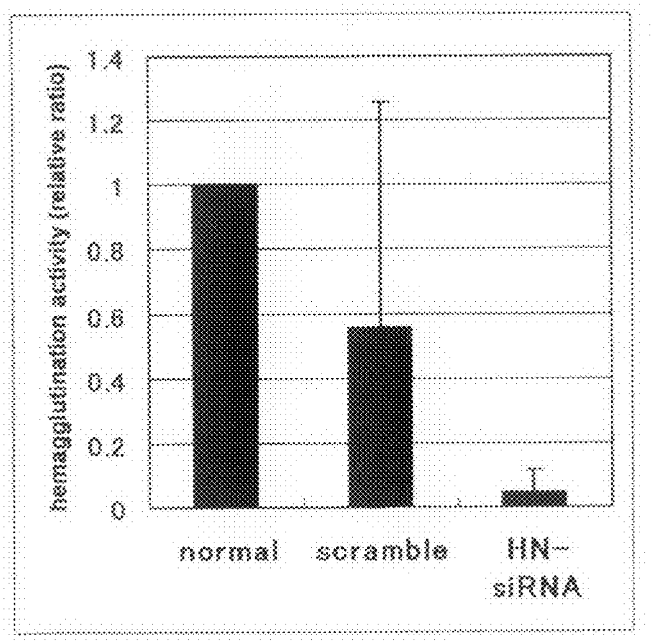
FIG. 8 shows a comparison of hemagglutination activity.

After siRNA introduction and HVJ infection, all virus particles present in a constant volume of the culture supernatant thereof was recovered, and chicken erythrocyte aggregation activity was determined; in the HN-899-transfected group, the activity was about one-tenth of the level for normal HVJ (FIG. 8). Here, this aggregation activity was determined by preparing a series of 2-fold dilutions of HVJ suspension, mixing each with 1% erythrocyte-containing liquid in a volume equal to that of the diluent, examining hemagglutination, and calculating the titer (HAU/ml) of the HVJ suspension using the equation shown below.

$$HAU/\text{ml}=2n\times\text{dilution rate}$$

n: maximum dilution number at which aggregation reaction is observed

Dilution rate: the dilution rate for the original sample if diluted

Figure 9:
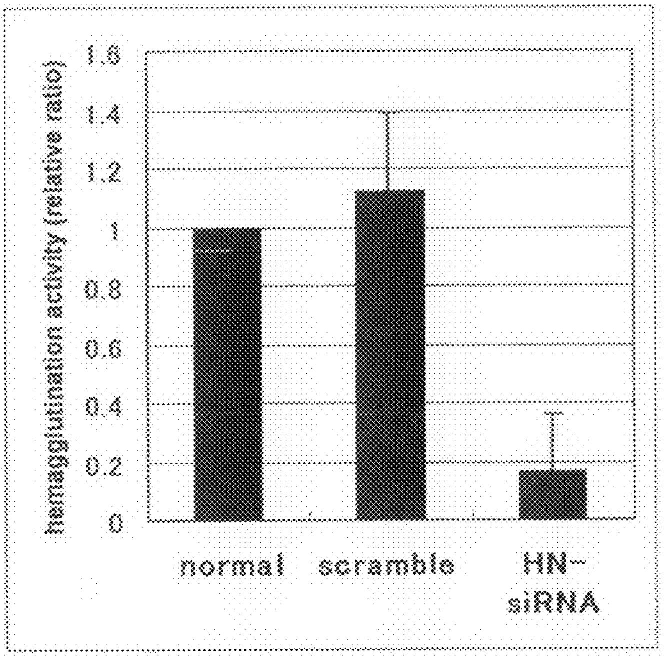
FIG. 9 shows hemagglutination activity per unit number of virus particles.

Next, hemagglutination activity per unit virus particle count was determined. As shown in FIG. 9, as expected, the virus obtained from the HN-899 siRNA-transfected cells exhibited a reduced hemagglutination activity.

Example 2

Figure 10:
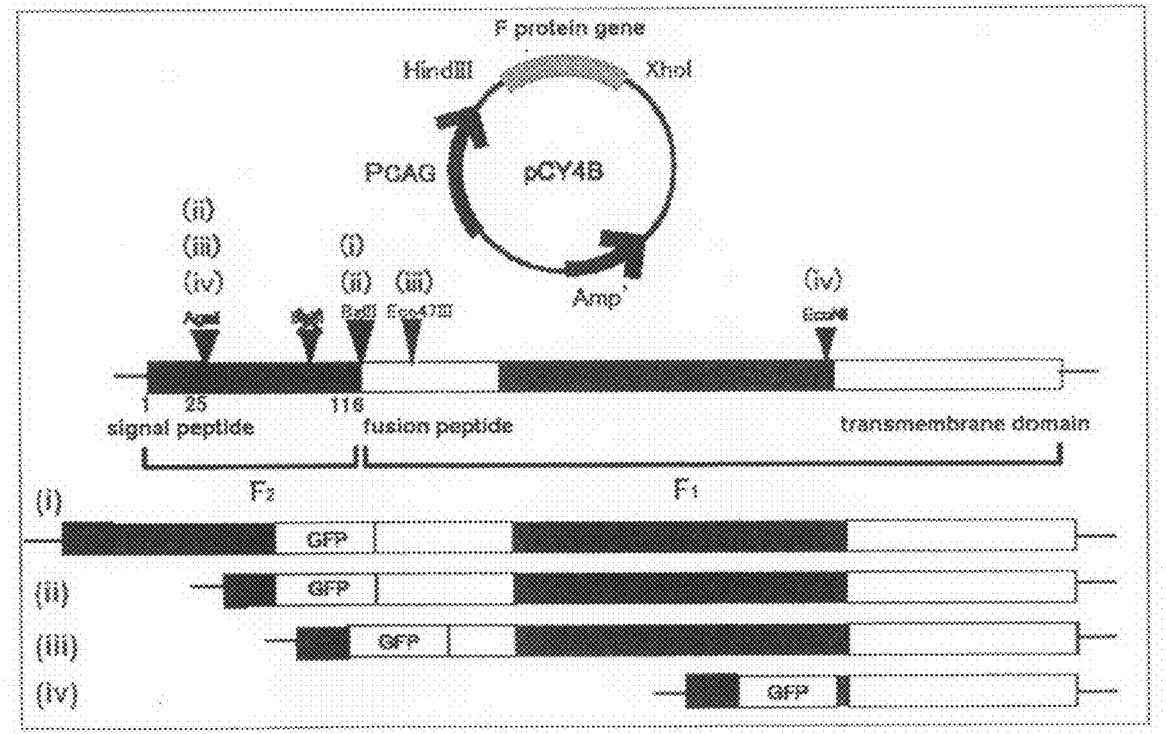
FIG. 10 shows the preparation of a tissue targeting F protein expression vector.

(1) Preparation of Expression Vector for Chimera F Protein of HVJ-F and GFP or Dsg-3-scFv Vectors for expressing the chimera EGFP-F proteins shown in FIG. 10 (i) to (iv) were prepared.

Using Mutagenesis (Promega), the pcDNA3.1-F plasmid was mutated to delete the intrinsically possessed BglII recognition site (279-284), and an AgeI recognition site (82-87) and a BglII recognition site (346-351) were newly prepared, to yield a new plasmid vector (pcDNA3.1-Fmut). This was cleaved with HindIII/XhoI, and the F fragment obtained was inserted into similarly cleaved pCY4B to yield pCY4B-Fmut. To insert EGFP into each of the BglII cleavage site ((i) in FIG. 10), AgeI-BglII site ((ii) in FIG. 1), AgeI-Eco47III site ((iii) in FIG. 10), and AgeI-EcoNI site ((iv) in FIG. 10) in pCY4B-Fmut, amplification from pEGFP-C1 (BD Biosciences Clontech) was performed by PCR to yield EGFP cDNA fragments.

The PCR primers used here are as follows:

```
                                    (SEQ ID NO: 12)
GFP-BglII-f:    5'-CATGGTGAGCAAGGGCGAGG-3'

                                    (SEQ ID NO: 13)
GFP-BglII-r:    5'-TTCTAGATCCGGTGGATCCG-3'
```

-continued

```
                                  (SEQ ID NO: 14)
GFP-AgeI-f:     5'-TATGGTGAGCAAGGGCGAGGAG-3'

                                  (SEQ ID NO: 15)
GFP-Eco47IIIr: 5'-GCTCTAGATCCGGTGGATCCCG-3'

                                  (SEQ ID NO:16)
GFP-EcoNI-r:    5'-ATCTAGATCCGGTGGATCCCG-3'
```

Using GFP-BglII-f and GFP-BglII-r for the acquisition of an EGFP cDNA fragment incorporating a BglII cleavage site in FIG. 10 (i), GFP-AgeI-f and GFP-Eco47III-r for the acquisition of an EGFP cDNA fragment incorporating an AgeI-BglII site in FIG. 10 (ii), GFP-AgeI-f and GFP-Eco47III-r for the acquisition of an EGFP cDNA fragment incorporating an AgeI-Eco47III site in FIG. 10 (iii), and GFP-AgeI-f and GFP-EcoNI-r for the acquisition of an EGFP cDNA fragment incorporating an AgeI-EcoNI site in FIG. 10 (iv), PCR amplification was performed.

After pCY4B-Fmut was cleaved with BglII alone, or with AgeI and BglII, AgeI and Eco47III or AgeI and EcoNI, the resulting fragments were blunt-ended with Blunting High (TOYOBO), after which each of the above-described EGFP cDNAs obtained by amplification was ligated by a reaction with Ligation High (TOYOBO) at room temperature for 5 minutes to yield the chimera EGFP-F protein expression vectors schematized in FIG. 10 (i) to (iv).

The cDNA sequence of F protein is shown by SEQ ID NO:10; in the above-described (i), a PCR product fragment has been inserted between 345-position and 346-position; 87 to 345 positions in the above-described (ii), 87 to 455 positions in the above-described (iii), and 87 to 1465 positions in the above-described (iv) have been substituted by corresponding PCR product fragments, respectively.

(2) Introduction of the Above-Described Vectors into Cells (transfection) and GFP Immunostaining On the day before transfection, a cover glass (IWAKI) was placed on a 6-well plate, and $2\times10^5$ LLCMK2 cells were sown.

On the day of transfection, the medium was replaced with 800 μl of D-MEM(−), and the cells were cultured for 3 hours, after which 1 μg of plasmid DNA was introduced using Lipofectamin Plus (invitrogen); 4 hours later, 1 mL of D-MEM(+) was added, and the cells were cultured for 48 hours.

Fixation was performed in 4% para-formaldehyde at 4° C. for 15 minutes; an aliquot was incubated with 0.1% Triton-X for 2 minutes, and then blocked with 5% skimmed milk/PBS for 1 hour.

The plate was incubated with the primary antibody Anti-Green Fluorescent Protein (GFP) PoAb Purified IgG (MBL): 1/2000 for 1 hour, washed with PBS 3 times, incubated with the secondary antibody Alexa Fluor 555 goat anti-rabbit IgG (H+L): 1/1000 for 1 hour, and then washed with PBS 3 times. After enclosure with a cover glass, the cells were examined using a confocal microscope (Nikon).

Figure 11:
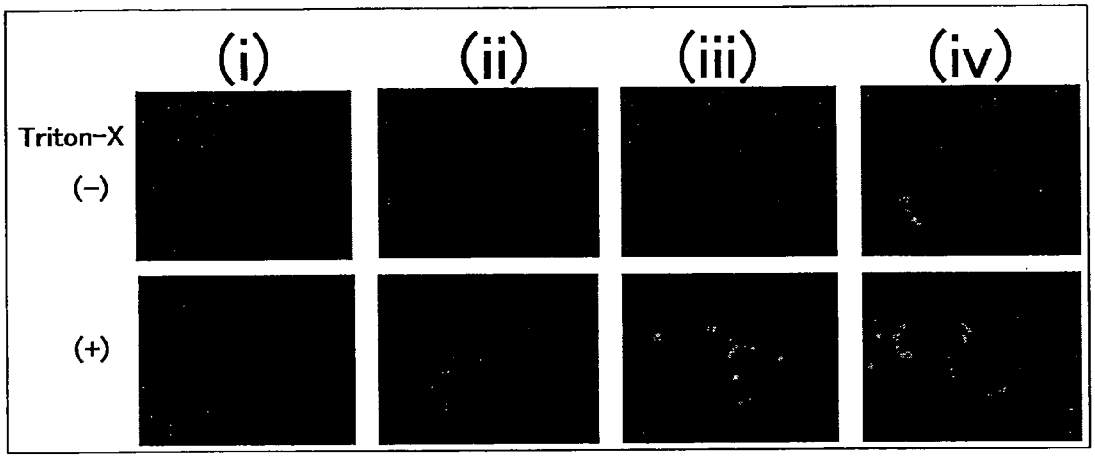
FIG. 11 shows an investigation of the intracellular localization of GFP fusion F protein (x1800).

The results are shown in FIG. 11. The upper panel shows the results obtained without incubation with 0.1% Triton-X; the lower panel shows the results obtained with incubation with 0.1% Triton-X. In both cases, EGFP was stained red, and the nucleus was stained blue by Hoechst 33258.

As seen from FIG. 11, all the chimera proteins (i) to (iv) above were expressed in the cells (FIG. 11, lower panel); however, without cell permeabilization with Triton-X, only (iv) was stained with EGFP; it is seen that only the chimera protein of (iv) is localized on the cell surface.

Figure 12:
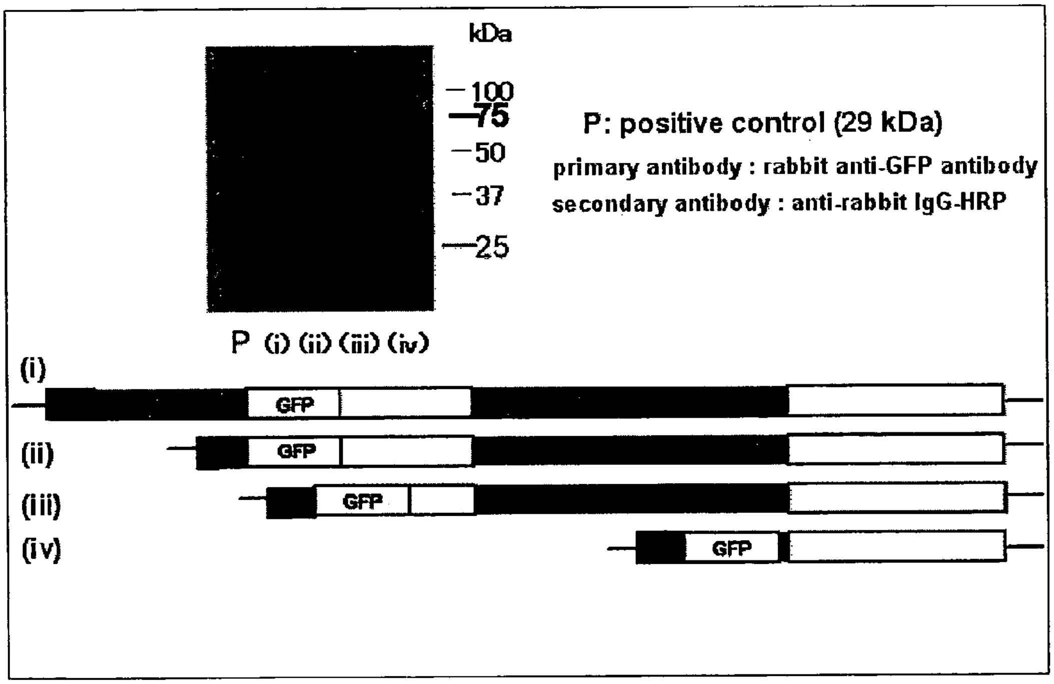
FIG. 12 is a drawing of the detection of the expression of GFP fusion F protein by Western blotting (upper panel). Shown in the lower panel is a schematic diagram of respective chimera proteins.

It was confirmed by Western blotting with anti-GFP antibody that the intended chimera protein was expressed (FIG. 12). The method of Western blotting is described below.

48 hours after transfection, $2\times10^5$ cells were dissolved in 20 μL of SDS sample buffer to prepare a sample. The sample was separated on 12% SDS polyacrylamide gel, and transferred onto a PVDF membrane (Millipore). The membrane was incubated in 5% skimmed milk/wash buffer (2 mM Tris-HCl pH 8.0, 0.02% NaCl, 0.05% Tween 20); with blocking buffer for 1 hour; next, primary antibody 1:2000 Anti-Green Fluorescent Protein (GFP) PoAb Purified IgG (MBL), 1:400 f236 (anti-F antibody), and 1:1500 anti-HN antibody were diluted with the blocking buffer, and incubation was performed at room temperature for 1 hour. After the membrane was washed with the wash buffer, detection was attempted using horseradish peroxidase-conjugate anti-rabbit or anti-mouse secondary antibodies (1:1000, Amersham Pharmacia).

As shown in FIG. 12, respective bands were detected at the positions corresponding to the molecular weights of the intended chimera proteins.

Therefore, it was found that only a chimera protein wherein only the N-terminus 29 residues of the transmembrane domain of F protein has been fused with GFP could be localized on the cell surface.

(3) Production of HVJ Having Chimera GFP-F Protein

Figure 13:
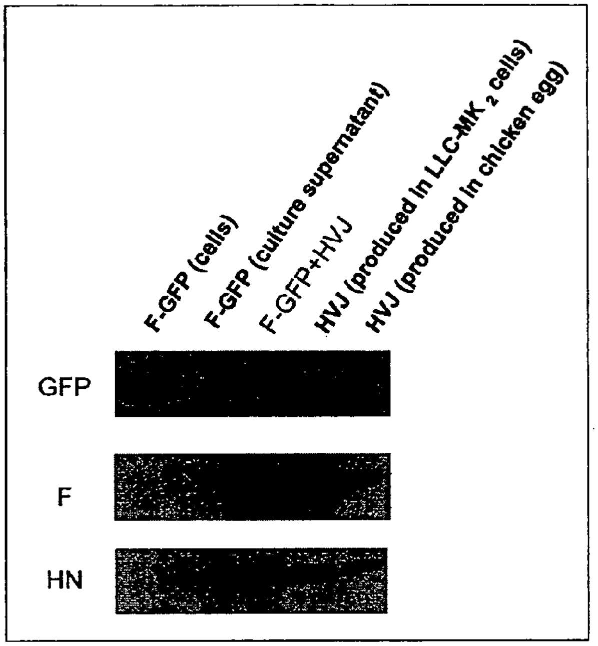
FIG. 13 shows the detection of GFP-F on Dsg3-scFv-HVJ by Western blotting.

The above-described cells transfected with the chimera GFP-F protein expression vector were infected with wild-type HVJ at m.o.i=0.6. After cultivation with MEM medium for 48 hours, the supernatant was recovered and centrifuged (440 g, 5 minutes) to remove the cells, the supernatant was further centrifuged (100000 g, 2 hours), and the HVJ pellets obtained were washed with PBS, after which they were suspended in an appropriate amount and subjected to SDS-PAGE, and then applied to Western blotting with anti-GFP antibody. The results are shown in FIG. 13. The lanes in FIG. 13 show, from left, the above-described cells transfected with the chimera GFP-F protein expression vector, not infected with HVJ (F-GFP(cells)), the culture supernatant of the transfected cells (F-GFP(culture supernatant)), a virus recovered from the supernatant of the transfected cells infected with wild-type HVJ (F-GFP+HVJ), a virus recovered from the culture supernatant of non-transfected LLC-MK2 cells infected with wild-type HVJ (HVJ (produced in LLC-MK2 cells)), and control HVJ produced in an egg and purified.

Referring to FIG. 13, GFP was detected in the virus recovered from the supernatant of the transfected cells infected with wild-type HVJ. Furthermore, when Western blotting was performed with an antibody that recognizes extracellular domain of F protein, F protein was detected also in the above-described virus, and the antibody does not recognize chimera GFP-F protein; therefore, it was found that the virus was expressing both the wild type and chimera F proteins. Furthermore, HN protein was also expressed.

(4) Preparation of scFv Fusion Chimera F Protein Expression Vector

Figure 14:
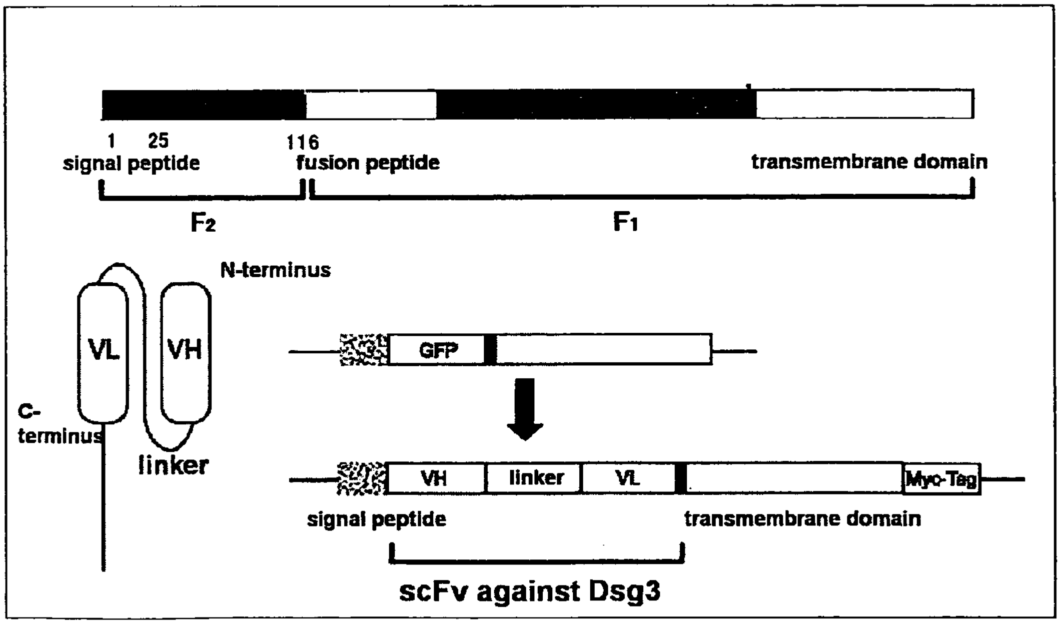
FIG. 14 shows the preparation of an scFv fusion F protein expression vector.

From the above-described results, an attempt was made to prepare the mentioned basal layer targeting HVJ using a single-chain antibody that recognizes desmogrein 3 protein expressed in epidermal basal layer (mDsg3-scFv) (FIG. 14). A cDNA of a single-chain antibody that recognizes desmoglein 3 protein is shown by SEQ ID NO:17. This was obtained by PCR amplification with pCANTAB5-AK7/scFv (supplied by Professor Amagai at the Department of Dermatology, Keio University School of Medicine) as the template, using a primer pair of Dsg3-scFv-AgeI-f: 5'-TATGGCGGACTACAAAGATATTGTGTTAAC-3' (SEQ ID NO:18) and Dsg3-scFv-EcoNI-r: 5'-AGGAGACTGTGAGAGTG-3' (SEQ ID NO:19).

This was inserted to the AgeI-EcoNI site of the aforementioned pCY4B-Fmut, and a DNA was designed to attach Myc-Tag to the C-terminus so as to facilitate the detection (pCAGIpuro-Dsg3-scFv-F).

(5) Preparation of Persistently Transgenic Cells (Stable Transformant)

$5\times10^6$ LLCMK2 cells were suspended in 235 μL of Minimum Essential Medium (GIBCO). 15 μg of pCAGIpuro-Dsg3-scFv-F was dissolved in 15 μl of PBS. The cells and DNA were mixed, and electroporation was performed in Gene Pulser Cuvette (BIO-RAD) using GENE PULSER II (BIO-RAD) at 250 V and 975 μF, after which each 100 μL was dispensed to a 10 cm dish. Per 10 mL of MEM, 90 μg of puromycin (Nacalai Tesque) was added, the cells were cultured at 37° C., and cells incorporating plasmid DNA were selected.

Figure 15:
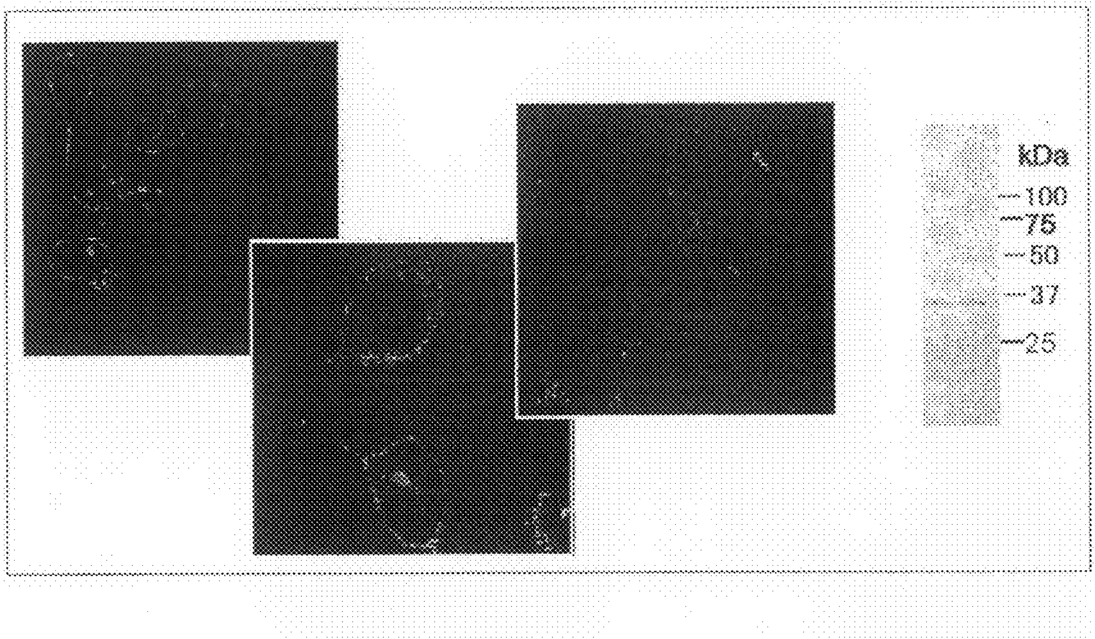
FIG. 15 is a drawing of the detection of the expression of scFv fusion F protein in a stable transformant by immunostaining. The transformant was examined using a microscope at magnification rates of 960 times, 1980 times and 2460 times in order from left.

When the selected cells were stained with anti-Myc antibody, chimera Dsg3-scF-F protein was localized on the cell membrane (FIG. 15). Western blotting also detected a band at the position corresponding to the size of the chimera protein.

(6) Production of HVJ Having Dsg3-scFv-F Chimera Molecule

Next, an attempt was made to produce HVJ having chimera Dsg3-scFv-F protein.

In a 15 cm dish, stable formant LLCMK2 cells in confluent state were infected with HVJ at MOI=0.4. After cultivation with MEM (P/S) for 48 hours, the supernatant was recovered and centrifuged (440 g, 5 minutes) to remove the cells, and the supernatant was further centrifuged (100000 g, 2 hours), the HVJ pellets obtained were washed with PBS, and then suspended in an appropriate amount.

Figure 16:
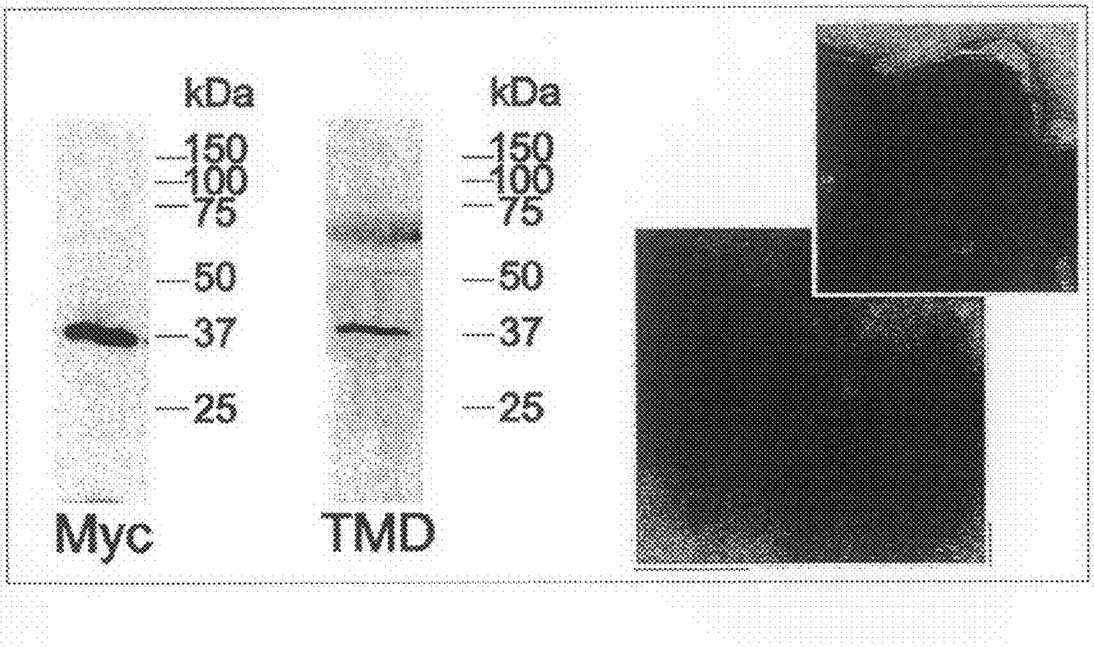
FIG. 16 shows the detection of Dsg3-scFv-F on Dsg3-scFv-HVJ produced using a stable transformant. The left panel (Myc) shows the results of Western blotting with anti-Myc antibody, the middle panel (TMD) shows the results of Western blotting with an antibody that recognizes the transmembrane domain of F protein. The right panel shows the results of examination by electron microscopy, the magnification rate being 42000 times for the left lower panel, and 56000 times for right upper panel.

The virus obtained was subjected to Western blotting with anti-Myc-tag antibody (FIG. 16, left panel: Myc), and Western blotting with an antibody that recognizes the transmembrane domain of F protein (FIG. 16 middle panel: TMD); a band of intended size was detected, confirming the chimera protein.

Furthermore, the virus stained with anti-Myc antibody was examined by electron microscopy.

100 HAU of HVJ was suspended in 4 μL of MilliQ, and this suspension was dripped onto a grid for electron microscopy, and dried. Fixation was performed in 3.7% formaldehyde at 4° C. for 15 minutes, the grid was washed with PBS 3 times, and incubated with 0.5% Triton-X for 3 minutes, after which the grid was again washed with PBS 3 times. The grid was incubated along with a primary antibody; Anti-Myc-tag (MBL) 1:100, at room temperature for 1 hour. After the grid was washed with PBS 3 times, the grid was incubated along with Rabbit anti-Mouse IgG-Gold Colloidal Particles-10 nm (EY RABORATORIES), previously diluted with PBS 1:100, at room temperature for 1 hour, and stained with uranium acetate, after which the virus was examined by electron microscopy (FIG. 16, right panel). Found on the virus surface was a block spot of the chimera protein stained.

(7) Investigation of Dsg3 Affinity of Dsg3-scFv-F-HVJ by ELISA

Next, the binding of mutant HVJ having scFV, which recognizes desmoglein 3, to desmoglein 3 was determined by ELISA. The method of ELISA is described below.

HVJ virus samples were prepared at various concentrations in 50 μL of assay diluent (MESACUP desmoglein test: MBL), and each sample was applied to a 96 well plate (supplied by Professor Amagai at the Department of Dermatology, Keio University) having mDsg3 immobilized thereon previously. After incubation at room temperature for 1 hour, the plate was washed with wash buffer (MESACUP desmoglein test: MBL) 4 times, and incubated along with 1:10 diluted f236 at room temperature for 1 hour. The plate was washed with the wash buffer 4 times, incubated along with a horseradish peroxidase-conjugate anti-mouse secondary antibodies (Amersham Pharmacia), previously diluted 1:9000 fold with conjugate diluent (MESACUP desmoglein test: MBL), at room temperature for 1 hour, and reacted with substrate solution (MESACUP desmoglein test: MBL) for 10 minutes, after which the reaction was stopped with a stop solution (MESACUP desmoglein test: MBL). Absorbance at 450 nm was measured using Mithras LB 940 (BERTHOLD).

Figure 17:
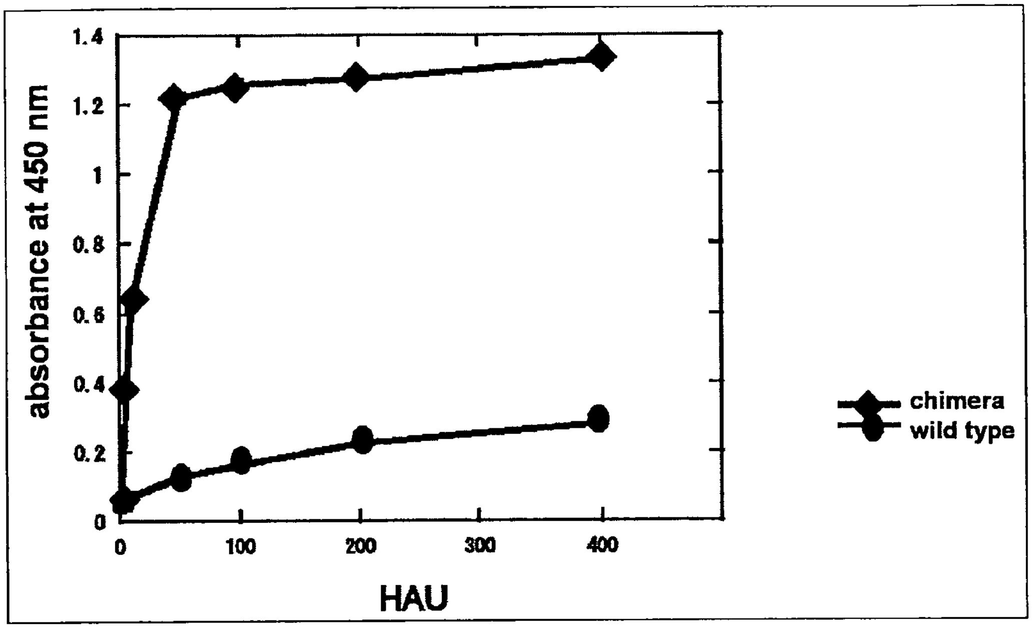
FIG. 17 shows the results of ELISA showing the desmoglein 3 binding activity of Dsg3-scFv-F chimera protein.

As shown in FIG. 17, in the HVJ having the chimera molecule, the binding was significantly enhanced compared with wild-type HVJ.

(8) Experiments of HVJ Infection to Cultured Cells

Infection of HVJ having the chimera protein to cultured cells was tested.

A cover glass (IWAKI) was placed on a 6-well plate, $3\times10^5$ cells of LLCMK2, $5\times10^5$ cells of PAM, or $3\times10^5$ cells of NIH3T3 were sown. On the following day, the virus samples (cell-derived wild-type HVJ and chimera HVJ), which had been treated with a final concentration of 4 μg/mL Trypsin at 37° C. for 30 minutes, were diluted with Opti-MEM at MOI=0.6, and applied to each cell, after which the cells were infected for 5 minutes. After washing with PBS 2 times, the cells were cultured in D-MEM and MEM for 24 hours, after which the cells were immunostained with f236.

Figure 18:
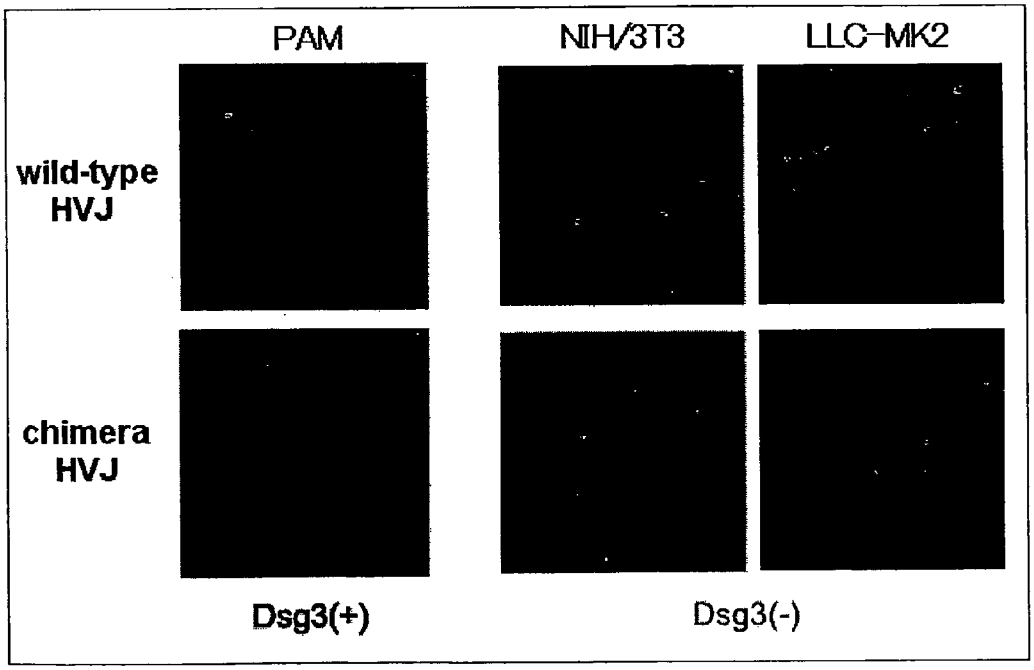
FIG. 18 shows the results of mouse keratinocyte targeting with Dsg3-scFv-HVJ. Wild-type HVJ (upper panel) or Dsg3-scFv-HVJ (chimera HVJ: lower panel) was allowed to act on PAM cells expressing desmoglein (Dsg3(+)) in the left column, and on NIH3T3 cells and LLC-MK2 cells not expressing desmoglein (Dsg3(−)) in both the middle column and right column. It is seen that only in the PAM cells, chimera HVJ was more abundant on the cell surface than the wild type.

The results are shown in FIG. 18. Of the three kinds of cells tested, only the mouse keratinocyte-derived PAM cells exhibited increased expression of chimera F protein compared with the wild type.

(9) Experiments of Infection with Chimera HVJ in Organ Culture

Furthermore, infection to mouse epidermal tissue was tested. In this study, type 7 collagen knockout mice were used since epidermal tissue is easy to separate. Because this type of mouse has bullae in the abdominal skin, it is easy to separate the epidermis and dermis.

Just after delivery, bulla portion skin of type 7 collagen knockout mice was resected, and subjected to organ culture on a 10 cm dish filled with D-MEM. A trypsinated virus sample (see (8)) was prepared to obtain $5\times10^5$ particles/100 μL Opti-MEM, and injected into bullae. After infection at 37° C. for 5 minutes, the epidermis and dermis were peeled, washed with PBS, and cultured in D-MEM. After 24 hours, the cultures were washed with PBS, and fixed in 4% para-formaldehyde, after which the F protein derived from the genome of the virus was immunostained with f236.

Figure 19:
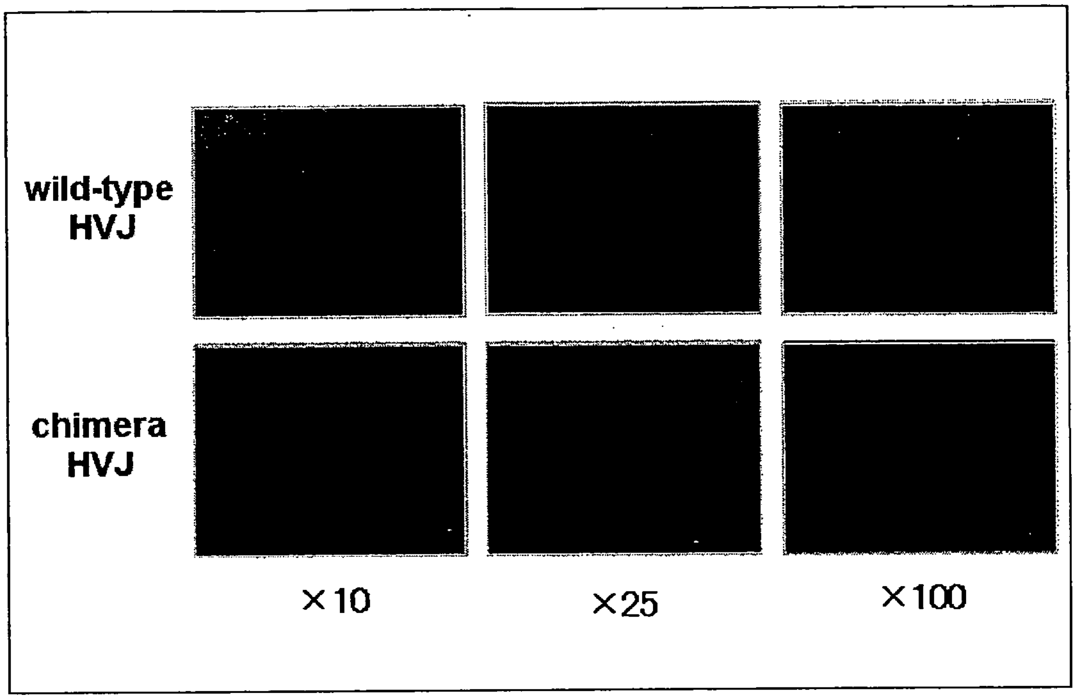
FIG. 19 shows the results of immunostaining of F protein in epidermal cells. On skin fragments of abdominal bulla portion of type 7 collagen knockout mice, wild-type HVJ (upper panel) or Dsg3-scFv-HVJ (chimera HVJ: lower panel) was allowed to act. It is seen that chimera HVJ was more abundant than the wild type.
Figure 20:
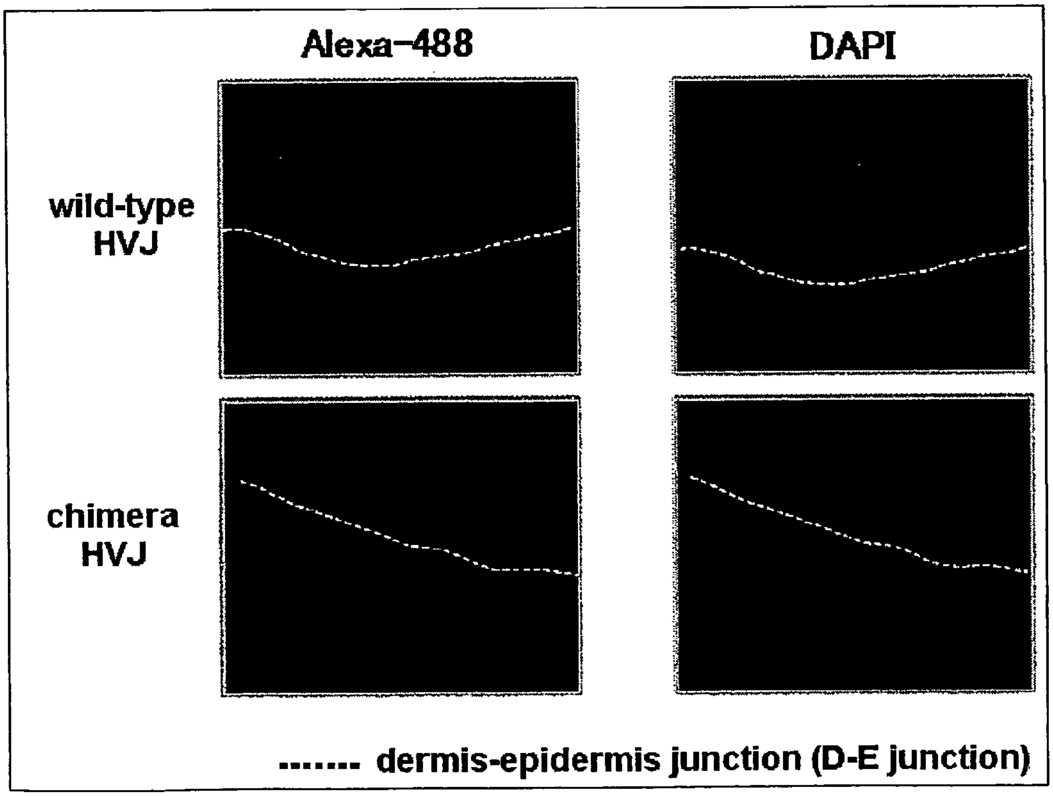
FIG. 20 shows immunostaining of F protein in a skin tissue section (cross-section) (400 times).

As a result, as shown in FIG. 19, significantly higher levels were detected in epidermal cells in chimera HVJ than in wild-type HVJ. Furthermore, when the tissue section was stained in the same manner, it was found that the expression of the chimera protein was localized exclusively in the epidermal normal cells (FIG. 20).

Example 3

Figure 21:
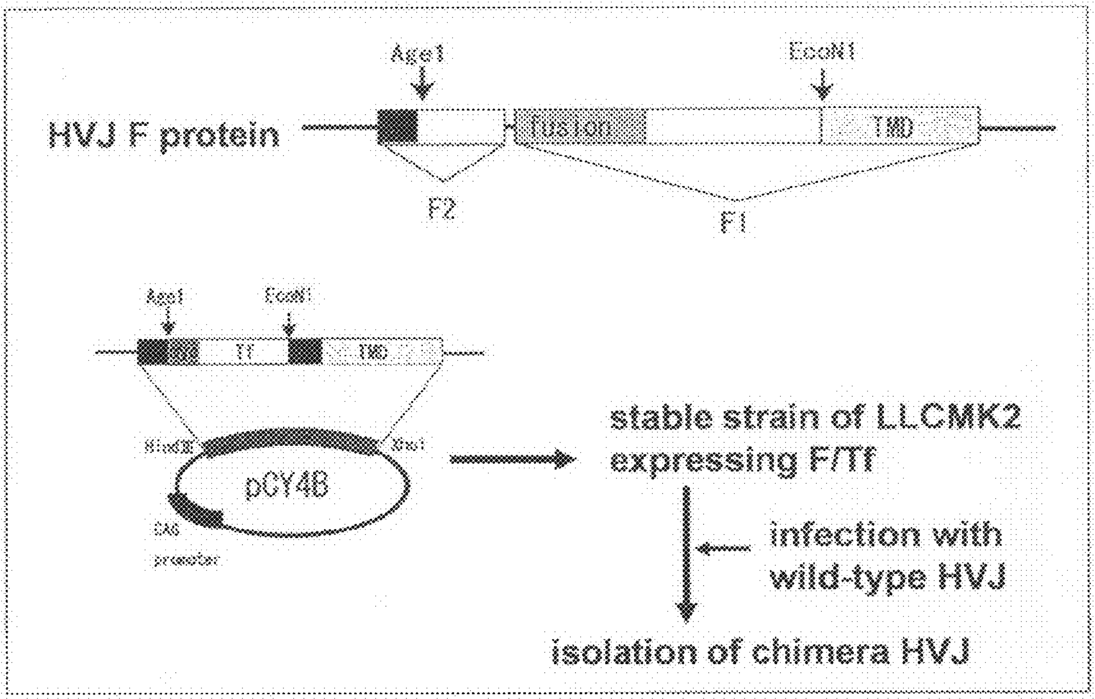
FIG. 21 shows the preparation of a chimera F/Tf gene expression vector.

(1) Preparation of HVJ Presenting Transferrin on the Virus Particle Surface Thereof, and Exhibiting a Reduced Expression of HN Protein As shown in FIG. 21, gene that encodes the F protein of HVJ was modified, and inserted into the expression plasmid pCY4B. To express a fusion protein of the transmembrane domain (TMD) of the F protein and human transferrin wherein human transferrin has been joined to the N-terminus side of the TMD, recombinant pCY4B was constructed. cDNA of human transferrin is shown by SEQ ID NO:22. In this operation, an insertion site was designed for the myc tag to attach to the N-terminus of the fusion protein to facilitate subsequent analysis. The sequence of the fusion protein inserted here is shown by SEQ ID NO:25.

In the amino acid sequence shown by SEQ ID NO:25, amino acid numbers 1 to 29 correspond to the signal sequence of HVJ-derived F protein, amino acid numbers 30 to 39 correspond to the myc tag, amino acid numbers 40 to 718 correspond to the amino acid sequence of human transferrin, and amino acid numbers 719 to 797 correspond to the amino acid sequence of the transmembrane domain of HVJ-derived F protein.

This pCY4B for expression of the fusion protein of F protein TMD and human transferrin (F/Tf), having the myc tag attached thereto, was introduced into LLCMK2 cells, and persistently transformant cells that persistently produce F/Tf protein were isolated.

Figure 22:
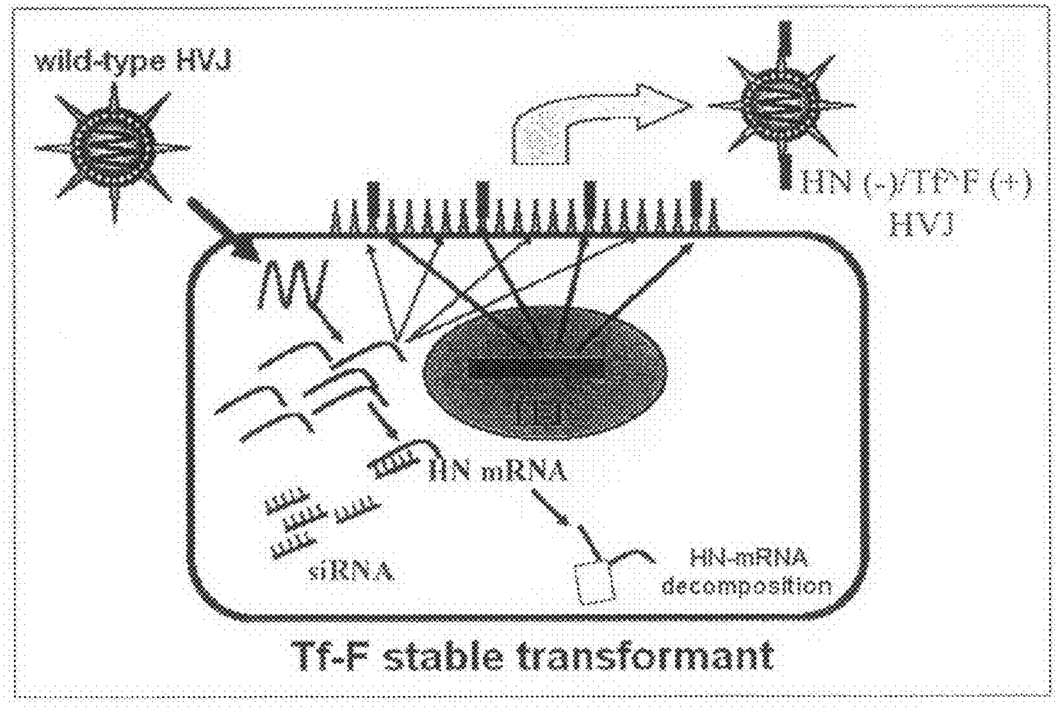
FIG. 22 shows the preparation of HVJ expressing F/Tf protein, and lacking HN protein.

HVJ virus particles produced by the transformant cells infected with wild-type HVJ to cause replication, and released outside the cells would have F/Tf, in addition to native F protein, on the surface thereof (F/Tf chimera virus), with the transferrin portion being presented outside the particles (FIG. 22).

Furthermore, to delete the HN protein from the HVJ virus produced by the cell, in the same manner as Example 1, the expression of the HN gene was suppressed by the siRNA method.

Thus, the virus produced would have transferrin presented on the virus particle surface thereof, and also have the expression of HN protein reduced remarkably or completely deleted.

Figure 23:
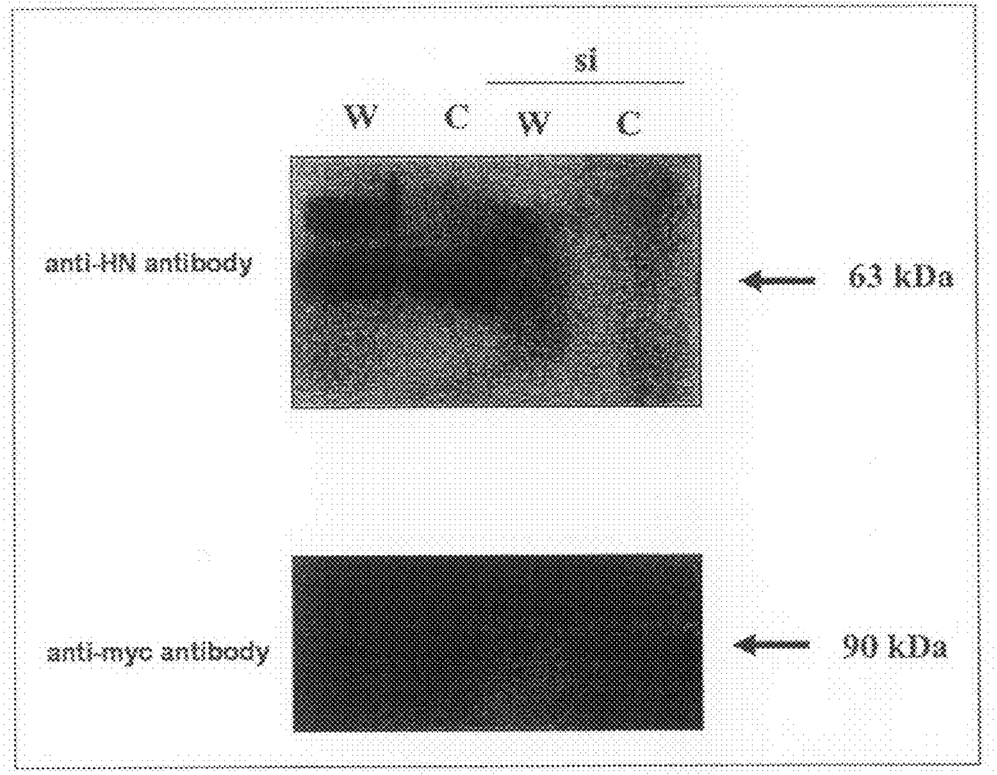
FIG. 23 is a drawing of the detection of the expression of HN protein and F/Tf protein by Western blotting. The upper panel shows HN protein, and the lower panel shows F/Tf protein. W: wild-type virus, C: chimera virus, si: siRNA treatment.

In fact, when the virus produced by the cell was recovered from the medium, and subjected to Western blotting with anti-HN antibody by a conventional method, the HN protein was not detected in the virus recovered from siRNA-treated cells, which lacked the HN protein (FIG. 23, upper panel).

Furthermore, when viruses were subjected to Western blotting with anti-myc antibody by a conventional method, the HVJ virus produced by LLCMK2 cells transformed with F/Tf expression pCY4B exhibited an anti-myc-antibody-positive protein as expected, whereas the HVJ virus produced by wild-type LLCMK2 cells being the negative control had no anti-myc-antibody-positive protein detected therein (FIG. 23, lower panel).

This result showed that HVJ virus produced by LLCMK2 cells transformed with F/Tf expression pCY4B had F/Tf protein.

(2) Experiments of Infection of HVJ to Cultured Cells

Subsequently, the infectivity of the virus produced in (1) was examined.

Figure 24:
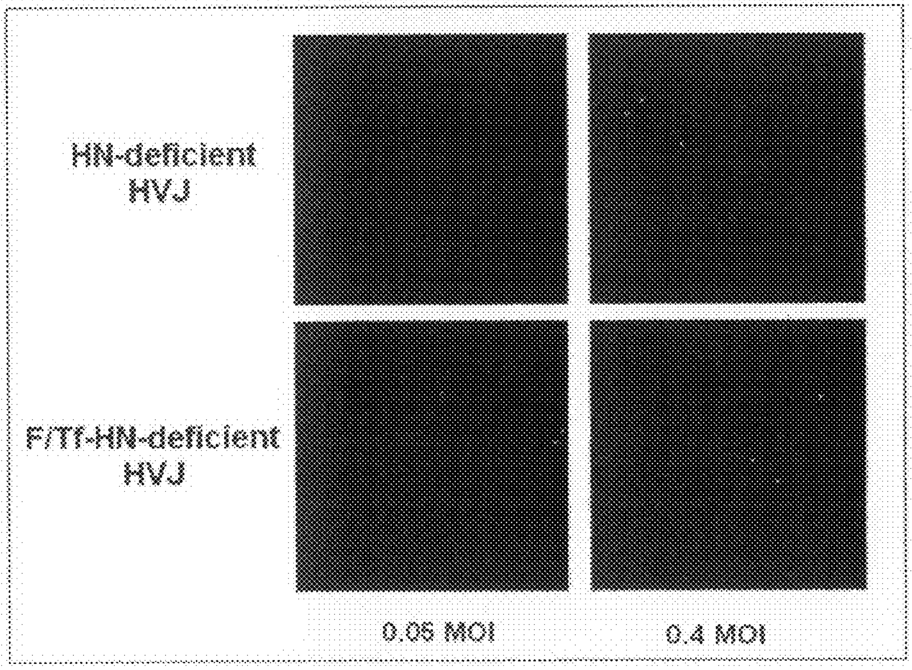
FIG. 24 is a drawing showing the infection of HN-deficient HVJ or F/Tf-HN-deficient HVJ to HEK293 cells with the expression of F protein as the index.

An HVJ lacking HN protein (HN-deficient HVJ) and an HVJ lacking HN protein, and having F/Tf (F/Tf-HN-deficient HVJ), was each infected to HEK293 cells being non-cancer cells at 0.05 MOI or 0.4 MOI, and detection of the expression of F protein was attempted using anti-F protein antibody. As a result, whichever HVJs were infected, F protein-positive cells were observed only in a very small number of cells (FIG. 24).

Figure 25:
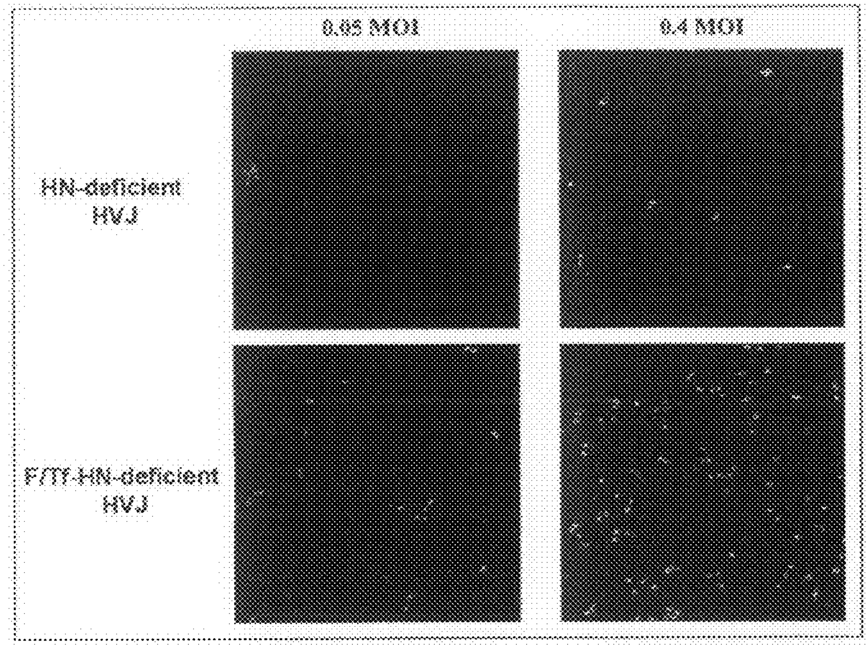
FIG. 25 is a drawing of the infection of HN-deficient HVJ or F/Tf-HN-deficient HVJ to Hela cells with the expression of F protein as the index.
Figure 26:
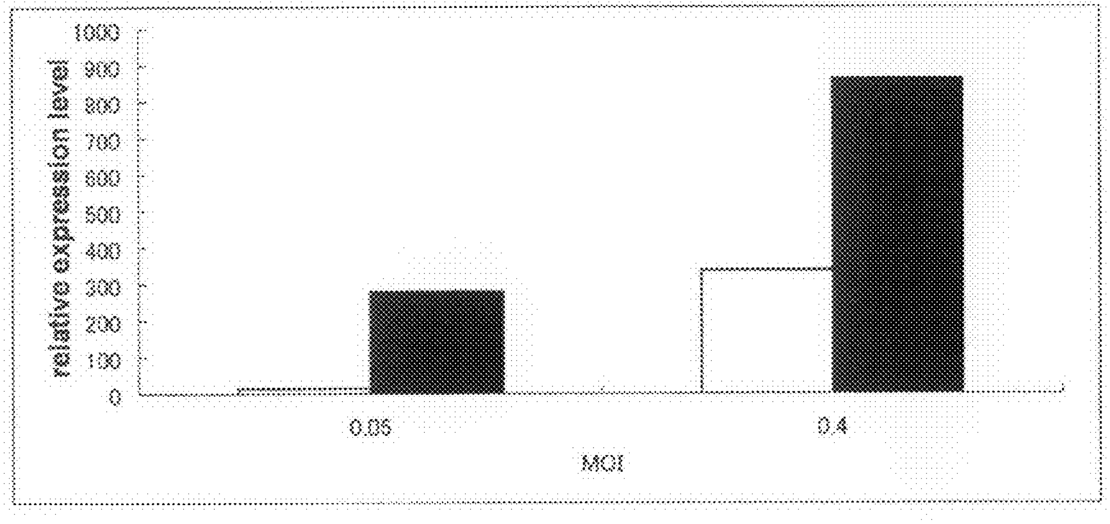
FIG. 26 is a graph showing the infection of wild-type HVJ or F/Tf-HN-deficient HVJ to Hela cells with F protein-positive cell count as the index. The outlined column shows wild-type HVJ, and the solid column shows F/Tf-HN-deficient HVJ.

Meanwhile, when each virus was infected to human uterine cervical cancer derived Hela cells in the same manner (FIG. 25), the cells infected with F/Tf-HN-deficient HVJ (lower panel) had a remarkably larger number of cells having F protein on the cell surface thereof compared with the HN-deficient HVJ lacking HN protein and not having F/Tf (upper panel). These F protein-positive cells were counted, and the results are graphed (FIG. 26).

From these results, it was found that F/Tf-HN-deficient HVJ virus, which lacked HN protein, but having F/Tf, infected specifically to cancer cells.

(3) Confirmation of Transferrin Dependency

Figure 27:
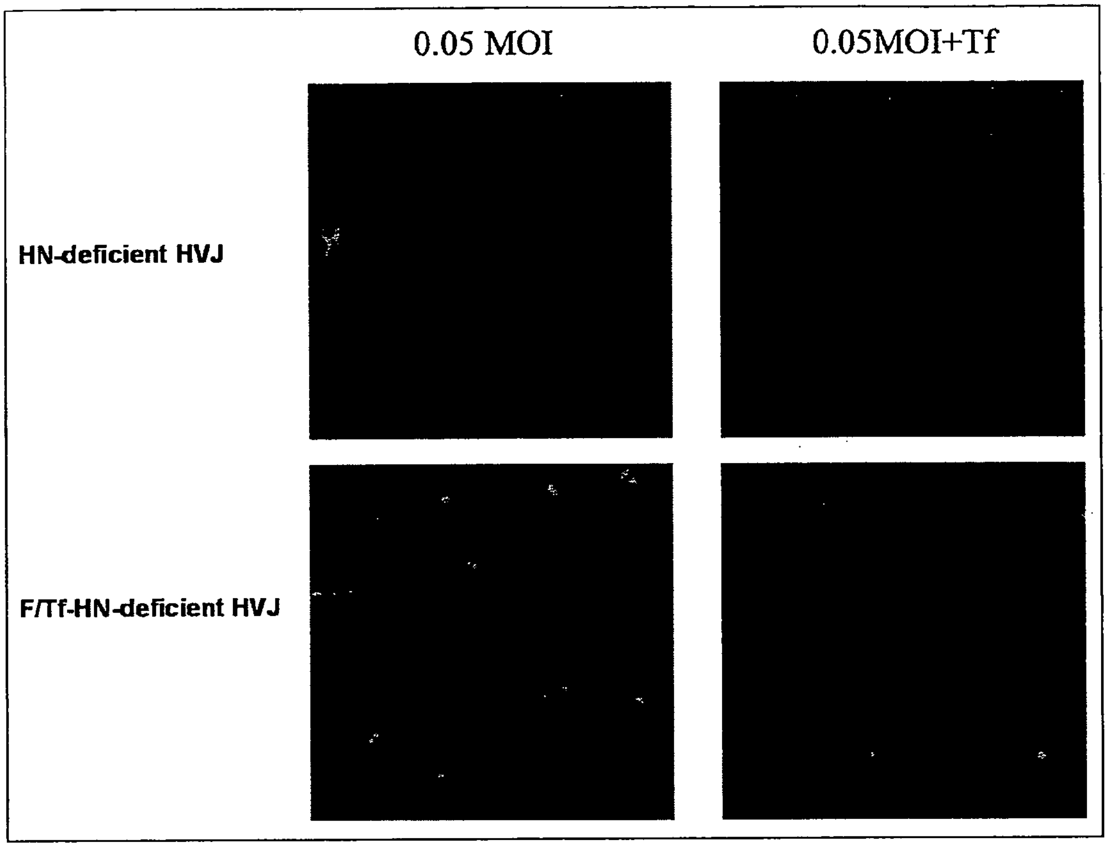
FIG. 27 shows the inhibition of the viral infection of F/Tf-HN-deficient HVJ to Hela cells by transferrin. Tf: transferrin.
Figure 28:
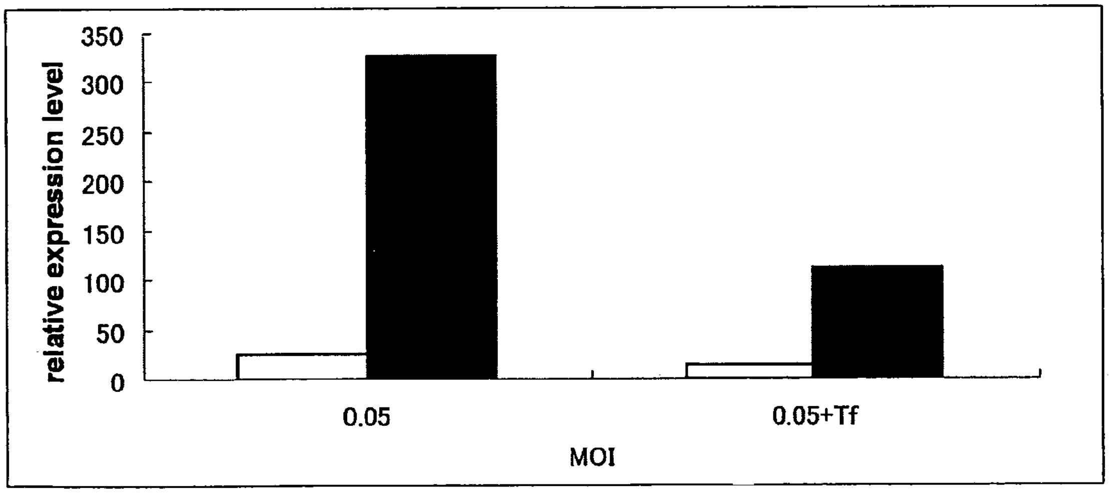
FIG. 28 is a graph showing viral infection of F/Tf-HN-deficient HVJ to Hela cells, with F protein-positive cell count as the index. The outlined column shows wild-type HVJ, and the solid column shows F/Tf-HN-deficient HVJ.

To demonstrate that the strength of the infectivity of F/Tf-HN-deficient HVJ virus to cancer cells depends on the transferrin portion contained in the F/Tf protein, Tf-HN-deficient HVJ was infected to Hela cells at 0.05 MOI in the presence of transferrin (200 μg/ml). As a result, in the presence of Tf, compared with in the absence of Tf, F protein-positive cells decreased definitely (FIG. 27 lower panel, and FIG. 28), demonstrating that infection with F/Tf-HN-deficient HVJ was inhibited by the presence of transferrin.

From this result, the infectivity of F/Tf-HN-deficient HVJ to cancer cells depended on the transferrin of F/Tf protein.

(4) In Vivo Cancer-Specific Delivery Study Using Qdot (Registered Trademark) Fluorescent Particles Cancer cell specific targeting by F/Tf-HN-deficient HVJ envelope wherein the genome of F/Tf-HN-deficient HVJ had been inactivated was tested in vivo. F/Tf-HN-deficient HVJ was exposed to UV to deactivate the genome thereof to yield an F/Tf-HN-deficient HVJ envelope. This was suspended in 1000 HAU/200 μl PBS, Qdot (registered trademark) 605ITK (trademark) Carboxyl Quantum Dot was added to obtain a final concentration of 1 μM, and the suspension was subjected to electroporation (250 V, 950 μF) to enclose Qdot (registered trademark) fluorescent particle in the envelope. Immediately after the electroporation, 1 ml of DMEM was added, the mixture was gently centrifuged, and aggregated particles were removed, after which centrifugation was performed at high speed at 20400×g for 15 minutes, and the pellets were recovered and suspended in 500 μl of physiological saline. The Qdot-enclosed HVJ envelope obtained was added to Hela cell culture medium. This was subjected to fluorescence detection; fluorescence from Qdot was observed on the cell membrane (data not shown), demonstrating the adsorption of HVJ-E to the cell surface.

Using this Qdot-enclosed F/Tf-HN-deficient HVJ-envelope, cancer-specific targeting by F/Tf-HN-deficient HVJ-envelope in vivo was examined.

Figure 29:
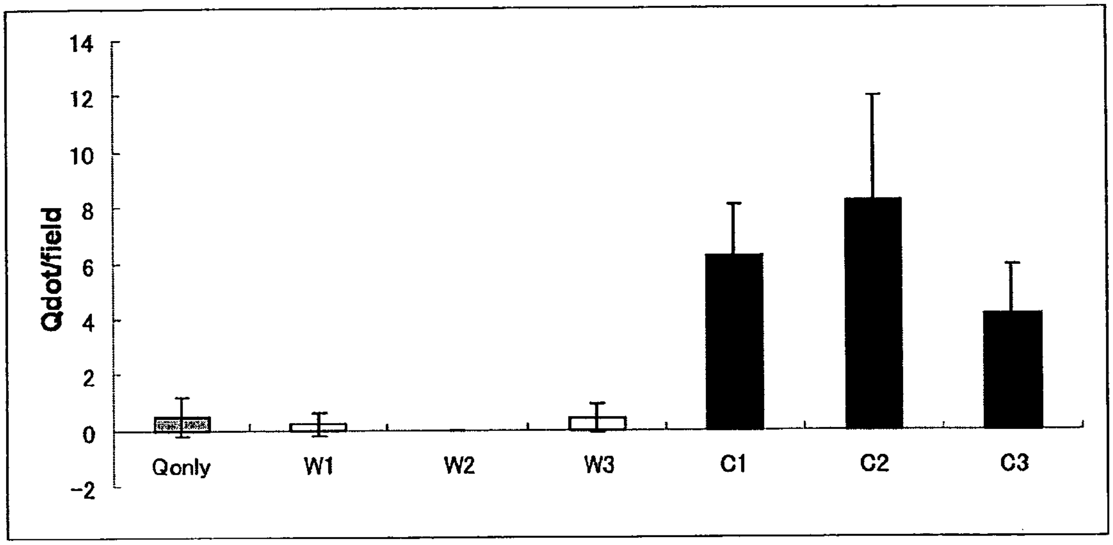
FIG. 29 is a graph showing cancer-specific targeting of F/Tf-HN-deficient HVJ-envelope. W: virus envelope prepared from wild-type HVJ virus having Qdot enclosed therein. C: F/Tf-HN-deficient HVJ virus envelope having Qdot enclosed therein. Three independent experiments were performed.

Hela cells ($5\times10^6$) were transplanted to nude mice by subcutaneous injection; when the cancer tissue became 7 to 8 mm in diameter, 500 HAU of Qdot-enclosed F/Tf-HN-deficient HVJ-envelope was injected to the tail vein. After 48 hours, mouse was fixed in para-formaldehyde, and extensively examined for Qdot distribution. Only in transplanted cancer tissue of a mouse injected with Qdot-enclosed F/Tf-HN-deficient HVJ-envelope, fluorescence from Qdot was observed, whereas when Qdot-enclosed HN-deficient HVJ-envelope having no F/Tf protein was injected, no fluorescence was observed in the cancer tissue. When the cancer tissue was examined by fluorescence microscopy, and Qdot-positive cells in each field were counted; the results are shown in FIG. 29. Compared with a case where HVJ-E was not used and Qdot alone was injected (Q only) and a case where Qdot-enclosed HN-deficient HVJ-envelope not having F/Tf protein was used (W1 to 3), when F/Tf-HN-deficient HVJ-envelope was used, Qdot-positive cells were observed at levels not less than about 30 times.

From this result, it was suggested that F/Tf-HN-deficient HVJ-envelope be targeted specifically to cancer.

INDUSTRIAL APPLICABILITY

Because the modified paramyxovirus of the present invention has a reduced amount of receptor-binding protein, and is capable of mitigating the adverse effects of the receptor-binding protein on target cells, and the like, the same can be utilized as a highly safe vector. Adding a target molecule, such as a polypeptide, that binds specifically to a marker protein being expressed on the target cell surface to the modified paramyxovirus, the paramyxovirus can be utilized as a vector with high specificity and safety. Furthermore, the method of preparing a modified paramyxovirus according to the present invention makes it possible to obtain a modified paramyxovirus conveniently and stably. By applying the method, it is possible to easily obtain a mutant virus wherein a particular virus function has been knocked out.

A paramyxovirus having the chimera protein or protein conjugate of the present invention possesses high tissue and cell specificity, and is useful as a vector capable of site-specific delivery of a drug. It is also possible to make a more specific viral vector by deleting another fusion protein, which is expected to find applications for disease treatment. According to the method of the present invention for preparing a targeting paramyxovirus, it is possible to obtain the targeting paramyxovirus conveniently and stably.

This application is based on patent application Nos. 2005-338449 filed in Japan (filing date: Nov. 24, 2005) and 2005-339474 filed in Japan (filing date: Nov. 24, 2005), the contents of which are incorporated in full herein by this reference.

The invention claimed is:

1. A chimera protein, wherein a peptide capable of binding specifically to a desired cell surface molecule is joined, directly or via a peptide linker, to the N-terminus side of the transmembrane domain of F protein derived from a paramyxovirus consisting of the amino acid sequence shown by SEQ ID NO: 11 or an amino acid sequence having a homology of 90% or more thereto and having an activity mediating fusion of the paramyxovirus and the cell, wherein the desired cell surface molecule is selected from a group consisting of desmoglein 3, β2 integrin, α4 integrin, αIIbβ3 integrin, folic acid receptor, transferrin receptor, HER2, epidermal growth factor receptor (EGFR), Low-density lipoprotein receptor (LDLR), CD20, carcinoembryonic antigen (CEA), glycoprotein 100 (Gp100), Prostate Specific Membrane Antigen (PSMA), and α-fetoprotein (AFP).

2. The chimera protein of claim 1, wherein a signal peptide selected from the group consisting of a signal peptide derived from F protein and signal peptides capable of functioning in mammalian cells is further added to the N-terminal side directly or via a linker peptide.

3. The chimera protein of claim 2, wherein the signal peptide is selected from the amino acid sequence shown by amino acid numbers 1 to 25 or 1 to 29 in the amino acid sequence shown by SEQ ID NO:11.

4. The chimera protein of claim 1, wherein the paramyxovirus is HVJ.

5. The chimera protein of claim 1, wherein the transmembrane domain consists of the amino acid sequence shown by amino acid numbers 490 to 565 or 487 to 565 in the amino acid sequence shown by SEQ ID NO: 11.

6. The chimera protein of claim 1, wherein the peptide that binds specifically to the cell surface molecule is a single-chain antibody against the molecule.

7. The chimera protein of claim 6, wherein the single-chain antibody is an antibody against desmoglein 3.

8. The chimera protein of claim 1, which consists of the amino acid sequence shown by SEQ ID NO:21.

9. The chimera protein of claim 1, which is capable of having its signal peptide cleaved by processing, incorporating in virus particles, and of binding the virus particles to desmoglein 3.

10. The chimera protein of claim 1, wherein the peptide that binds specifically to the cell surface molecule is transferrin.

11. The chimera protein of claim 1, comprising the amino acid sequence shown by amino acid numbers 40 to 797 in the amino acid sequence shown by SEQ ID NO:25.

12. The chimera protein of claim 1, which is capable of incorporating in virus particles, and of binding the virus particles to the transferrin receptor.

13. A nucleic acid that encodes the chimera protein of claim 1.

14. The nucleic acid of claim 13, consisting of the base sequence (1) or (2) below:

(1) the base sequence shown by SEQ ID NO: 20, (2) a base sequence having a homology of 90% or more to the base sequence shown by SEQ ID NO: 20, and encoding a protein having a function for a transmembrane domain, and capable of binding to desmoglein 3.

15. An isolated animal cell comprising the nucleic acid of claim 13 in an expressible form, and capable of expressing a peptide capable of binding specifically to a desired cell surface molecule in the chimera protein encoded by the nucleic acid on the cell surface.

16. A modified paramyxovirus that presents a peptide capable of binding specifically to a desired cell surface molecule in the chimera protein of claim 1 on the virus particle surface.

17. The modified paramyxovirus of claim 16, which is HVJ.

18. The modified paramyxovirus of claim 17, wherein FIN protein is reduced or lacked compared with the wild type.

19. A virus envelope vector prepared from the virus of claim 16.

20. A method of preparing a tissue targeting paramyxovirus, comprising the steps (1) to (3) below:

(1) introducing a nucleic acid that encodes a chimera protein wherein a linker peptide consisting of 0 to 30 residues has been joined to the N-terminus side of the transmembrane domain of F protein derived from paramyxovirus consisting of the amino acid sequence shown by SEQ ID NO: 11 or an amino acid sequence having a homology of 90% or more thereto and having an activity mediating fusion of the paramyxovirus and the cell, and a peptide capable of binding specifically to a desired cell surface molecule has been joined to the N-terminus thereof, into a specified animal cell in a form allowing the expression of the chimera protein on the cell membrane of the cell, (2) infecting the paramyxovirus to the cell, (3) isolating paramyxovirus particles replicated in the cell.

21. The method of claim 20, wherein the nucleic acid is placed under the control of a promoter capable of functioning in an animal cell, and a nucleic acid that encodes a signal peptide capable of functioning in the cell is added thereto.

22. The method of claim 20, wherein the paramyxovirus is HVJ.

* * * * *

UNITED STATES PATENT AND TRADEMARK OFFICE

CERTIFICATE OF CORRECTION

PATENT NO. : 7,858,356 B2
APPLICATION NO. : 12/085355
DATED : December 28, 2010
INVENTOR(S) : Kaneda et al.

It is certified that error appears in the above-identified patent and that said Letters Patent is hereby corrected as shown below:

In column 70, claim 18, lines 10-11, "FIN protein" should read --HN protein--.

Signed and Sealed this
Twenty-sixth Day of April, 2011

David J. Kappos
*Director of the United States Patent and Trademark Office*

SEQUENCE LISTING

```
<160> NUMBER OF SEQ ID NOS: 25

<210> SEQ ID NO 1
<211> LENGTH: 19
<212> TYPE: RNA
<213> ORGANISM: Sendai virus

<400> SEQUENCE: 1

gcauugaaca ugagcagca                                    19


<210> SEQ ID NO 2
<211> LENGTH: 19
<212> TYPE: RNA
<213> ORGANISM: Sendai virus

<400> SEQUENCE: 2

gaacaaaaac agcagggau                                    19


<210> SEQ ID NO 3
<211> LENGTH: 19
<212> TYPE: RNA
<213> ORGANISM: Sendai virus

<400> SEQUENCE: 3

gaacuaaguc ucaccggua                                    19


<210> SEQ ID NO 4
<211> LENGTH: 19
<212> TYPE: RNA
<213> ORGANISM: Sendai virus

<400> SEQUENCE: 4

gcgugaucau ccaggucaa                                    19
```

-continued

<210> SEQ ID NO 5
<211> LENGTH: 19
<212> TYPE: RNA
<213> ORGANISM: Sendai virus

<400> SEQUENCE: 5
gcguauacac ugaugcuua 19

<210> SEQ ID NO 6
<211> LENGTH: 19
<212> TYPE: RNA
<213> ORGANISM: Artificial
<220> FEATURE:
<223> OTHER INFORMATION: scramble siRNA

<400> SEQUENCE: 6
gcgcgcuuug uaggauucg 19

<210> SEQ ID NO 7
<211> LENGTH: 23
<212> TYPE: DNA
<213> ORGANISM: Artificial
<220> FEATURE:
<223> OTHER INFORMATION: primer

<400> SEQUENCE: 7
ggcatagaag gttactgcca gaa 23

<210> SEQ ID NO 8
<211> LENGTH: 24
<212> TYPE: DNA
<213> ORGANISM: Artificial
<220> FEATURE:
<223> OTHER INFORMATION: primer

<400> SEQUENCE: 8
tgtcacggct atagcttgat tgtc 24

<210> SEQ ID NO 9
<211> LENGTH: 17
<212> TYPE: DNA
<213> ORGANISM: Artificial
<220> FEATURE:
<223> OTHER INFORMATION: probe

<400> SEQUENCE: 9
atccacctag cagctgt 17

<210> SEQ ID NO 10
<211> LENGTH: 1698
<212> TYPE: DNA
<213> ORGANISM: Sendai virus
<220> FEATURE:
<221> NAME/KEY: CDS
<222> LOCATION: (1)..(1698)

<400> SEQUENCE: 10

```
atg gta gca tat atc cag aga tca cag tgc atc tca aca tca cta ctg       48
Met Val Ala Tyr Ile Gln Arg Ser Gln Cys Ile Ser Thr Ser Leu Leu
1               5                   10                  15

gtt gtt ctc acc aca ttg gtc tcg tgt cag att acc ggt gat agg ctc       96
Val Val Leu Thr Thr Leu Val Ser Cys Gln Ile Thr Gly Asp Arg Leu
            20                  25                  30

tct aac ata ggg gtc ata gtc gat gaa ggg aaa tca ctg aag ata gct      144
```

-continued

```
Ser Asn Ile Gly Val Ile Val Asp Glu Gly Lys Ser Leu Lys Ile Ala
        35                  40                  45

gga tcc cac gaa tcg agg tac ata gta ctg agt cta gtt ccg ggg gta      192
Gly Ser His Glu Ser Arg Tyr Ile Val Leu Ser Leu Val Pro Gly Val
    50                  55                  60

gac ttt gag aat ggg tgc gga aca gcc cag gtt atc cag tac aag agc      240
Asp Phe Glu Asn Gly Cys Gly Thr Ala Gln Val Ile Gln Tyr Lys Ser
65                  70                  75                  80

cta ctg aac agg ctg tta atc cca ttg agg gat gcc tta gat tta cag      288
Leu Leu Asn Arg Leu Leu Ile Pro Leu Arg Asp Ala Leu Asp Leu Gln
                85                  90                  95

gag gct ctg ata act gtc acc aat gat acg aca caa aat gcc ggt gct      336
Glu Ala Leu Ile Thr Val Thr Asn Asp Thr Thr Gln Asn Ala Gly Ala
            100                 105                 110

cca cag tcg aga tct ttc ggt gct gtg att ggt act atc gca ctt gga      384
Pro Gln Ser Arg Ser Phe Gly Ala Val Ile Gly Thr Ile Ala Leu Gly
        115                 120                 125

gtg gcg aca tca gca caa atc acc gca ggg att gca cta gcc gaa gcg      432
Val Ala Thr Ser Ala Gln Ile Thr Ala Gly Ile Ala Leu Ala Glu Ala
    130                 135                 140

agg gag gcc aaa aga gac ata gcg ctc atc aaa gaa tcg atg aca aaa      480
Arg Glu Ala Lys Arg Asp Ile Ala Leu Ile Lys Glu Ser Met Thr Lys
145                 150                 155                 160

aca cac aag tct ata gaa ctg ctg caa aac gct gtg ggg gaa caa att      528
Thr His Lys Ser Ile Glu Leu Leu Gln Asn Ala Val Gly Glu Gln Ile
                165                 170                 175

ctt gct cta aag aca ctc cag gat ttc gtg aat gat gag atc aaa ccc      576
Leu Ala Leu Lys Thr Leu Gln Asp Phe Val Asn Asp Glu Ile Lys Pro
            180                 185                 190

gca ata agc gaa tta ggc tgt gag act gct gcc tta aga ctg ggt ata      624
Ala Ile Ser Glu Leu Gly Cys Glu Thr Ala Ala Leu Arg Leu Gly Ile
        195                 200                 205

aaa ttg aca cag cat tac tcc gag ctg tta act gcg ttc ggc tcg aat      672
Lys Leu Thr Gln His Tyr Ser Glu Leu Leu Thr Ala Phe Gly Ser Asn
    210                 215                 220

ttc gga acc atc gga gag aag agc ctc acg ctg cag gcg ctg tct tca      720
Phe Gly Thr Ile Gly Glu Lys Ser Leu Thr Leu Gln Ala Leu Ser Ser
225                 230                 235                 240

ctt tac tct gct aac att act gag att atg acc aca atc agg aca ggg      768
Leu Tyr Ser Ala Asn Ile Thr Glu Ile Met Thr Thr Ile Arg Thr Gly
                245                 250                 255

cag tct aac atc tat gat gtc att tat aca gaa cag atc aaa gga acg      816
Gln Ser Asn Ile Tyr Asp Val Ile Tyr Thr Glu Gln Ile Lys Gly Thr
            260                 265                 270

gtg ata gat gtg gat cta gag aga tac atg gtc acc ctg tct gtg aag      864
Val Ile Asp Val Asp Leu Glu Arg Tyr Met Val Thr Leu Ser Val Lys
        275                 280                 285

atc cct att ctt tct gaa gtc cca ggt gtg ctc ata cac aag gca tca      912
Ile Pro Ile Leu Ser Glu Val Pro Gly Val Leu Ile His Lys Ala Ser
    290                 295                 300

tct att tct tac aac ata gac ggg gag gaa tgg tat gtg att gtc ccc      960
Ser Ile Ser Tyr Asn Ile Asp Gly Glu Glu Trp Tyr Val Ile Val Pro
305                 310                 315                 320

agc cat ata ctc agt cgt gct tct ttc tta ggg ggt gca gac ata acc     1008
Ser His Ile Leu Ser Arg Ala Ser Phe Leu Gly Gly Ala Asp Ile Thr
                325                 330                 335

gat tgt gtt gag tcc aga ttg acc tat ata tgc ccc agg gat ccc gca     1056
Asp Cys Val Glu Ser Arg Leu Thr Tyr Ile Cys Pro Arg Asp Pro Ala
            340                 345                 350
```

-continued

```
caa ctg ata cct gac agc cag caa aag tgt atc ctg ggg gac aca aca      1104
Gln Leu Ile Pro Asp Ser Gln Gln Lys Cys Ile Leu Gly Asp Thr Thr
        355                 360                 365

aga tgt cct gtc aca aaa gtt gtg gac agc ctt atc ccc aag ttt gct      1152
Arg Cys Pro Val Thr Lys Val Val Asp Ser Leu Ile Pro Lys Phe Ala
    370                 375                 380

ttt gtg aat ggg ggc gtt gtt gct aac tgc ata gca tcc aca tgt acc      1200
Phe Val Asn Gly Gly Val Val Ala Asn Cys Ile Ala Ser Thr Cys Thr
385                 390                 395                 400

tgc ggg aca ggc cga aga cca atc agt cag gat cgc tct aaa ggt gta      1248
Cys Gly Thr Gly Arg Arg Pro Ile Ser Gln Asp Arg Ser Lys Gly Val
                405                 410                 415

gta ttc cta acc cat gac aac tgt ggt ctt ata ggt gtc aat ggg gta      1296
Val Phe Leu Thr His Asp Asn Cys Gly Leu Ile Gly Val Asn Gly Val
            420                 425                 430

gaa ttg tat gct aac cgg aga ggg cac gat gcc act tgg ggg gtc cag      1344
Glu Leu Tyr Ala Asn Arg Arg Gly His Asp Ala Thr Trp Gly Val Gln
        435                 440                 445

aac ttg aca gtc ggt cct gca att gct atc aga ccc att gat att tct      1392
Asn Leu Thr Val Gly Pro Ala Ile Ala Ile Arg Pro Ile Asp Ile Ser
    450                 455                 460

ctc aac ctt gct gat gct acg aat ttc ttg caa gac tct aag gct gag      1440
Leu Asn Leu Ala Asp Ala Thr Asn Phe Leu Gln Asp Ser Lys Ala Glu
465                 470                 475                 480

ctt gag aaa gca cgg aaa atc ctc tcg gag gta ggt aga tgg tac aac      1488
Leu Glu Lys Ala Arg Lys Ile Leu Ser Glu Val Gly Arg Trp Tyr Asn
                485                 490                 495

tca aga gag act gtg att acg atc ata gta gtt atg gtc gta ata ttg      1536
Ser Arg Glu Thr Val Ile Thr Ile Ile Val Val Met Val Val Ile Leu
            500                 505                 510

gtg gtc att ata gtg atc atc atc gtg ctt tat aga ctc aga agg tca      1584
Val Val Ile Ile Val Ile Ile Ile Val Leu Tyr Arg Leu Arg Arg Ser
        515                 520                 525

atg cta atg ggt aat cca gat gac cgt ata ccg agg gac aca tac aca      1632
Met Leu Met Gly Asn Pro Asp Asp Arg Ile Pro Arg Asp Thr Tyr Thr
    530                 535                 540

tta gag ccg aag atc aga cat atg tac aca aac ggt ggg ttt gat gca      1680
Leu Glu Pro Lys Ile Arg His Met Tyr Thr Asn Gly Gly Phe Asp Ala
545                 550                 555                 560

atg gct gag aaa aga tga                                              1698
Met Ala Glu Lys Arg
                565


<210> SEQ ID NO 11
<211> LENGTH: 565
<212> TYPE: PRT
<213> ORGANISM: Sendai virus

<400> SEQUENCE: 11

Met Val Ala Tyr Ile Gln Arg Ser Gln Cys Ile Ser Thr Ser Leu Leu
1               5                   10                  15

Val Val Leu Thr Thr Leu Val Ser Cys Gln Ile Thr Gly Asp Arg Leu
            20                  25                  30

Ser Asn Ile Gly Val Ile Val Asp Glu Gly Lys Ser Leu Lys Ile Ala
        35                  40                  45

Gly Ser His Glu Ser Arg Tyr Ile Val Leu Ser Leu Val Pro Gly Val
    50                  55                  60

Asp Phe Glu Asn Gly Cys Gly Thr Ala Gln Val Ile Gln Tyr Lys Ser
65                  70                  75                  80
```

-continued

```
Leu Leu Asn Arg Leu Leu Ile Pro Leu Arg Asp Ala Leu Asp Leu Gln
                85                  90                  95

Glu Ala Leu Ile Thr Val Thr Asn Asp Thr Thr Gln Asn Ala Gly Ala
            100                 105                 110

Pro Gln Ser Arg Ser Phe Gly Ala Val Ile Gly Thr Ile Ala Leu Gly
        115                 120                 125

Val Ala Thr Ser Ala Gln Ile Thr Ala Gly Ile Ala Leu Ala Glu Ala
    130                 135                 140

Arg Glu Ala Lys Arg Asp Ile Ala Leu Ile Lys Glu Ser Met Thr Lys
145                 150                 155                 160

Thr His Lys Ser Ile Glu Leu Leu Gln Asn Ala Val Gly Glu Gln Ile
                165                 170                 175

Leu Ala Leu Lys Thr Leu Gln Asp Phe Val Asn Asp Glu Ile Lys Pro
            180                 185                 190

Ala Ile Ser Glu Leu Gly Cys Glu Thr Ala Ala Leu Arg Leu Gly Ile
        195                 200                 205

Lys Leu Thr Gln His Tyr Ser Glu Leu Leu Thr Ala Phe Gly Ser Asn
    210                 215                 220

Phe Gly Thr Ile Gly Glu Lys Ser Leu Thr Leu Gln Ala Leu Ser Ser
225                 230                 235                 240

Leu Tyr Ser Ala Asn Ile Thr Glu Ile Met Thr Thr Ile Arg Thr Gly
                245                 250                 255

Gln Ser Asn Ile Tyr Asp Val Ile Tyr Thr Glu Gln Ile Lys Gly Thr
            260                 265                 270

Val Ile Asp Val Asp Leu Glu Arg Tyr Met Val Thr Leu Ser Val Lys
        275                 280                 285

Ile Pro Ile Leu Ser Glu Val Pro Gly Val Leu Ile His Lys Ala Ser
    290                 295                 300

Ser Ile Ser Tyr Asn Ile Asp Gly Glu Glu Trp Tyr Val Ile Val Pro
305                 310                 315                 320

Ser His Ile Leu Ser Arg Ala Ser Phe Leu Gly Gly Ala Asp Ile Thr
                325                 330                 335

Asp Cys Val Glu Ser Arg Leu Thr Tyr Ile Cys Pro Arg Asp Pro Ala
            340                 345                 350

Gln Leu Ile Pro Asp Ser Gln Gln Lys Cys Ile Leu Gly Asp Thr Thr
        355                 360                 365

Arg Cys Pro Val Thr Lys Val Val Asp Ser Leu Ile Pro Lys Phe Ala
    370                 375                 380

Phe Val Asn Gly Gly Val Val Ala Asn Cys Ile Ala Ser Thr Cys Thr
385                 390                 395                 400

Cys Gly Thr Gly Arg Arg Pro Ile Ser Gln Asp Arg Ser Lys Gly Val
                405                 410                 415

Val Phe Leu Thr His Asp Asn Cys Gly Leu Ile Gly Val Asn Gly Val
            420                 425                 430

Glu Leu Tyr Ala Asn Arg Arg Gly His Asp Ala Thr Trp Gly Val Gln
        435                 440                 445

Asn Leu Thr Val Gly Pro Ala Ile Ala Ile Arg Pro Ile Asp Ile Ser
    450                 455                 460

Leu Asn Leu Ala Asp Ala Thr Asn Phe Leu Gln Asp Ser Lys Ala Glu
465                 470                 475                 480

Leu Glu Lys Ala Arg Lys Ile Leu Ser Glu Val Gly Arg Trp Tyr Asn
                485                 490                 495

Ser Arg Glu Thr Val Ile Thr Ile Ile Val Val Met Val Val Ile Leu
```

-continued

```
            500                 505                 510

Val Val Ile Ile Val Ile Ile Ile Val Leu Tyr Arg Leu Arg Arg Ser
        515                 520                 525

Met Leu Met Gly Asn Pro Asp Asp Arg Ile Pro Arg Asp Thr Tyr Thr
    530                 535                 540

Leu Glu Pro Lys Ile Arg His Met Tyr Thr Asn Gly Gly Phe Asp Ala
545                 550                 555                 560

Met Ala Glu Lys Arg
                565


<210> SEQ ID NO 12
<211> LENGTH: 20
<212> TYPE: DNA
<213> ORGANISM: Artificial
<220> FEATURE:
<223> OTHER INFORMATION: primer

<400> SEQUENCE: 12

catggtgagc aagggcgagg                                                 20


<210> SEQ ID NO 13
<211> LENGTH: 20
<212> TYPE: DNA
<213> ORGANISM: Artificial
<220> FEATURE:
<223> OTHER INFORMATION: primer

<400> SEQUENCE: 13

ttctagatcc ggtggatccg                                                 20


<210> SEQ ID NO 14
<211> LENGTH: 22
<212> TYPE: DNA
<213> ORGANISM: Artificial
<220> FEATURE:
<223> OTHER INFORMATION: primer

<400> SEQUENCE: 14

tatggtgagc aagggcgagg ag                                              22


<210> SEQ ID NO 15
<211> LENGTH: 22
<212> TYPE: DNA
<213> ORGANISM: Artificial
<220> FEATURE:
<223> OTHER INFORMATION: primer

<400> SEQUENCE: 15

gctctagatc cggtggatcc cg                                              22


<210> SEQ ID NO 16
<211> LENGTH: 21
<212> TYPE: DNA
<213> ORGANISM: Artificial
<220> FEATURE:
<223> OTHER INFORMATION: primer

<400> SEQUENCE: 16

atctagatcc ggtggatccc g                                               21


<210> SEQ ID NO 17
<211> LENGTH: 750
<212> TYPE: DNA
<213> ORGANISM: Artificial
```

-continued

<220> FEATURE:
<223> OTHER INFORMATION: antibody

<400> SEQUENCE: 17
atggcggact acaaagatat tgtgttaaca cagtctccag ccaccctgtc tgtgactcca 60
ggagatagcg tcagtctttc ctgcagggcc agccaaagta ttagcagcaa cctacactgg 120
tatcaacaaa aatcacatga gtctccaagg cttctcatca agtatgcttc ccagtccatc 180
tctgggatcc cctccaggtt cagtgccaga ggatcaggga cagatttcac tctcagtatc 240
aacagtgtgg agactgaaga ttttggaatg tatttctgtc aacagagtga cagctggcct 300
cacacgttcg gaggggggac caagctggag ctgaaacgtg gtggtggtgg ttctggtggt 360
ggtggttctg gcggcggcgg ctccggtggt ggtggatccg aggtgaagtt ggtggagtct 420
ggtggaggat tggtgcagcc taaagggtca ttgaaactct catgtgccgc ctctggtttc 480
accttcaata cctatgccat gcactgggtc cgccaggctc caggaaaggg tttggaatgg 540
gttgctcgca taagaagtaa aagtagcaat tatgcaacat attatgccga ttcagtgaaa 600
gacagattca ccatctccag agatgattca caaagcatgc tctatctgca aatgaacaac 660
ctgaaaactg aggacacagc catgtattac tgtgtgcggg gtgcttacta ctttgactac 720
tggggccaag gcaccactct cacagtctcc 750

<210> SEQ ID NO 18
<211> LENGTH: 30
<212> TYPE: DNA
<213> ORGANISM: Artificial
<220> FEATURE:
<223> OTHER INFORMATION: primer

<400> SEQUENCE: 18
tatggcggac tacaaagata ttgtgttaac 30

<210> SEQ ID NO 19
<211> LENGTH: 17
<212> TYPE: DNA
<213> ORGANISM: Artificial
<220> FEATURE:
<223> OTHER INFORMATION: primer

<400> SEQUENCE: 19
aggagactgt gagagtg 17

<210> SEQ ID NO 20
<211> LENGTH: 1077
<212> TYPE: DNA
<213> ORGANISM: Artificial
<220> FEATURE:
<223> OTHER INFORMATION: fusion protein of Anti Dsm3 single chain
antibody and F protein TM domein
<220> FEATURE:
<221> NAME/KEY: CDS
<222> LOCATION: (1)..(1077)

<400> SEQUENCE: 20

```
atg gta gca tat atc cag aga tca cag tgc atc tca aca tca cta ctg       48
Met Val Ala Tyr Ile Gln Arg Ser Gln Cys Ile Ser Thr Ser Leu Leu
1               5                   10                  15

gtt gtt ctc acc aca ttg gtc tcg tgt cag att acc ggt atg gcg gac       96
Val Val Leu Thr Thr Leu Val Ser Cys Gln Ile Thr Gly Met Ala Asp
            20                  25                  30

tac aaa gat att gtg tta aca cag tct cca gcc acc ctg tct gtg act      144
Tyr Lys Asp Ile Val Leu Thr Gln Ser Pro Ala Thr Leu Ser Val Thr
```

-continued

```
        35                  40                  45

cca gga gat agc gtc agt ctt tcc tgc agg gcc agc caa agt att agc      192
Pro Gly Asp Ser Val Ser Leu Ser Cys Arg Ala Ser Gln Ser Ile Ser
    50                  55                  60

agc aac cta cac tgg tat caa caa aaa tca cat gag tct cca agg ctt      240
Ser Asn Leu His Trp Tyr Gln Gln Lys Ser His Glu Ser Pro Arg Leu
65                  70                  75                  80

ctc atc aag tat gct tcc cag tcc atc tct ggg atc ccc tcc agg ttc      288
Leu Ile Lys Tyr Ala Ser Gln Ser Ile Ser Gly Ile Pro Ser Arg Phe
                85                  90                  95

agt gcc aga gga tca ggg aca gat ttc act ctc agt atc aac agt gtg      336
Ser Ala Arg Gly Ser Gly Thr Asp Phe Thr Leu Ser Ile Asn Ser Val
            100                 105                 110

gag act gaa gat ttt gga atg tat ttc tgt caa cag agt gac agc tgg      384
Glu Thr Glu Asp Phe Gly Met Tyr Phe Cys Gln Gln Ser Asp Ser Trp
        115                 120                 125

cct cac acg ttc gga ggg ggg acc aag ctg gag ctg aaa cgt ggt ggt      432
Pro His Thr Phe Gly Gly Gly Thr Lys Leu Glu Leu Lys Arg Gly Gly
    130                 135                 140

ggt ggt tct ggt ggt ggt ggt tct ggc ggc ggc ggc tcc ggt ggt ggt      480
Gly Gly Ser Gly Gly Gly Gly Ser Gly Gly Gly Gly Ser Gly Gly Gly
145                 150                 155                 160

gga tcc gag gtg aag ttg gtg gag tct ggt gga gga ttg gtg cag cct      528
Gly Ser Glu Val Lys Leu Val Glu Ser Gly Gly Gly Leu Val Gln Pro
                165                 170                 175

aaa ggg tca ttg aaa ctc tca tgt gcc gcc tct ggt ttc acc ttc aat      576
Lys Gly Ser Leu Lys Leu Ser Cys Ala Ala Ser Gly Phe Thr Phe Asn
            180                 185                 190

acc tat gcc atg cac tgg gtc cgc cag gct cca gga aag ggt ttg gaa      624
Thr Tyr Ala Met His Trp Val Arg Gln Ala Pro Gly Lys Gly Leu Glu
        195                 200                 205

tgg gtt gct cgc ata aga agt aaa agt agc aat tat gca aca tat tat      672
Trp Val Ala Arg Ile Arg Ser Lys Ser Ser Asn Tyr Ala Thr Tyr Tyr
    210                 215                 220

gcc gat tca gtg aaa gac aga ttc acc atc tcc aga gat gat tca caa      720
Ala Asp Ser Val Lys Asp Arg Phe Thr Ile Ser Arg Asp Asp Ser Gln
225                 230                 235                 240

agc atg ctc tat ctg caa atg aac aac ctg aaa act gag gac aca gcc      768
Ser Met Leu Tyr Leu Gln Met Asn Asn Leu Lys Thr Glu Asp Thr Ala
                245                 250                 255

atg tat tac tgt gtg cgg ggt gct tac tac ttt gac tac tgg ggc caa      816
Met Tyr Tyr Cys Val Arg Gly Ala Tyr Tyr Phe Asp Tyr Trp Gly Gln
            260                 265                 270

ggc acc act ctc aca gtc tcc agc ctc tcg gag gta ggt aga tgg tac      864
Gly Thr Thr Leu Thr Val Ser Ser Leu Ser Glu Val Gly Arg Trp Tyr
        275                 280                 285

aac tca aga gag act gtg att acg atc ata gta gtt atg gtc gta ata      912
Asn Ser Arg Glu Thr Val Ile Thr Ile Ile Val Val Met Val Val Ile
    290                 295                 300

ttg gtg gtc att ata gtg atc atc atc gtg ctt tat aga ctc aga agg      960
Leu Val Val Ile Ile Val Ile Ile Ile Val Leu Tyr Arg Leu Arg Arg
305                 310                 315                 320

tca atg cta atg ggt aat cca gat gac cgt ata ccg agg gac aca tac     1008
Ser Met Leu Met Gly Asn Pro Asp Asp Arg Ile Pro Arg Asp Thr Tyr
                325                 330                 335

aca tta gag ccg aag atc aga cat atg tac aca aac ggt ggg ttt gat     1056
Thr Leu Glu Pro Lys Ile Arg His Met Tyr Thr Asn Gly Gly Phe Asp
            340                 345                 350

gca atg gct gag aaa aga tga                                         1077
```

-continued

```
Ala Met Ala Glu Lys Arg
        355


<210> SEQ ID NO 21
<211> LENGTH: 358
<212> TYPE: PRT
<213> ORGANISM: Artificial
<220> FEATURE:
<223> OTHER INFORMATION: fusion protein of Anti Dsm3 single chain
      antibody and F protein TM domein

<400> SEQUENCE: 21

Met Val Ala Tyr Ile Gln Arg Ser Gln Cys Ile Ser Thr Ser Leu Leu
1               5                   10                  15

Val Val Leu Thr Thr Leu Val Ser Cys Gln Ile Thr Gly Met Ala Asp
            20                  25                  30

Tyr Lys Asp Ile Val Leu Thr Gln Ser Pro Ala Thr Leu Ser Val Thr
        35                  40                  45

Pro Gly Asp Ser Val Ser Leu Ser Cys Arg Ala Ser Gln Ser Ile Ser
    50                  55                  60

Ser Asn Leu His Trp Tyr Gln Gln Lys Ser His Glu Ser Pro Arg Leu
65                  70                  75                  80

Leu Ile Lys Tyr Ala Ser Gln Ser Ile Ser Gly Ile Pro Ser Arg Phe
                85                  90                  95

Ser Ala Arg Gly Ser Gly Thr Asp Phe Thr Leu Ser Ile Asn Ser Val
            100                 105                 110

Glu Thr Glu Asp Phe Gly Met Tyr Phe Cys Gln Gln Ser Asp Ser Trp
        115                 120                 125

Pro His Thr Phe Gly Gly Gly Thr Lys Leu Glu Leu Lys Arg Gly Gly
    130                 135                 140

Gly Gly Ser Gly Gly Gly Gly Ser Gly Gly Gly Gly Ser Gly Gly Gly
145                 150                 155                 160

Gly Ser Glu Val Lys Leu Val Glu Ser Gly Gly Gly Leu Val Gln Pro
                165                 170                 175

Lys Gly Ser Leu Lys Leu Ser Cys Ala Ala Ser Gly Phe Thr Phe Asn
            180                 185                 190

Thr Tyr Ala Met His Trp Val Arg Gln Ala Pro Gly Lys Gly Leu Glu
        195                 200                 205

Trp Val Ala Arg Ile Arg Ser Lys Ser Ser Asn Tyr Ala Thr Tyr Tyr
    210                 215                 220

Ala Asp Ser Val Lys Asp Arg Phe Thr Ile Ser Arg Asp Asp Ser Gln
225                 230                 235                 240

Ser Met Leu Tyr Leu Gln Met Asn Asn Leu Lys Thr Glu Asp Thr Ala
                245                 250                 255

Met Tyr Tyr Cys Val Arg Gly Ala Tyr Tyr Phe Asp Tyr Trp Gly Gln
            260                 265                 270

Gly Thr Thr Leu Thr Val Ser Ser Leu Ser Glu Val Gly Arg Trp Tyr
        275                 280                 285

Asn Ser Arg Glu Thr Val Ile Thr Ile Ile Val Val Met Val Val Ile
    290                 295                 300

Leu Val Val Ile Ile Val Ile Ile Ile Val Leu Tyr Arg Leu Arg Arg
305                 310                 315                 320

Ser Met Leu Met Gly Asn Pro Asp Asp Arg Ile Pro Arg Asp Thr Tyr
                325                 330                 335

Thr Leu Glu Pro Lys Ile Arg His Met Tyr Thr Asn Gly Gly Phe Asp
            340                 345                 350
```

-continued

```
Ala Met Ala Glu Lys Arg
        355


<210> SEQ ID NO 22
<211> LENGTH: 2002
<212> TYPE: DNA
<213> ORGANISM: Homo sapiens
<220> FEATURE:
<221> NAME/KEY: CDS
<222> LOCATION: (1)..(2001)

<400> SEQUENCE: 22

gtc cct gat aaa act gtg aga tgg tgt gca gtg tcg gag cat gag gcc       48
Val Pro Asp Lys Thr Val Arg Trp Cys Ala Val Ser Glu His Glu Ala
1               5                   10                  15

act aag tgc cag agt ttc cgc gac cat atg aaa agc gtc att cca tcc       96
Thr Lys Cys Gln Ser Phe Arg Asp His Met Lys Ser Val Ile Pro Ser
            20                  25                  30

gat ggt ccc agt gtt gct tgt gtg aag aaa gcc tcc tac ctt gat tgc      144
Asp Gly Pro Ser Val Ala Cys Val Lys Lys Ala Ser Tyr Leu Asp Cys
        35                  40                  45

atc agg gcc att gcg gca aac gaa gcg gat gct gtg aca ctg gat gca      192
Ile Arg Ala Ile Ala Ala Asn Glu Ala Asp Ala Val Thr Leu Asp Ala
    50                  55                  60

ggt ttg gtg tat gat gct tac ctg gct ccc aat aac ctg aag cct gtg      240
Gly Leu Val Tyr Asp Ala Tyr Leu Ala Pro Asn Asn Leu Lys Pro Val
65                  70                  75                  80

gtg gca gag ttc tat ggg tca aaa gag gat cca cag act ttc tat tat      288
Val Ala Glu Phe Tyr Gly Ser Lys Glu Asp Pro Gln Thr Phe Tyr Tyr
                85                  90                  95

gct gtt gct gtg gtg aag aag gat agt ggc ttc cag atg aac cag ctt      336
Ala Val Ala Val Val Lys Lys Asp Ser Gly Phe Gln Met Asn Gln Leu
            100                 105                 110

cga ggc aag aag tcc tgc cac acg ggt cta ggc agg tcc gct ggg tgg      384
Arg Gly Lys Lys Ser Cys His Thr Gly Leu Gly Arg Ser Ala Gly Trp
        115                 120                 125

aac atc ccc ata ggc tta ctt tac tgt gac tta cct gag cca cgt aaa      432
Asn Ile Pro Ile Gly Leu Leu Tyr Cys Asp Leu Pro Glu Pro Arg Lys
    130                 135                 140

cct ctt gag aaa gca gtg gcc aat ttc ttc tcg ggc agc tgt gcc cct      480
Pro Leu Glu Lys Ala Val Ala Asn Phe Phe Ser Gly Ser Cys Ala Pro
145                 150                 155                 160

tgt gcg gat ggg acg gac ttc ccc cag ctg tgt caa ctg tgt cca ggg      528
Cys Ala Asp Gly Thr Asp Phe Pro Gln Leu Cys Gln Leu Cys Pro Gly
                165                 170                 175

tgt ggc tgc tcc acc ctt aac caa tac ttc ggc tac tca gga gcc ttc      576
Cys Gly Cys Ser Thr Leu Asn Gln Tyr Phe Gly Tyr Ser Gly Ala Phe
            180                 185                 190

aag tgt ctg aag aat ggt gct ggg gat gtg gcc ttt gtc aag cac tcg      624
Lys Cys Leu Lys Asn Gly Ala Gly Asp Val Ala Phe Val Lys His Ser
        195                 200                 205

act ata ttt gag aac ttg gca aac aag gct gac agg gac cag tat gag      672
Thr Ile Phe Glu Asn Leu Ala Asn Lys Ala Asp Arg Asp Gln Tyr Glu
    210                 215                 220

ctg ctt tgc ctg gac aac acc cgg aag ccg gta gat gaa tac aag gac      720
Leu Leu Cys Leu Asp Asn Thr Arg Lys Pro Val Asp Glu Tyr Lys Asp
225                 230                 235                 240

tgc cac ttg gcc cag gtc cct tct cat acc gtc gtg gcc cga agt atg      768
Cys His Leu Ala Gln Val Pro Ser His Thr Val Val Ala Arg Ser Met
                245                 250                 255
```

-continued

```
ggc ggc aag gag gac ttg atc tgg gag ctt ctc aac cag gcc cag gaa      816
Gly Gly Lys Glu Asp Leu Ile Trp Glu Leu Leu Asn Gln Ala Gln Glu
            260                 265                 270

cat ttt ggc aaa gac aaa tca aaa gaa ttc caa cta ttc agc tct cct      864
His Phe Gly Lys Asp Lys Ser Lys Glu Phe Gln Leu Phe Ser Ser Pro
        275                 280                 285

cat ggg aag gac ctg ctg ttt aag gac tct gcc cac ggg ttt tta aaa      912
His Gly Lys Asp Leu Leu Phe Lys Asp Ser Ala His Gly Phe Leu Lys
    290                 295                 300

gtc ccc ccc agg atg gat gcc aag atg tac ctg ggc tat gag tat gtc      960
Val Pro Pro Arg Met Asp Ala Lys Met Tyr Leu Gly Tyr Glu Tyr Val
305                 310                 315                 320

act gcc atc cgg aat cta cgg gaa ggc aca tgc caa gaa gcc cca aca     1008
Thr Ala Ile Arg Asn Leu Arg Glu Gly Thr Cys Gln Glu Ala Pro Thr
                325                 330                 335

gat gaa tgc aag cct gtg aag tgg tgt gcg ctg agc cac cac gag agg     1056
Asp Glu Cys Lys Pro Val Lys Trp Cys Ala Leu Ser His His Glu Arg
            340                 345                 350

ctc aag tgt gat gag tgg agt gtt aac agt gta ggg aaa ata gag tgt     1104
Leu Lys Cys Asp Glu Trp Ser Val Asn Ser Val Gly Lys Ile Glu Cys
        355                 360                 365

gta tca gca gag acc acc gaa gac tgc atc gcc aag atc atg aat gga     1152
Val Ser Ala Glu Thr Thr Glu Asp Cys Ile Ala Lys Ile Met Asn Gly
    370                 375                 380

gaa gct gat gcc atg agc ttg gat gga ggg ttt gtc tac ata gcg ggc     1200
Glu Ala Asp Ala Met Ser Leu Asp Gly Gly Phe Val Tyr Ile Ala Gly
385                 390                 395                 400

aag tgt ggt ctg gtg cct gtc ttg gca gaa aac tac aat aag agc gat     1248
Lys Cys Gly Leu Val Pro Val Leu Ala Glu Asn Tyr Asn Lys Ser Asp
                405                 410                 415

aat tgt gag gat aca cca gag gca ggg tat ttt gct gta gca gtg gtg     1296
Asn Cys Glu Asp Thr Pro Glu Ala Gly Tyr Phe Ala Val Ala Val Val
            420                 425                 430

aag aaa tca gct tct gac ctc acc tgg gac aat ctg aaa ggc aag aag     1344
Lys Lys Ser Ala Ser Asp Leu Thr Trp Asp Asn Leu Lys Gly Lys Lys
        435                 440                 445

tcc tgc cat acg gca gtt ggc aga acc gct ggc tgg aac atc ccc atg     1392
Ser Cys His Thr Ala Val Gly Arg Thr Ala Gly Trp Asn Ile Pro Met
    450                 455                 460

ggc ctg ctc tac aat aag atc aac cac tgc aga ttt gat gaa ttt ttc     1440
Gly Leu Leu Tyr Asn Lys Ile Asn His Cys Arg Phe Asp Glu Phe Phe
465                 470                 475                 480

agt gaa ggt tgt gcc cct ggg tct aag aaa gac tcc agt ctc tgt aag     1488
Ser Glu Gly Cys Ala Pro Gly Ser Lys Lys Asp Ser Ser Leu Cys Lys
                485                 490                 495

ctg tgt atg ggc tca ggc cta aac ctg tgt gaa ccc aac aac aaa gag     1536
Leu Cys Met Gly Ser Gly Leu Asn Leu Cys Glu Pro Asn Asn Lys Glu
            500                 505                 510

gga tac tac ggc tac aca ggc gct ttc agg tgt ctg gtt gag aag gga     1584
Gly Tyr Tyr Gly Tyr Thr Gly Ala Phe Arg Cys Leu Val Glu Lys Gly
        515                 520                 525

gat gtg gcc ttt gtg aaa cac cag act gtc cca cag aac act ggg gga     1632
Asp Val Ala Phe Val Lys His Gln Thr Val Pro Gln Asn Thr Gly Gly
    530                 535                 540

aaa aac cct gat cca tgg gct aag aat ctg aat gaa aaa gac tat gag     1680
Lys Asn Pro Asp Pro Trp Ala Lys Asn Leu Asn Glu Lys Asp Tyr Glu
545                 550                 555                 560

ttg ctg tgc ctt gat ggt acc agg aaa cct gtg gag gag tat gcg aac     1728
Leu Leu Cys Leu Asp Gly Thr Arg Lys Pro Val Glu Glu Tyr Ala Asn
                565                 570                 575
```

-continued

```
tgc cac ctg gcc aga gcc ccg aat cac gct gtg gtc aca cgg aaa gat      1776
Cys His Leu Ala Arg Ala Pro Asn His Ala Val Val Thr Arg Lys Asp
            580                 585                 590

aag gaa gct tgc gtc cac aag ata tta cgt caa cag cag cac cta ttt      1824
Lys Glu Ala Cys Val His Lys Ile Leu Arg Gln Gln Gln His Leu Phe
        595                 600                 605

gga agc aac gta act gac tgc tcg ggc aac ttt tgt ttg ttc cgg tcg      1872
Gly Ser Asn Val Thr Asp Cys Ser Gly Asn Phe Cys Leu Phe Arg Ser
    610                 615                 620

gaa acc aag gac ctt ctg ttc aga gat gac aca gta tgt ttg gcc aaa      1920
Glu Thr Lys Asp Leu Leu Phe Arg Asp Asp Thr Val Cys Leu Ala Lys
625                 630                 635                 640

ctt cat gac aga aac aca tat gaa aaa tac tta gga gaa gaa tat gtc      1968
Leu His Asp Arg Asn Thr Tyr Glu Lys Tyr Leu Gly Glu Glu Tyr Val
                645                 650                 655

aag gct gtt ggt aac ctg aga aaa tgc tcc acc t                        2002
Lys Ala Val Gly Asn Leu Arg Lys Cys Ser Thr
            660                 665


<210> SEQ ID NO 23
<211> LENGTH: 667
<212> TYPE: PRT
<213> ORGANISM: Homo sapiens

<400> SEQUENCE: 23

Val Pro Asp Lys Thr Val Arg Trp Cys Ala Val Ser Glu His Glu Ala
1               5                   10                  15

Thr Lys Cys Gln Ser Phe Arg Asp His Met Lys Ser Val Ile Pro Ser
            20                  25                  30

Asp Gly Pro Ser Val Ala Cys Val Lys Lys Ala Ser Tyr Leu Asp Cys
        35                  40                  45

Ile Arg Ala Ile Ala Ala Asn Glu Ala Asp Ala Val Thr Leu Asp Ala
    50                  55                  60

Gly Leu Val Tyr Asp Ala Tyr Leu Ala Pro Asn Asn Leu Lys Pro Val
65                  70                  75                  80

Val Ala Glu Phe Tyr Gly Ser Lys Glu Asp Pro Gln Thr Phe Tyr Tyr
                85                  90                  95

Ala Val Ala Val Val Lys Lys Asp Ser Gly Phe Gln Met Asn Gln Leu
            100                 105                 110

Arg Gly Lys Lys Ser Cys His Thr Gly Leu Gly Arg Ser Ala Gly Trp
        115                 120                 125

Asn Ile Pro Ile Gly Leu Leu Tyr Cys Asp Leu Pro Glu Pro Arg Lys
    130                 135                 140

Pro Leu Glu Lys Ala Val Ala Asn Phe Phe Ser Gly Ser Cys Ala Pro
145                 150                 155                 160

Cys Ala Asp Gly Thr Asp Phe Pro Gln Leu Cys Gln Leu Cys Pro Gly
                165                 170                 175

Cys Gly Cys Ser Thr Leu Asn Gln Tyr Phe Gly Tyr Ser Gly Ala Phe
            180                 185                 190

Lys Cys Leu Lys Asn Gly Ala Gly Asp Val Ala Phe Val Lys His Ser
        195                 200                 205

Thr Ile Phe Glu Asn Leu Ala Asn Lys Ala Asp Arg Asp Gln Tyr Glu
    210                 215                 220

Leu Leu Cys Leu Asp Asn Thr Arg Lys Pro Val Asp Glu Tyr Lys Asp
225                 230                 235                 240

Cys His Leu Ala Gln Val Pro Ser His Thr Val Val Ala Arg Ser Met
```

-continued

```
                245                 250                 255

Gly Gly Lys Glu Asp Leu Ile Trp Glu Leu Leu Asn Gln Ala Gln Glu
            260                 265                 270

His Phe Gly Lys Asp Lys Ser Lys Glu Phe Gln Leu Phe Ser Ser Pro
        275                 280                 285

His Gly Lys Asp Leu Leu Phe Lys Asp Ser Ala His Gly Phe Leu Lys
    290                 295                 300

Val Pro Pro Arg Met Asp Ala Lys Met Tyr Leu Gly Tyr Glu Tyr Val
305                 310                 315                 320

Thr Ala Ile Arg Asn Leu Arg Glu Gly Thr Cys Gln Glu Ala Pro Thr
                325                 330                 335

Asp Glu Cys Lys Pro Val Lys Trp Cys Ala Leu Ser His His Glu Arg
            340                 345                 350

Leu Lys Cys Asp Glu Trp Ser Val Asn Ser Val Gly Lys Ile Glu Cys
        355                 360                 365

Val Ser Ala Glu Thr Thr Glu Asp Cys Ile Ala Lys Ile Met Asn Gly
    370                 375                 380

Glu Ala Asp Ala Met Ser Leu Asp Gly Gly Phe Val Tyr Ile Ala Gly
385                 390                 395                 400

Lys Cys Gly Leu Val Pro Val Leu Ala Glu Asn Tyr Asn Lys Ser Asp
                405                 410                 415

Asn Cys Glu Asp Thr Pro Glu Ala Gly Tyr Phe Ala Val Ala Val Val
            420                 425                 430

Lys Lys Ser Ala Ser Asp Leu Thr Trp Asp Asn Leu Lys Gly Lys Lys
        435                 440                 445

Ser Cys His Thr Ala Val Gly Arg Thr Ala Gly Trp Asn Ile Pro Met
    450                 455                 460

Gly Leu Leu Tyr Asn Lys Ile Asn His Cys Arg Phe Asp Glu Phe Phe
465                 470                 475                 480

Ser Glu Gly Cys Ala Pro Gly Ser Lys Lys Asp Ser Ser Leu Cys Lys
                485                 490                 495

Leu Cys Met Gly Ser Gly Leu Asn Leu Cys Glu Pro Asn Asn Lys Glu
            500                 505                 510

Gly Tyr Tyr Gly Tyr Thr Gly Ala Phe Arg Cys Leu Val Glu Lys Gly
        515                 520                 525

Asp Val Ala Phe Val Lys His Gln Thr Val Pro Gln Asn Thr Gly Gly
    530                 535                 540

Lys Asn Pro Asp Pro Trp Ala Lys Asn Leu Asn Glu Lys Asp Tyr Glu
545                 550                 555                 560

Leu Leu Cys Leu Asp Gly Thr Arg Lys Pro Val Glu Glu Tyr Ala Asn
                565                 570                 575

Cys His Leu Ala Arg Ala Pro Asn His Ala Val Val Thr Arg Lys Asp
            580                 585                 590

Lys Glu Ala Cys Val His Lys Ile Leu Arg Gln Gln Gln His Leu Phe
        595                 600                 605

Gly Ser Asn Val Thr Asp Cys Ser Gly Asn Phe Cys Leu Phe Arg Ser
    610                 615                 620

Glu Thr Lys Asp Leu Leu Phe Arg Asp Asp Thr Val Cys Leu Ala Lys
625                 630                 635                 640

Leu His Asp Arg Asn Thr Tyr Glu Lys Tyr Leu Gly Glu Glu Tyr Val
                645                 650                 655

Lys Ala Val Gly Asn Leu Arg Lys Cys Ser Thr
            660                 665
```

-continued

<210> SEQ ID NO 24
<211> LENGTH: 2394
<212> TYPE: DNA
<213> ORGANISM: Artificial
<220> FEATURE:
<223> OTHER INFORMATION: fusion protein of human transferin and F
      protein TM domein
<220> FEATURE:
<221> NAME/KEY: CDS
<222> LOCATION: (1)..(2394)

<400> SEQUENCE: 24

```
atg gta gca tat atc cag aga tca cag tgc atc tca aca tca cta ctg       48
Met Val Ala Tyr Ile Gln Arg Ser Gln Cys Ile Ser Thr Ser Leu Leu
1               5                   10                  15

gtt gtt ctc acc aca ttg gtc tcg tgt cag att acc ggt gag cag aaa       96
Val Val Leu Thr Thr Leu Val Ser Cys Gln Ile Thr Gly Glu Gln Lys
            20                  25                  30

ctc atc tct gaa gag gat ctg gtc cct gat aaa act gtg aga tgg tgt      144
Leu Ile Ser Glu Glu Asp Leu Val Pro Asp Lys Thr Val Arg Trp Cys
        35                  40                  45

gca gtg tcg gag cat gag gcc act aag tgc cag agt ttc cgc gac cat      192
Ala Val Ser Glu His Glu Ala Thr Lys Cys Gln Ser Phe Arg Asp His
    50                  55                  60

atg aaa agc gtc att cca tcc gat ggt ccc agt gtt gct tgt gtg aag      240
Met Lys Ser Val Ile Pro Ser Asp Gly Pro Ser Val Ala Cys Val Lys
65                  70                  75                  80

aaa gcc tcc tac ctt gat tgc atc agg gcc att gcg gca aac gaa gcg      288
Lys Ala Ser Tyr Leu Asp Cys Ile Arg Ala Ile Ala Ala Asn Glu Ala
                85                  90                  95

gat gct gtg aca ctg gat gca ggt ttg gtg tat gat gct tac ctg gct      336
Asp Ala Val Thr Leu Asp Ala Gly Leu Val Tyr Asp Ala Tyr Leu Ala
            100                 105                 110

ccc aat aac ctg aag cct gtg gtg gca gag ttc tat ggg tca aaa gag      384
Pro Asn Asn Leu Lys Pro Val Val Ala Glu Phe Tyr Gly Ser Lys Glu
        115                 120                 125

gat cca cag act ttc tat tat gct gtt gct gtg gtg aag aag gat agt      432
Asp Pro Gln Thr Phe Tyr Tyr Ala Val Ala Val Val Lys Lys Asp Ser
    130                 135                 140

ggc ttc cag atg aac cag ctt cga ggc aag aag tcc tgc cac acg ggt      480
Gly Phe Gln Met Asn Gln Leu Arg Gly Lys Lys Ser Cys His Thr Gly
145                 150                 155                 160

cta ggc agg tcc gct ggg tgg aac atc ccc ata ggc tta ctt tac tgt      528
Leu Gly Arg Ser Ala Gly Trp Asn Ile Pro Ile Gly Leu Leu Tyr Cys
                165                 170                 175

gac tta cct gag cca cgt aaa cct ctt gag aaa gca gtg gcc aat ttc      576
Asp Leu Pro Glu Pro Arg Lys Pro Leu Glu Lys Ala Val Ala Asn Phe
            180                 185                 190

ttc tcg ggc agc tgt gcc cct tgt gcg gat ggg acg gac ttc ccc cag      624
Phe Ser Gly Ser Cys Ala Pro Cys Ala Asp Gly Thr Asp Phe Pro Gln
        195                 200                 205

ctg tgt caa ctg tgt cca ggg tgt ggc tgc tcc acc ctt aac caa tac      672
Leu Cys Gln Leu Cys Pro Gly Cys Gly Cys Ser Thr Leu Asn Gln Tyr
    210                 215                 220

ttc ggc tac tca gga gcc ttc aag tgt ctg aag aat ggt gct ggg gat      720
Phe Gly Tyr Ser Gly Ala Phe Lys Cys Leu Lys Asn Gly Ala Gly Asp
225                 230                 235                 240

gtg gcc ttt gtc aag cac tcg act ata ttt gag aac ttg gca aac aag      768
Val Ala Phe Val Lys His Ser Thr Ile Phe Glu Asn Leu Ala Asn Lys
                245                 250                 255
```

-continued

```
gct gac agg gac cag tat gag ctg ctt tgc ctg gac aac acc cgg aag      816
Ala Asp Arg Asp Gln Tyr Glu Leu Leu Cys Leu Asp Asn Thr Arg Lys
            260                 265                 270

ccg gta gat gaa tac aag gac tgc cac ttg gcc cag gtc cct tct cat      864
Pro Val Asp Glu Tyr Lys Asp Cys His Leu Ala Gln Val Pro Ser His
        275                 280                 285

acc gtc gtg gcc cga agt atg ggc ggc aag gag gac ttg atc tgg gag      912
Thr Val Val Ala Arg Ser Met Gly Gly Lys Glu Asp Leu Ile Trp Glu
    290                 295                 300

ctt ctc aac cag gcc cag gaa cat ttt ggc aaa gac aaa tca aaa gaa      960
Leu Leu Asn Gln Ala Gln Glu His Phe Gly Lys Asp Lys Ser Lys Glu
305                 310                 315                 320

ttc caa cta ttc agc tct cct cat ggg aag gac ctg ctg ttt aag gac     1008
Phe Gln Leu Phe Ser Ser Pro His Gly Lys Asp Leu Leu Phe Lys Asp
                325                 330                 335

tct gcc cac ggg ttt tta aaa gtc ccc ccc agg atg gat gcc aag atg     1056
Ser Ala His Gly Phe Leu Lys Val Pro Pro Arg Met Asp Ala Lys Met
            340                 345                 350

tac ctg ggc tat gag tat gtc act gcc atc cgg aat cta cgg gaa ggc     1104
Tyr Leu Gly Tyr Glu Tyr Val Thr Ala Ile Arg Asn Leu Arg Glu Gly
        355                 360                 365

aca tgc caa gaa gcc cca aca gat gaa tgc aag cct gtg aag tgg tgt     1152
Thr Cys Gln Glu Ala Pro Thr Asp Glu Cys Lys Pro Val Lys Trp Cys
    370                 375                 380

gcg ctg agc cac cac gag agg ctc aag tgt gat gag tgg agt gtt aac     1200
Ala Leu Ser His His Glu Arg Leu Lys Cys Asp Glu Trp Ser Val Asn
385                 390                 395                 400

agt gta ggg aaa ata gag tgt gta tca gca gag acc acc gaa gac tgc     1248
Ser Val Gly Lys Ile Glu Cys Val Ser Ala Glu Thr Thr Glu Asp Cys
                405                 410                 415

atc gcc aag atc atg aat gga gaa gct gat gcc atg agc ttg gat gga     1296
Ile Ala Lys Ile Met Asn Gly Glu Ala Asp Ala Met Ser Leu Asp Gly
            420                 425                 430

ggg ttt gtc tac ata gcg ggc aag tgt ggt ctg gtg cct gtc ttg gca     1344
Gly Phe Val Tyr Ile Ala Gly Lys Cys Gly Leu Val Pro Val Leu Ala
        435                 440                 445

gaa aac tac aat aag agc gat aat tgt gag gat aca cca gag gca ggg     1392
Glu Asn Tyr Asn Lys Ser Asp Asn Cys Glu Asp Thr Pro Glu Ala Gly
    450                 455                 460

tat ttt gct gta gca gtg gtg aag aaa tca gct tct gac ctc acc tgg     1440
Tyr Phe Ala Val Ala Val Val Lys Lys Ser Ala Ser Asp Leu Thr Trp
465                 470                 475                 480

gac aat ctg aaa ggc aag aag tcc tgc cat acg gca gtt ggc aga acc     1488
Asp Asn Leu Lys Gly Lys Lys Ser Cys His Thr Ala Val Gly Arg Thr
                485                 490                 495

gct ggc tgg aac atc ccc atg ggc ctg ctc tac aat aag atc aac cac     1536
Ala Gly Trp Asn Ile Pro Met Gly Leu Leu Tyr Asn Lys Ile Asn His
            500                 505                 510

tgc aga ttt gat gaa ttt ttc agt gaa ggt tgt gcc cct ggg tct aag     1584
Cys Arg Phe Asp Glu Phe Phe Ser Glu Gly Cys Ala Pro Gly Ser Lys
        515                 520                 525

aaa gac tcc agt ctc tgt aag ctg tgt atg ggc tca ggc cta aac ctg     1632
Lys Asp Ser Ser Leu Cys Lys Leu Cys Met Gly Ser Gly Leu Asn Leu
    530                 535                 540

tgt gaa ccc aac aac aaa gag gga tac tac ggc tac aca ggc gct ttc     1680
Cys Glu Pro Asn Asn Lys Glu Gly Tyr Tyr Gly Tyr Thr Gly Ala Phe
545                 550                 555                 560

agg tgt ctg gtt gag aag gga gat gtg gcc ttt gtg aaa cac cag act     1728
Arg Cys Leu Val Glu Lys Gly Asp Val Ala Phe Val Lys His Gln Thr
                565                 570                 575
```

-continued

```
gtc cca cag aac act ggg gga aaa aac cct gat cca tgg gct aag aat      1776
Val Pro Gln Asn Thr Gly Gly Lys Asn Pro Asp Pro Trp Ala Lys Asn
            580                 585                 590

ctg aat gaa aaa gac tat gag ttg ctg tgc ctt gat ggt acc agg aaa      1824
Leu Asn Glu Lys Asp Tyr Glu Leu Leu Cys Leu Asp Gly Thr Arg Lys
        595                 600                 605

cct gtg gag gag tat gcg aac tgc cac ctg gcc aga gcc ccg aat cac      1872
Pro Val Glu Glu Tyr Ala Asn Cys His Leu Ala Arg Ala Pro Asn His
    610                 615                 620

gct gtg gtc aca cgg aaa gat aag gaa gct tgc gtc cac aag ata tta      1920
Ala Val Val Thr Arg Lys Asp Lys Glu Ala Cys Val His Lys Ile Leu
625                 630                 635                 640

cgt caa cag cag cac cta ttt gga agc aac gta act gac tgc tcg ggc      1968
Arg Gln Gln Gln His Leu Phe Gly Ser Asn Val Thr Asp Cys Ser Gly
            645                 650                 655

aac ttt tgt ttg ttc cgg tcg gaa acc aag gac ctt ctg ttc aga gat      2016
Asn Phe Cys Leu Phe Arg Ser Glu Thr Lys Asp Leu Leu Phe Arg Asp
            660                 665                 670

gac aca gta tgt ttg gcc aaa ctt cat gac aga aac aca tat gaa aaa      2064
Asp Thr Val Cys Leu Ala Lys Leu His Asp Arg Asn Thr Tyr Glu Lys
        675                 680                 685

tac tta gga gaa gaa tat gtc aag gct gtt ggt aac ctg aga aaa tgc      2112
Tyr Leu Gly Glu Glu Tyr Val Lys Ala Val Gly Asn Leu Arg Lys Cys
    690                 695                 700

tcc acc tca tca ctc ctg gaa gcc tgc act ttc cgt aga cct atc ctc      2160
Ser Thr Ser Ser Leu Leu Glu Ala Cys Thr Phe Arg Arg Pro Ile Leu
705                 710                 715                 720

tcg gag gta ggt aga tgg tac aac tca aga gag act gtg att acg atc      2208
Ser Glu Val Gly Arg Trp Tyr Asn Ser Arg Glu Thr Val Ile Thr Ile
                725                 730                 735

ata gta gtt atg gtc gta ata ttg gtg gtc att ata gtg atc atc atc      2256
Ile Val Val Met Val Val Ile Leu Val Val Ile Ile Val Ile Ile Ile
            740                 745                 750

gtg ctt tat aga ctc aga agg tca atg cta atg ggt aat cca gat gac      2304
Val Leu Tyr Arg Leu Arg Arg Ser Met Leu Met Gly Asn Pro Asp Asp
        755                 760                 765

cgt ata ccg agg gac aca tac aca tta gag ccg aag atc aga cat atg      2352
Arg Ile Pro Arg Asp Thr Tyr Thr Leu Glu Pro Lys Ile Arg His Met
    770                 775                 780

tac aca aac ggt ggg ttt gat gca atg gct gag aaa aga tga              2394
Tyr Thr Asn Gly Gly Phe Asp Ala Met Ala Glu Lys Arg
785                 790                 795


<210> SEQ ID NO 25
<211> LENGTH: 797
<212> TYPE: PRT
<213> ORGANISM: Artificial
<220> FEATURE:
<223> OTHER INFORMATION: fusion protein of human transferin and F
      protein TM domein

<400> SEQUENCE: 25

Met Val Ala Tyr Ile Gln Arg Ser Gln Cys Ile Ser Thr Ser Leu Leu
1               5                   10                  15

Val Val Leu Thr Thr Leu Val Ser Cys Gln Ile Thr Gly Glu Gln Lys
            20                  25                  30

Leu Ile Ser Glu Glu Asp Leu Val Pro Asp Lys Thr Val Arg Trp Cys
        35                  40                  45

Ala Val Ser Glu His Glu Ala Thr Lys Cys Gln Ser Phe Arg Asp His
    50                  55                  60
```

-continued

```
Met Lys Ser Val Ile Pro Ser Asp Gly Pro Ser Val Ala Cys Val Lys
65                  70                  75                  80

Lys Ala Ser Tyr Leu Asp Cys Ile Arg Ala Ile Ala Ala Asn Glu Ala
                85                  90                  95

Asp Ala Val Thr Leu Asp Ala Gly Leu Val Tyr Asp Ala Tyr Leu Ala
            100                 105                 110

Pro Asn Asn Leu Lys Pro Val Val Ala Glu Phe Tyr Gly Ser Lys Glu
        115                 120                 125

Asp Pro Gln Thr Phe Tyr Tyr Ala Val Ala Val Val Lys Lys Asp Ser
    130                 135                 140

Gly Phe Gln Met Asn Gln Leu Arg Gly Lys Lys Ser Cys His Thr Gly
145                 150                 155                 160

Leu Gly Arg Ser Ala Gly Trp Asn Ile Pro Ile Gly Leu Leu Tyr Cys
                165                 170                 175

Asp Leu Pro Glu Pro Arg Lys Pro Leu Glu Lys Ala Val Ala Asn Phe
            180                 185                 190

Phe Ser Gly Ser Cys Ala Pro Cys Ala Asp Gly Thr Asp Phe Pro Gln
        195                 200                 205

Leu Cys Gln Leu Cys Pro Gly Cys Gly Cys Ser Thr Leu Asn Gln Tyr
    210                 215                 220

Phe Gly Tyr Ser Gly Ala Phe Lys Cys Leu Lys Asn Gly Ala Gly Asp
225                 230                 235                 240

Val Ala Phe Val Lys His Ser Thr Ile Phe Glu Asn Leu Ala Asn Lys
                245                 250                 255

Ala Asp Arg Asp Gln Tyr Glu Leu Leu Cys Leu Asp Asn Thr Arg Lys
            260                 265                 270

Pro Val Asp Glu Tyr Lys Asp Cys His Leu Ala Gln Val Pro Ser His
        275                 280                 285

Thr Val Val Ala Arg Ser Met Gly Gly Lys Glu Asp Leu Ile Trp Glu
    290                 295                 300

Leu Leu Asn Gln Ala Gln Glu His Phe Gly Lys Asp Lys Ser Lys Glu
305                 310                 315                 320

Phe Gln Leu Phe Ser Ser Pro His Gly Lys Asp Leu Leu Phe Lys Asp
                325                 330                 335

Ser Ala His Gly Phe Leu Lys Val Pro Pro Arg Met Asp Ala Lys Met
            340                 345                 350

Tyr Leu Gly Tyr Glu Tyr Val Thr Ala Ile Arg Asn Leu Arg Glu Gly
        355                 360                 365

Thr Cys Gln Glu Ala Pro Thr Asp Glu Cys Lys Pro Val Lys Trp Cys
    370                 375                 380

Ala Leu Ser His His Glu Arg Leu Lys Cys Asp Glu Trp Ser Val Asn
385                 390                 395                 400

Ser Val Gly Lys Ile Glu Cys Val Ser Ala Glu Thr Thr Glu Asp Cys
                405                 410                 415

Ile Ala Lys Ile Met Asn Gly Glu Ala Asp Ala Met Ser Leu Asp Gly
            420                 425                 430

Gly Phe Val Tyr Ile Ala Gly Lys Cys Gly Leu Val Pro Val Leu Ala
        435                 440                 445

Glu Asn Tyr Asn Lys Ser Asp Asn Cys Glu Asp Thr Pro Glu Ala Gly
    450                 455                 460

Tyr Phe Ala Val Ala Val Val Lys Lys Ser Ala Ser Asp Leu Thr Trp
465                 470                 475                 480
```

-continued

```
Asp Asn Leu Lys Gly Lys Lys Ser Cys His Thr Ala Val Gly Arg Thr
                485                 490                 495

Ala Gly Trp Asn Ile Pro Met Gly Leu Leu Tyr Asn Lys Ile Asn His
            500                 505                 510

Cys Arg Phe Asp Glu Phe Phe Ser Glu Gly Cys Ala Pro Gly Ser Lys
        515                 520                 525

Lys Asp Ser Ser Leu Cys Lys Leu Cys Met Gly Ser Gly Leu Asn Leu
    530                 535                 540

Cys Glu Pro Asn Asn Lys Glu Gly Tyr Tyr Gly Tyr Thr Gly Ala Phe
545                 550                 555                 560

Arg Cys Leu Val Glu Lys Gly Asp Val Ala Phe Val Lys His Gln Thr
                565                 570                 575

Val Pro Gln Asn Thr Gly Gly Lys Asn Pro Asp Pro Trp Ala Lys Asn
            580                 585                 590

Leu Asn Glu Lys Asp Tyr Glu Leu Leu Cys Leu Asp Gly Thr Arg Lys
        595                 600                 605

Pro Val Glu Glu Tyr Ala Asn Cys His Leu Ala Arg Ala Pro Asn His
    610                 615                 620

Ala Val Val Thr Arg Lys Asp Lys Glu Ala Cys Val His Lys Ile Leu
625                 630                 635                 640

Arg Gln Gln Gln His Leu Phe Gly Ser Asn Val Thr Asp Cys Ser Gly
                645                 650                 655

Asn Phe Cys Leu Phe Arg Ser Glu Thr Lys Asp Leu Leu Phe Arg Asp
            660                 665                 670

Asp Thr Val Cys Leu Ala Lys Leu His Asp Arg Asn Thr Tyr Glu Lys
        675                 680                 685

Tyr Leu Gly Glu Glu Tyr Val Lys Ala Val Gly Asn Leu Arg Lys Cys
    690                 695                 700

Ser Thr Ser Ser Leu Leu Glu Ala Cys Thr Phe Arg Arg Pro Ile Leu
705                 710                 715                 720

Ser Glu Val Gly Arg Trp Tyr Asn Ser Arg Glu Thr Val Ile Thr Ile
                725                 730                 735

Ile Val Val Met Val Val Ile Leu Val Val Ile Ile Val Ile Ile Ile
            740                 745                 750

Val Leu Tyr Arg Leu Arg Arg Ser Met Leu Met Gly Asn Pro Asp Asp
        755                 760                 765

Arg Ile Pro Arg Asp Thr Tyr Thr Leu Glu Pro Lys Ile Arg His Met
    770                 775                 780

Tyr Thr Asn Gly Gly Phe Asp Ala Met Ala Glu Lys Arg
785                 790                 795
```